United States Patent
Kobie et al.

(10) Patent No.: US 10,981,976 B2
(45) Date of Patent: Apr. 20, 2021

(54) HUMAN MONOCLONAL ANTIBODIES TO HUMAN ENDOGENOUS RETROVIRUS K ENVELOPE (HERV-K) AND USE THEREOF

(71) Applicants: University of Rochester, Rochester, NY (US); Oregon Health & Science University, Beaverton, OR (US); George Washington University, Washington, DC (US)

(72) Inventors: James J. Kobie, Rochester, NY (US); Jonah B. Sacha, Beaverton, OR (US); Douglas F. Nixon, Washington, DC (US)

(73) Assignees: University of Rochester, Rochester, NY (US); Oregon Health & Science University, Beaverton, OR (US); George Washington University, Washington, DC (US)

( * ) Notice: Subject to any disclaimer, the term of this patent is extended or adjusted under 35 U.S.C. 154(b) by 0 days.

(21) Appl. No.: 16/328,521

(22) PCT Filed: Aug. 30, 2017

(86) PCT No.: PCT/US2017/049269
§ 371 (c)(1),
(2) Date: Feb. 26, 2019

(87) PCT Pub. No.: WO2018/044970
PCT Pub. Date: Mar. 8, 2018

(65) Prior Publication Data
US 2020/0140527 A1    May 7, 2020

Related U.S. Application Data

(60) Provisional application No. 62/381,858, filed on Aug. 31, 2016.

(51) Int. Cl.
C07K 16/10    (2006.01)
C12N 15/85    (2006.01)
A61K 39/42    (2006.01)

(52) U.S. Cl.
CPC .......... C07K 16/1036 (2013.01); A61K 39/42 (2013.01); C12N 15/85 (2013.01); C07K 2317/24 (2013.01); C07K 2317/51 (2013.01); C07K 2317/52 (2013.01); C07K 2317/565 (2013.01); C12N 2015/8518 (2013.01); C12N 2740/10011 (2013.01); C12N 2740/10022 (2013.01)

(58) Field of Classification Search
CPC ............ C07K 16/1036; C07K 2317/24; C07K 2317/51; C07K 2317/52; C07K 2317/565; A61K 39/42; C12N 2740/10011; C12N 2740/10022
See application file for complete search history.

(56) References Cited

FOREIGN PATENT DOCUMENTS

WO    2010138803 A2    12/2010
WO    2013059426 A1    4/2013

OTHER PUBLICATIONS

Franchini, G., and M. L. Bosch, 1989, Genetic relatedness of the human immunodeficiency viruses type 1 and 2 (HIV-1, HIV-2) and the simian immunodeficiency virus (SIV), Annal. N.Y. Acad. Sci. 554(1):81-87.*
Robertson, D. L., et al., 1999, HIV-1 Nomenclature Proposal: A reference guide to HIV-1 classification, in Human Retroviruses and AIDS, Los Alamos National Laboratory, pp. 492-505.*
Bansal, G. P., 2007, A summary of the workshop on passive immunization using monoclonal antibodies for HIV/AIDS, held at the National Institutes of Allergy and Infectious Diseases, Bethesda, Mar. 10, 2006, Biol. 35:367-371.*
Gong, R., et al., 2012, Candidate antibody-based therapeutics against HIV-1, Biodrugs 26(3): 143-162.*
Michaud et al., "Trans-activation, post-transcriptional maturation, and induction of antibodies to HERV-K (HML-2) envelope transmembrane protein in HIV-1 Infection," Retrovirology (2014); 11:pp. 1-15.
Wang-Johanning et al., "Immunotherapeutic Potential of Anti-Human Endogenous Retrovirus-K Envelope Protein Antibodies in Targeting Breast Tumors," Journal of the National Cancer Institute (Feb. 8, 2012); 104(3):1-22.
Michaud et al., "Cutting Edge: An Antibody Recognizing Ancestral Endogenous Virus Glycoproteins Mediates Antibody-Dependent Cellular Cytotoxicity on HIV-1-Infected Cells," The Journal of Immunology (2014) 193:1544-1548.

* cited by examiner

Primary Examiner — Jeffrey S Parkin
(74) Attorney, Agent, or Firm — Fox Rothschild LLP

(57) ABSTRACT

The present invention features anti-HERV-K monoclonal antibodies or antigen-binding portions thereof. The present invention also features uses of the antibodies for treating HIV infection or HIV-associated conditions or diseases.

10 Claims, 1 Drawing Sheet
Specification includes a Sequence Listing.

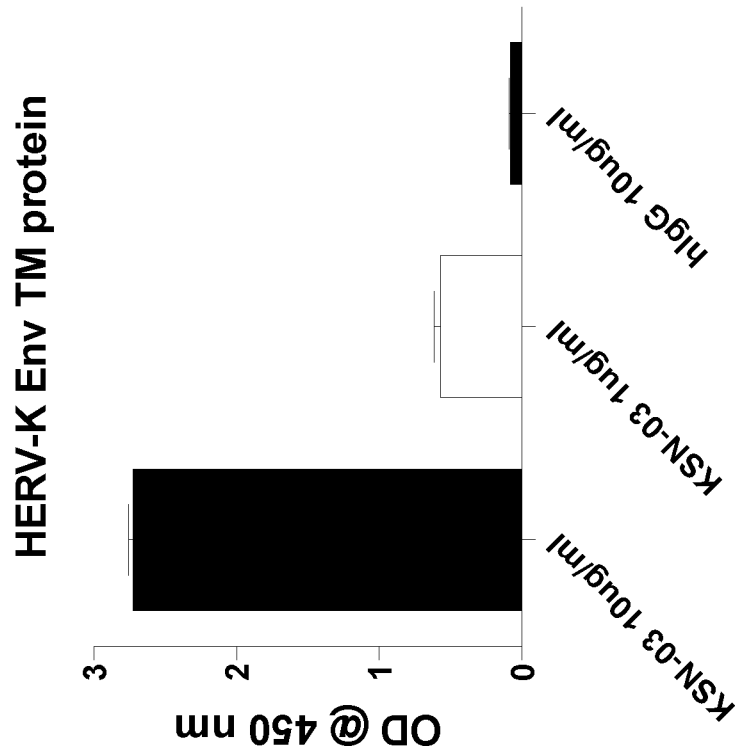
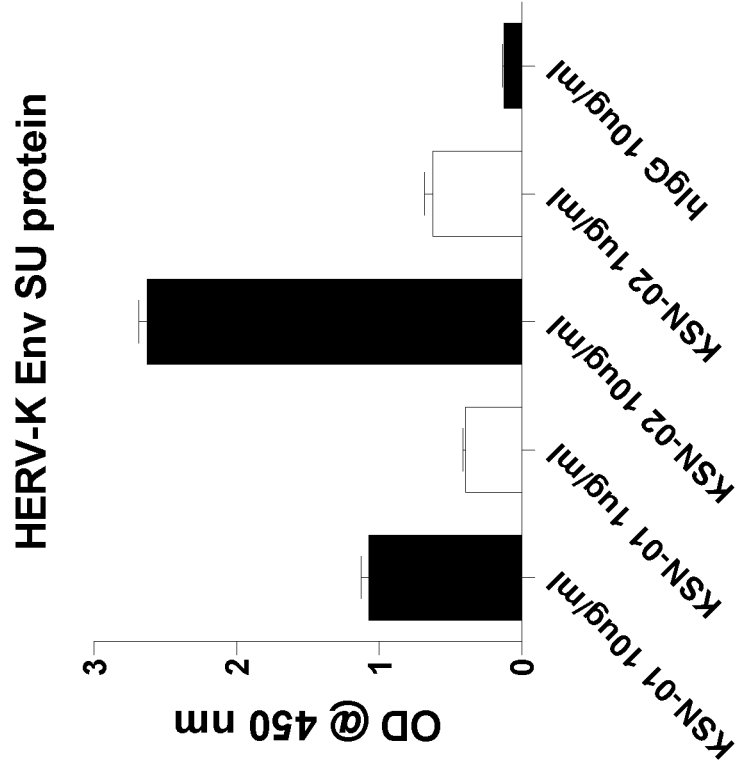

```
                         SEQUENCE LISTING

<160> NUMBER OF SEQ ID NOS: 82

<210> SEQ ID NO 1
<211> LENGTH: 701
<212> TYPE: PRT
<213> ORGANISM: Human endogenous retrovirus K

<400> SEQUENCE: 1

Met Ala Ser Asn Pro Ser Glu Met Gln Arg Lys Ala Pro Pro Arg Arg
1               5                   10                  15

Arg Arg His Arg Asn Arg Ala Pro Leu Thr His Lys Met Asn Lys Met
                20                  25                  30

Val Thr Ser Glu Glu Gln Met Lys Leu Pro Ser Thr Lys Lys Ala Glu
            35                  40                  45

Pro Pro Thr Trp Ala Gln Leu Lys Lys Leu Thr Gln Leu Ala Thr Lys
        50                  55                  60

Tyr Leu Glu Asn Thr Lys Val Thr Gln Thr Pro Glu Ser Met Leu Leu
65                  70                  75                  80

Ala Ala Leu Met Ile Val Ser Met Val Val Ser Leu Pro Met Pro Ala
                85                  90                  95

Gly Ala Ala Ala Ala Asn Tyr Thr Tyr Trp Ala Tyr Val Pro Phe Pro
                100                 105                 110

Pro Leu Ile Arg Ala Val Thr Trp Met Asp Asn Pro Ile Glu Val Tyr
            115                 120                 125

Val Asn Asp Ser Val Trp Val Pro Gly Pro Ile Asp Asp Arg Cys Pro
        130                 135                 140

Ala Lys Pro Glu Glu Glu Gly Met Met Ile Asn Ile Ser Ile Gly Tyr
145                 150                 155                 160

Arg Tyr Pro Pro Ile Cys Leu Gly Arg Ala Pro Gly Cys Leu Met Pro
                165                 170                 175

Ala Val Gln Asn Trp Leu Val Glu Val Pro Thr Val Ser Pro Ile Cys
                180                 185                 190

Arg Phe Thr Tyr His Met Val Ser Gly Met Ser Leu Arg Pro Arg Val
            195                 200                 205

Asn Tyr Leu Gln Asp Phe Ser Tyr Gln Arg Ser Leu Lys Phe Arg Pro
        210                 215                 220

Lys Gly Lys Pro Cys Pro Lys Glu Ile Pro Lys Glu Ser Lys Asn Thr
225                 230                 235                 240

Glu Val Leu Val Trp Glu Glu Cys Val Ala Asn Ser Ala Val Ile Leu
                245                 250                 255

Gln Asn Asn Glu Phe Gly Thr Ile Ile Asp Trp Ala Pro Arg Gly Gln
                260                 265                 270

Phe Tyr His Asn Cys Ser Gly Gln Thr Gln Ser Cys Pro Ser Ala Gln
```

```
                275                 280                 285
Val Ser Pro Ala Val Asp Ser Asp Leu Thr Glu Ser Leu Asp Lys His
290                 295                 300

Lys His Lys Lys Leu Gln Ser Phe Tyr Pro Trp Glu Trp Gly Glu Lys
305                 310                 315                 320

Gly Ile Ser Thr Pro Arg Pro Lys Ile Val Ser Pro Val Ser Gly Pro
                325                 330                 335

Glu His Pro Glu Leu Trp Arg Leu Thr Val Ala Ser His His Ile Arg
                340                 345                 350

Ile Trp Ser Gly Asn Gln Thr Leu Glu Thr Arg Asp Arg Lys Pro Phe
                355                 360                 365

Tyr Thr Ile Asp Leu Asn Ser Ser Leu Thr Val Pro Leu Gln Ser Cys
                370                 375                 380

Val Lys Pro Pro Tyr Met Leu Val Val Gly Asn Ile Val Ile Lys Pro
385                 390                 395                 400

Asp Ser Gln Thr Ile Thr Cys Glu Asn Cys Arg Leu Leu Thr Cys Ile
                405                 410                 415

Asp Ser Thr Phe Asn Trp Gln His Arg Ile Leu Leu Val Arg Ala Arg
                420                 425                 430

Glu Gly Val Trp Ile Pro Val Ser Met Asp Arg Pro Trp Glu Ala Ser
                435                 440                 445

Pro Ser Val His Ile Leu Thr Glu Val Leu Lys Gly Val Leu Asn Arg
450                 455                 460

Ser Lys Arg Phe Ile Phe Thr Leu Ile Ala Val Ile Met Gly Leu Ile
465                 470                 475                 480

Ala Val Thr Ala Thr Ala Ala Val Ala Gly Val Ala Leu His Ser Ser
                485                 490                 495

Val Gln Ser Val Asn Phe Val Asn Asp Trp Gln Lys Asn Ser Thr Arg
                500                 505                 510

Leu Trp Asn Ser Gln Ser Ser Ile Asp Gln Lys Leu Ala Asn Gln Ile
                515                 520                 525

Asn Asp Leu Arg Gln Thr Val Ile Trp Met Gly Asp Arg Leu Met Ser
530                 535                 540

Leu Glu His Arg Phe Gln Leu Gln Cys Asp Trp Asn Thr Ser Asp Phe
545                 550                 555                 560

Cys Ile Thr Pro Gln Ile Tyr Asn Glu Ser Glu His His Trp Asp Met
                565                 570                 575

Val Arg Arg His Leu Gln Gly Arg Glu Asp Asn Leu Thr Leu Asp Ile
                580                 585                 590

Ser Lys Leu Lys Glu Gln Ile Phe Glu Ala Ser Lys Ala His Leu Asn
                595                 600                 605

Leu Val Pro Gly Thr Glu Ala Ile Ala Gly Val Ala Asp Gly Leu Ala
                610                 615                 620

Asn Leu Asn Pro Val Thr Trp Val Lys Thr Ile Gly Ser Thr Thr Ile
625                 630                 635                 640

Ile Asn Leu Ile Leu Ile Leu Val Cys Leu Phe Cys Leu Leu Leu Val
                645                 650                 655

Cys Arg Cys Thr Gln Gln Leu Arg Arg Asp Ser Asp His Arg Glu Arg
                660                 665                 670

Ala Met Met Thr Met Ala Val Leu Ser Lys Arg Lys Gly Gly Asn Val
                675                 680                 685

Gly Lys Ser Lys Arg Asp Gln Ile Val Thr Val Ser Val
                690                 695                 700
```

<210> SEQ ID NO 2
<211> LENGTH: 167
<212> TYPE: PRT
<213> ORGANISM: Human endogenous retrovirus K

<400> SEQUENCE: 2

Ala Val Ala Gly Val Ala Leu His Ser Ser Val Gln Ser Val Asn Phe
1               5                   10                  15

Val Asn Asp Trp Gln Lys Asn Ser Thr Arg Leu Trp Asn Ser Gln Ser
            20                  25                  30

Ser Ile Asp Gln Lys Leu Ala Asn Gln Ile Asn Asp Leu Arg Gln Thr
        35                  40                  45

Val Ile Trp Met Gly Asp Arg Leu Met Ser Leu Glu His Arg Phe Gln
    50                  55                  60

Leu Gln Cys Asp Trp Asn Thr Ser Asp Phe Cys Ile Thr Pro Gln Ile
65                  70                  75                  80

Tyr Asn Glu Ser Glu His His Trp Asp Met Val Arg Arg His Leu Gln
                85                  90                  95

Gly Arg Glu Asp Asn Leu Thr Leu Asp Ile Ser Lys Leu Lys Glu Gln
            100                 105                 110

Ile Phe Glu Ala Ser Lys Ala His Leu Asn Leu Val Pro Gly Thr Glu
        115                 120                 125

Ala Ile Ala Gly Val Ala Asp Gly Leu Ala Asn Leu Asn Pro Val Thr
    130                 135                 140

Trp Val Lys Thr Ile Gly Ser Thr Thr Ile Ile Asn Leu Ile Leu Ile
145                 150                 155                 160

Leu Val Cys Leu Phe Cys Leu
                165

<210> SEQ ID NO 3
<211> LENGTH: 367
<212> TYPE: PRT
<213> ORGANISM: Human endogenous retrovirus K

<400> SEQUENCE: 3

Val Val Ser Leu Pro Met Pro Ala Gly Ala Ala Ala Asn Tyr Thr
1               5                   10                  15

Tyr Trp Ala Tyr Val Pro Phe Pro Pro Leu Ile Arg Ala Val Thr Trp
            20                  25                  30

Met Asp Asn Pro Ile Glu Val Tyr Val Asn Asp Ser Val Trp Val Pro
        35                  40                  45

Gly Pro Ile Asp Asp Arg Cys Pro Ala Lys Pro Glu Glu Glu Gly Met
    50                  55                  60

Met Ile Asn Ile Ser Ile Gly Tyr Arg Tyr Pro Pro Ile Cys Leu Gly
65                  70                  75                  80

Arg Ala Pro Gly Cys Leu Met Pro Ala Val Gln Asn Trp Leu Val Glu
                85                  90                  95

Val Pro Thr Val Ser Pro Ile Cys Arg Phe Thr Tyr His Met Val Ser
            100                 105                 110

Gly Met Ser Leu Arg Pro Arg Val Asn Tyr Leu Gln Asp Phe Ser Tyr
        115                 120                 125

Gln Arg Ser Leu Lys Phe Arg Pro Lys Gly Lys Pro Cys Pro Lys Glu
    130                 135                 140

Ile Pro Lys Glu Ser Lys Asn Thr Glu Val Leu Val Trp Glu Glu Cys
145                 150                 155                 160

```
Val Ala Asn Ser Ala Val Ile Leu Gln Asn Asn Glu Phe Gly Thr Ile
                165                 170                 175

Ile Asp Trp Ala Pro Arg Gly Gln Phe Tyr His Asn Cys Ser Gly Gln
            180                 185                 190

Thr Gln Ser Cys Pro Ser Ala Gln Val Ser Pro Ala Val Asp Ser Asp
        195                 200                 205

Leu Thr Glu Ser Leu Asp Lys His Lys His Lys Leu Gln Ser Phe
    210                 215                 220

Tyr Pro Trp Glu Trp Gly Gly Lys Gly Ile Ser Thr Pro Arg Pro Lys
225                 230                 235                 240

Ile Val Ser Pro Val Ser Gly Pro Glu His Pro Glu Leu Trp Arg Leu
                245                 250                 255

Thr Val Ala Ser His His Ile Arg Ile Trp Ser Gly Asn Gln Thr Leu
                260                 265                 270

Glu Thr Arg Asp Arg Lys Pro Phe Tyr Thr Ile Asp Leu Asn Ser Ser
            275                 280                 285

Leu Thr Val Pro Leu Gln Ser Cys Val Lys Pro Pro Tyr Met Leu Val
    290                 295                 300

Val Gly Asn Ile Val Ile Lys Pro Asp Ser Gln Thr Ile Thr Cys Glu
305                 310                 315                 320

Asn Cys Arg Leu Leu Thr Cys Ile Asp Ser Thr Phe Asn Trp Gln His
                325                 330                 335

Arg Ile Leu Leu Val Arg Ala Arg Glu Gly Val Trp Ile Pro Val Ser
            340                 345                 350

Met Asp Arg Pro Trp Glu Ala Ser Pro Ser Val His Ile Leu Thr
            355                 360                 365

<210> SEQ ID NO 4
<211> LENGTH: 9
<212> TYPE: PRT
<213> ORGANISM: Homo sapiens

<400> SEQUENCE: 4

Gly Asp Ser Val Ser Ser Asn Ser Ala
1               5

<210> SEQ ID NO 5
<211> LENGTH: 9
<212> TYPE: PRT
<213> ORGANISM: Homo sapiens

<400> SEQUENCE: 5

Thr Tyr Tyr Arg Ser Lys Trp Tyr Asn
1               5

<210> SEQ ID NO 6
<211> LENGTH: 22
<212> TYPE: PRT
<213> ORGANISM: Homo sapiens

<400> SEQUENCE: 6

Cys Ala Arg Asp Arg Pro Trp Arg Gly Tyr Arg Gly Tyr Tyr Tyr Tyr
1               5                   10                  15

Tyr Gly Met Asp Val Trp
            20

<210> SEQ ID NO 7
<211> LENGTH: 6
```

```
<212> TYPE: PRT
<213> ORGANISM: Homo sapiens

<400> SEQUENCE: 7

Gln Ser Ile Ser Ser Trp
1               5

<210> SEQ ID NO 8
<211> LENGTH: 3
<212> TYPE: PRT
<213> ORGANISM: Homo sapiens

<400> SEQUENCE: 8

Lys Ala Ser
1

<210> SEQ ID NO 9
<211> LENGTH: 11
<212> TYPE: PRT
<213> ORGANISM: Homo sapiens

<400> SEQUENCE: 9

Cys Gln Gln Tyr Asn Ser Tyr Ser Trp Thr Phe
1               5                   10

<210> SEQ ID NO 10
<211> LENGTH: 8
<212> TYPE: PRT
<213> ORGANISM: Homo sapiens

<400> SEQUENCE: 10

Gly Gly Ser Phe Ser Gly Tyr Tyr
1               5

<210> SEQ ID NO 11
<211> LENGTH: 7
<212> TYPE: PRT
<213> ORGANISM: Homo sapiens

<400> SEQUENCE: 11

Ile Asn His Ser Gly Ser Thr
1               5

<210> SEQ ID NO 12
<211> LENGTH: 23
<212> TYPE: PRT
<213> ORGANISM: Homo sapiens

<400> SEQUENCE: 12

Cys Ala Arg Gly Arg Pro Leu Leu Arg Phe Leu Glu Trp Ser Arg Pro
1               5                   10                  15

Tyr Tyr Tyr Met Asp Val Trp
            20

<210> SEQ ID NO 13
<211> LENGTH: 8
<212> TYPE: PRT
<213> ORGANISM: Homo sapiens

<400> SEQUENCE: 13

Ser Gly Ser Ile Ala Ser Asn Tyr
1               5

<210> SEQ ID NO 14
```

```
<211> LENGTH: 3
<212> TYPE: PRT
<213> ORGANISM: Homo sapiens

<400> SEQUENCE: 14

Glu Asp Asn
1

<210> SEQ ID NO 15
<211> LENGTH: 12
<212> TYPE: PRT
<213> ORGANISM: Homo sapiens

<400> SEQUENCE: 15

Cys Gln Ser Tyr Asp Ser Ser Asn His Trp Val Phe
1               5                   10

<210> SEQ ID NO 16
<211> LENGTH: 8
<212> TYPE: PRT
<213> ORGANISM: Homo sapiens

<400> SEQUENCE: 16

Gly Phe Thr Phe Ser Ser Tyr Gly
1               5

<210> SEQ ID NO 17
<211> LENGTH: 8
<212> TYPE: PRT
<213> ORGANISM: Homo sapiens

<400> SEQUENCE: 17

Ile Trp Tyr Asp Gly Ser Asn Lys
1               5

<210> SEQ ID NO 18
<211> LENGTH: 16
<212> TYPE: PRT
<213> ORGANISM: Homo sapiens

<400> SEQUENCE: 18

Cys Ala Lys Arg Gly Gly Leu Glu Gly Phe Tyr Tyr Phe Asp Tyr Trp
1               5                   10                  15

<210> SEQ ID NO 19
<211> LENGTH: 6
<212> TYPE: PRT
<213> ORGANISM: Homo sapiens

<400> SEQUENCE: 19

Gln Ser Ile Ser Ser Trp
1               5

<210> SEQ ID NO 20
<211> LENGTH: 3
<212> TYPE: PRT
<213> ORGANISM: Homo sapiens

<400> SEQUENCE: 20

Lys Ala Ser
1

<210> SEQ ID NO 21
<211> LENGTH: 10
<212> TYPE: PRT
```

<213> ORGANISM: Homo sapiens

<400> SEQUENCE: 21

Cys Gln Gln Tyr Asn Ser Tyr Ser Ser Phe
1               5                   10

<210> SEQ ID NO 22
<211> LENGTH: 98
<212> TYPE: PRT
<213> ORGANISM: Homo sapiens

<400> SEQUENCE: 22

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe

<210> SEQ ID NO 23
<211> LENGTH: 120
<212> TYPE: PRT
<213> ORGANISM: Homo sapiens

<400> SEQUENCE: 23

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Arg Pro Trp Arg Gly Tyr Arg Gly Tyr Tyr
            100                 105                 110

Tyr Tyr Tyr Gly Met Asp Val Trp
        115                 120

<210> SEQ ID NO 24
<211> LENGTH: 119
<212> TYPE: PRT
<213> ORGANISM: Homo sapiens

<400> SEQUENCE: 24

Asn Phe Met Leu Thr Gln Pro His Ser Val Ser Glu Ser Pro Gly Lys
1               5                   10                  15

Thr Val Thr Ile Ser Cys Thr Arg Ser Ser Gly Ser Ile Ala Ser Asn

```
            20                  25                  30
Tyr Val Gln Trp Tyr Gln Gln Arg Pro Gly Ser Ala Pro Thr Thr Val
            35                  40                  45

Ile Tyr Glu Asp Asn Gln Arg Pro Ser Gly Val Pro Asp Arg Phe Ser
            50                  55                  60

Gly Ser Ile Asp Ser Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Ser Asn His Trp Val Phe Gly Gly Gly Thr Lys Leu Thr Val Leu Gly
               100                 105                 110

Gln Pro Lys Ala Ala Pro Ser
               115

<210> SEQ ID NO 25
<211> LENGTH: 119
<212> TYPE: PRT
<213> ORGANISM: Homo sapiens

<400> SEQUENCE: 25

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Pro Leu Leu Arg Phe Leu Glu Trp Ser Arg Pro Tyr Tyr
               100                 105                 110

Tyr Met Asp Val Trp Gly Lys
               115

<210> SEQ ID NO 26
<211> LENGTH: 96
<212> TYPE: PRT
<213> ORGANISM: Homo sapiens

<400> SEQUENCE: 26

Ile Arg Met Thr Gln Ser Pro Ser Thr Leu Ser Ala Ser Val Gly Asp
1               5                   10                  15

Arg Val Thr Ile Thr Cys Arg Ala Ser Gln Ser Ile Ser Ser Trp Leu
            20                  25                  30

Ala Trp Tyr Gln Gln Lys Pro Gly Lys Ala Pro Lys Leu Leu Ile Tyr
            35                  40                  45

Lys Ala Ser Ser Leu Glu Ser Gly Val Pro Ser Arg Phe Ser Gly Ser
            50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Gln Gln Tyr Asn Ser Tyr Ser Ser Phe
                85                  90                  95
```

<210> SEQ ID NO 27
<211> LENGTH: 119
<212> TYPE: PRT
<213> ORGANISM: Homo sapiens

<400> SEQUENCE: 27

Val Gln Leu Val Glu Ser Gly Gly Val Val Gln Pro Gly Arg Ser
1               5                   10                  15

Leu Arg Leu Ser Cys Ala Ala Ser Gly Phe Thr Phe Ser Ser Tyr Gly
            20                  25                  30

Met His Trp Val Arg Gln Ala Pro Gly Lys Gly Leu Glu Trp Val Ala
        35                  40                  45

Val Ile Trp Tyr Asp Gly Ser Asn Lys Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Arg Gly Gly Leu Glu Gly Phe Tyr Tyr Phe Asp Tyr Trp Gly Gln
            100                 105                 110

Gly Thr Leu Val Thr Val Ser
        115

<210> SEQ ID NO 28
<211> LENGTH: 391
<212> TYPE: DNA
<213> ORGANISM: Homo sapiens

<400> SEQUENCE: 28
caggtacagc tgcagcagtc aggtccagga ctggtgaagc cctcgcagac cctctcactc      60
acctgtgcca tctccgggga cagtgtctct agcaacagtg ctgcttggaa ctggatcagg     120
cagtccccat cgagaggcct tgagtggctg gaaggacat actacaggtc caagtggtat      180
aatgattatg cagtatctgt gaaaagtcga ataaccatca cccagacac atccaagaac      240
cagttctccc tgcagctgaa ctctgtgact cccgaggaca cggctgtgta ttactgtgca     300
agagataggc cctggcgtgg ttaccgaggt tactactact agtacggtat ggacgtctgg    360
ggccaaggga ccacggtcac cgtctcctca g                                    391

<210> SEQ ID NO 29
<211> LENGTH: 322
<212> TYPE: DNA
<213> ORGANISM: Homo sapiens

<400> SEQUENCE: 29
gacatccaga tgacccagtc tccttccacc ctgtctgcat ctgtaggaga cagagtcacc      60
atcacttgcc gggccagtca gagtattagt agctggttgg cctggtatca gcagaaacca    120
gggaaagccc ctaagctcct gatctataag gcgtctagtt tagaaagtgg ggtcccatca    180
aggttcagcg gcagtggatc tgggacagaa ttcactctca ccatcagcag cctgcagcct    240
gatgattttg caacttatta ctgccaacag tataatagtt attcgtggac gttcggccaa    300
gggaccaagg tggaaatcaa ac                                              322

<210> SEQ ID NO 30
<211> LENGTH: 382
<212> TYPE: DNA
<213> ORGANISM: Homo sapiens

<400> SEQUENCE: 30

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagacacgt ccaagaacca gttctccctg   240
aagctgagct ctgtgaccgc cgcggacacg gctgtgtatt actgtgcgag aggccgcccg   300
ttattacgat ttttggagtg gtccaggccc tactactaca tggacgtctg ggcaaaggg   360
accacggtca ccgtctcctc ag                                            382
```

<210> SEQ ID NO 31
<211> LENGTH: 360
<212> TYPE: DNA
<213> ORGANISM: Homo sapiens

<400> SEQUENCE: 31

```
aattttatgc tgactcagcc gcactctgtg tcggagtctc cggggaagac ggtaaccatc    60
tcctgcaccc gcagcagtgg cagcattgcc agcaactatg tgcagtggta ccagcagcgc   120
ccgggcagtg cccccaccac tgtgatctat gaggataacc aaagaccctc tggggtccct   180
gatcggttct ctggctccat cgacagctcc tccaactctg cctccctcac catctctgga   240
ctgaagactg aggacgaggc tgactactac tgtcagtctt atgatagcag caaccattgg   300
gtgttcggcg agggaccaa gctgaccgtc ctaggtcagc ccaaggctgc cccctcggtc   360
```

<210> SEQ ID NO 32
<211> LENGTH: 360
<212> TYPE: DNA
<213> ORGANISM: Homo sapiens

<400> SEQUENCE: 32

```
aggtgcagct ggtggagtct gggggaggcg tggtccagcc tgggaggtcc ctgagactct    60
cctgtgcagc gtctggattc accttcagta gctatggcat gcactgggtc cgccaggctc   120
caggcaaggg gctggagtgg gtggcagtta tatggtatga tggaagtaat aaatactatg   180
cagactccgt gaagggccga ttcaccatct ccagagacaa ttccaagaac acgctgtatc   240
tgcaaatgaa cagcctgaga gccgaggaca cggctgtgta ttactgtgcg aaacgagggg   300
ggttggaggg cttctactac tttgactact ggggccaggg aaccctggtc accgtctcct   360
```

<210> SEQ ID NO 33
<211> LENGTH: 317
<212> TYPE: DNA
<213> ORGANISM: Homo sapiens

<400> SEQUENCE: 33

```
catccggatg acccagtctc cttccaccct gtccgcatct gtaggagaca gagtcaccat    60
cacttgccgg gccagtcaga gtattagtag ctggttggcc tggtatcagc agaaaccagg   120
gaaagcccct aagctcctga tctataaggc gtctagttta aaagtggggg tcccatcaag   180
gttcagcggc agtggatctg ggacagaatt cactctcacc atcagcagcc tgcagcctga   240
tgattttgca acttattact gccaacagta taatagttat cctctctttcg gccctgggac   300
caagctggag atcaaac                                                  317
```

<210> SEQ ID NO 34
<211> LENGTH: 20

```
<212> TYPE: DNA
<213> ORGANISM: Artificial
<220> FEATURE:
<223> OTHER INFORMATION: Synthetic

<400> SEQUENCE: 34
atggactgga cctggaggat                                              20

<210> SEQ ID NO 35
<211> LENGTH: 20
<212> TYPE: DNA
<213> ORGANISM: Artificial
<220> FEATURE:
<223> OTHER INFORMATION: Synthetic

<400> SEQUENCE: 35
atggactgga cctggagcat                                              20

<210> SEQ ID NO 36
<211> LENGTH: 20
<212> TYPE: DNA
<213> ORGANISM: Artificial
<220> FEATURE:
<223> OTHER INFORMATION: Synthetic

<400> SEQUENCE: 36
atggactgga cctggagaat                                              20

<210> SEQ ID NO 37
<211> LENGTH: 19
<212> TYPE: DNA
<213> ORGANISM: Artificial
<220> FEATURE:
<223> OTHER INFORMATION: Synthetic

<400> SEQUENCE: 37
ggttcctctt tgtggtggc                                               19

<210> SEQ ID NO 38
<211> LENGTH: 20
<212> TYPE: DNA
<213> ORGANISM: Artificial
<220> FEATURE:
<223> OTHER INFORMATION: Synthetic

<400> SEQUENCE: 38
atggactgga cctggagggt                                              20

<210> SEQ ID NO 39
<211> LENGTH: 20
<212> TYPE: DNA
<213> ORGANISM: Artificial
<220> FEATURE:
<223> OTHER INFORMATION: Synthetic

<400> SEQUENCE: 39
atggactgga tttggaggat                                              20

<210> SEQ ID NO 40
<211> LENGTH: 22
<212> TYPE: DNA
<213> ORGANISM: Artificial
<220> FEATURE:
<223> OTHER INFORMATION: Synthetic

<400> SEQUENCE: 40
```
aggttcctct ttgtggtggc ag                                                22

<210> SEQ ID NO 41
<211> LENGTH: 20
<212> TYPE: DNA
<213> ORGANISM: Artificial
<220> FEATURE:
<223> OTHER INFORMATION: Synthetic

<400> SEQUENCE: 41
catactttgt tccacgctcc                                                   20

<210> SEQ ID NO 42
<211> LENGTH: 17
<212> TYPE: DNA
<213> ORGANISM: Artificial
<220> FEATURE:
<223> OTHER INFORMATION: Synthetic

<400> SEQUENCE: 42
taaaaggtgt ccagtgt                                                      17

<210> SEQ ID NO 43
<211> LENGTH: 17
<212> TYPE: DNA
<213> ORGANISM: Artificial
<220> FEATURE:
<223> OTHER INFORMATION: Synthetic

<400> SEQUENCE: 43
taagaggtgt ccagtgt                                                      17

<210> SEQ ID NO 44
<211> LENGTH: 17
<212> TYPE: DNA
<213> ORGANISM: Artificial
<220> FEATURE:
<223> OTHER INFORMATION: Synthetic

<400> SEQUENCE: 44
tagaaggtgt ccagtgt                                                      17

<210> SEQ ID NO 45
<211> LENGTH: 24
<212> TYPE: DNA
<213> ORGANISM: Artificial
<220> FEATURE:
<223> OTHER INFORMATION: Synthetic

<400> SEQUENCE: 45
gctattttta aggtgtcca gtgt                                               24

<210> SEQ ID NO 46
<211> LENGTH: 17
<212> TYPE: DNA
<213> ORGANISM: Artificial
<220> FEATURE:
<223> OTHER INFORMATION: Synthetic

<400> SEQUENCE: 46
tacaaggtgt ccagtgt                                                      17

<210> SEQ ID NO 47
<211> LENGTH: 17
<212> TYPE: DNA
<213> ORGANISM: Artificial

```
<220> FEATURE:
<223> OTHER INFORMATION: Synthetic

<400> SEQUENCE: 47
ttaaagctgt ccagtgt                                                  17

<210> SEQ ID NO 48
<211> LENGTH: 22
<212> TYPE: DNA
<213> ORGANISM: Artificial
<220> FEATURE:
<223> OTHER INFORMATION: Synthetic

<400> SEQUENCE: 48
atgaaacacc tgtggttctt cc                                            22

<210> SEQ ID NO 49
<211> LENGTH: 20
<212> TYPE: DNA
<213> ORGANISM: Artificial
<220> FEATURE:
<223> OTHER INFORMATION: Synthetic

<400> SEQUENCE: 49
atgaaacacc tgtggttctt                                               20

<210> SEQ ID NO 50
<211> LENGTH: 20
<212> TYPE: DNA
<213> ORGANISM: Artificial
<220> FEATURE:
<223> OTHER INFORMATION: Synthetic

<400> SEQUENCE: 50
atgaagcacc tgtggttctt                                               20

<210> SEQ ID NO 51
<211> LENGTH: 20
<212> TYPE: DNA
<213> ORGANISM: Artificial
<220> FEATURE:
<223> OTHER INFORMATION: Synthetic

<400> SEQUENCE: 51
atgaaacatc tgtggttctt                                               20

<210> SEQ ID NO 52
<211> LENGTH: 17
<212> TYPE: DNA
<213> ORGANISM: Artificial
<220> FEATURE:
<223> OTHER INFORMATION: Synthetic

<400> SEQUENCE: 52
ttctccaagg agtctgt                                                  17

<210> SEQ ID NO 53
<211> LENGTH: 19
<212> TYPE: DNA
<213> ORGANISM: Artificial
<220> FEATURE:
<223> OTHER INFORMATION: Synthetic

<400> SEQUENCE: 53
cctccacagt gagagtctg                                                19
```

<210> SEQ ID NO 54
<211> LENGTH: 21
<212> TYPE: DNA
<213> ORGANISM: Artificial
<220> FEATURE:
<223> OTHER INFORMATION: Synthetic

<400> SEQUENCE: 54
atgtctgtct ccttcctcat c                                             21

<210> SEQ ID NO 55
<211> LENGTH: 21
<212> TYPE: DNA
<213> ORGANISM: Artificial
<220> FEATURE:
<223> OTHER INFORMATION: Synthetic

<400> SEQUENCE: 55
ggcagcagca acaggtgccc a                                             21

<210> SEQ ID NO 56
<211> LENGTH: 20
<212> TYPE: DNA
<213> ORGANISM: Artificial
<220> FEATURE:
<223> OTHER INFORMATION: Synthetic

<400> SEQUENCE: 56
gtgatggagt cgggaaggaa                                               20

<210> SEQ ID NO 57
<211> LENGTH: 20
<212> TYPE: DNA
<213> ORGANISM: Artificial
<220> FEATURE:
<223> OTHER INFORMATION: Synthetic

<400> SEQUENCE: 57
gtgtagtgct tcacgtggca                                               20

<210> SEQ ID NO 58
<211> LENGTH: 20
<212> TYPE: DNA
<213> ORGANISM: Artificial
<220> FEATURE:
<223> OTHER INFORMATION: Synthetic

<400> SEQUENCE: 58
gagtcctgag gactgtagga                                               20

<210> SEQ ID NO 59
<211> LENGTH: 20
<212> TYPE: DNA
<213> ORGANISM: Artificial
<220> FEATURE:
<223> OTHER INFORMATION: Synthetic

<400> SEQUENCE: 59
cgacggggaa ttctcacagg                                               20

<210> SEQ ID NO 60
<211> LENGTH: 20
<212> TYPE: DNA
<213> ORGANISM: Artificial
<220> FEATURE:
<223> OTHER INFORMATION: Synthetic

<400> SEQUENCE: 60
cgacggggaa ttctcacagg                                              20

<210> SEQ ID NO 61
<211> LENGTH: 20
<212> TYPE: DNA
<213> ORGANISM: Artificial
<220> FEATURE:
<223> OTHER INFORMATION: Synthetic

<400> SEQUENCE: 61
gcgcctgagt tccacgacac                                              20

<210> SEQ ID NO 62
<211> LENGTH: 25
<212> TYPE: DNA
<213> ORGANISM: Artificial
<220> FEATURE:
<223> OTHER INFORMATION: Synthetic

<400> SEQUENCE: 62
atgaggstcc cygctcagct gctgg                                        25

<210> SEQ ID NO 63
<211> LENGTH: 26
<212> TYPE: DNA
<213> ORGANISM: Artificial
<220> FEATURE:
<223> OTHER INFORMATION: Synthetic

<400> SEQUENCE: 63
ctcttcctcc tgctactctg gctccc                                       26

<210> SEQ ID NO 64
<211> LENGTH: 25
<212> TYPE: DNA
<213> ORGANISM: Artificial
<220> FEATURE:
<223> OTHER INFORMATION: Synthetic

<400> SEQUENCE: 64
atttctctgt tgctctggat ctctg                                        25

<210> SEQ ID NO 65
<211> LENGTH: 24
<212> TYPE: DNA
<213> ORGANISM: Artificial
<220> FEATURE:
<223> OTHER INFORMATION: Synthetic

<400> SEQUENCE: 65
gtttctcgta gtctgctttg ctca                                         24

<210> SEQ ID NO 66
<211> LENGTH: 24
<212> TYPE: DNA
<213> ORGANISM: Artificial
<220> FEATURE:
<223> OTHER INFORMATION: Synthetic

<400> SEQUENCE: 66
atgacccagw ctccabycwc cctg                                         24

<210> SEQ ID NO 67

<211> LENGTH: 22
<212> TYPE: DNA
<213> ORGANISM: Artificial
<220> FEATURE:
<223> OTHER INFORMATION: Synthetic

<400> SEQUENCE: 67
gtgctgtcct tgctgtcctg ct                                              22

<210> SEQ ID NO 68
<211> LENGTH: 23
<212> TYPE: DNA
<213> ORGANISM: Artificial
<220> FEATURE:
<223> OTHER INFORMATION: Synthetic

<400> SEQUENCE: 68
ggtcctgggc ccagtctgtg ctg                                             23

<210> SEQ ID NO 69
<211> LENGTH: 23
<212> TYPE: DNA
<213> ORGANISM: Artificial
<220> FEATURE:
<223> OTHER INFORMATION: Synthetic

<400> SEQUENCE: 69
ggtcctgggc ccagtctgcc ctg                                             23

<210> SEQ ID NO 70
<211> LENGTH: 23
<212> TYPE: DNA
<213> ORGANISM: Artificial
<220> FEATURE:
<223> OTHER INFORMATION: Synthetic

<400> SEQUENCE: 70
gctctgtgac ctcctatgag ctg                                             23

<210> SEQ ID NO 71
<211> LENGTH: 23
<212> TYPE: DNA
<213> ORGANISM: Artificial
<220> FEATURE:
<223> OTHER INFORMATION: Synthetic

<400> SEQUENCE: 71
ggtctctctc scagcytgtg ctg                                             23

<210> SEQ ID NO 72
<211> LENGTH: 23
<212> TYPE: DNA
<213> ORGANISM: Artificial
<220> FEATURE:
<223> OTHER INFORMATION: Synthetic

<400> SEQUENCE: 72
gttcttgggc caattttatg ctg                                             23

<210> SEQ ID NO 73
<211> LENGTH: 23
<212> TYPE: DNA
<213> ORGANISM: Artificial
<220> FEATURE:
<223> OTHER INFORMATION: Synthetic

<400> SEQUENCE: 73

```
ggtccaattc ycaggctgtg gtg                                           23

<210> SEQ ID NO 74
<211> LENGTH: 23
<212> TYPE: DNA
<213> ORGANISM: Artificial
<220> FEATURE:
<223> OTHER INFORMATION: Synthetic

<400> SEQUENCE: 74
gagtggattc tcagactgtg gtg                                           23

<210> SEQ ID NO 75
<211> LENGTH: 24
<212> TYPE: DNA
<213> ORGANISM: Artificial
<220> FEATURE:
<223> OTHER INFORMATION: Synthetic

<400> SEQUENCE: 75
caccagtgtg gccttgttgc cttg                                          24

<210> SEQ ID NO 76
<211> LENGTH: 25
<212> TYPE: DNA
<213> ORGANISM: Artificial
<220> FEATURE:
<223> OTHER INFORMATION: Synthetic

<400> SEQUENCE: 76
ctgctaccgg ttcctgggcc cagtc                                         25

<210> SEQ ID NO 77
<211> LENGTH: 25
<212> TYPE: DNA
<213> ORGANISM: Artificial
<220> FEATURE:
<223> OTHER INFORMATION: Synthetic

<400> SEQUENCE: 77
ctgctaccgg ttcctgggcc cagtc                                         25

<210> SEQ ID NO 78
<211> LENGTH: 26
<212> TYPE: DNA
<213> ORGANISM: Artificial
<220> FEATURE:
<223> OTHER INFORMATION: Synthetic

<400> SEQUENCE: 78
ctgctaccgg ttctgtgacc tcctat                                        26

<210> SEQ ID NO 79
<211> LENGTH: 26
<212> TYPE: DNA
<213> ORGANISM: Artificial
<220> FEATURE:
<223> OTHER INFORMATION: Synthetic

<400> SEQUENCE: 79
ctgctaccgg ttctctctcs cagcyt                                        26

<210> SEQ ID NO 80
<211> LENGTH: 26
<212> TYPE: DNA
```

```
<213> ORGANISM: Artificial
<220> FEATURE:
<223> OTHER INFORMATION: Synthetic

<400> SEQUENCE: 80
ctgctaccgg ttcttgggcc aatttt                                          26

<210> SEQ ID NO 81
<211> LENGTH: 26
<212> TYPE: DNA
<213> ORGANISM: Artificial
<220> FEATURE:
<223> OTHER INFORMATION: Synthetic

<400> SEQUENCE: 81
ctgctaccgg ttccaattcy cagrct                                          26

<210> SEQ ID NO 82
<211> LENGTH: 25
<212> TYPE: DNA
<213> ORGANISM: Artificial
<220> FEATURE:
<223> OTHER INFORMATION: Synthetic

<400> SEQUENCE: 82
ctcctcactc gagggyggga acaga                                           25
```

HUMAN MONOCLONAL ANTIBODIES TO HUMAN ENDOGENOUS RETROVIRUS K ENVELOPE (HERV-K) AND USE THEREOF

CROSS-REFERENCE TO RELATED APPLICATIONS

The present Application is the U.S. National Phase of International Patent Application No. PCT/US2017/049269, filed Aug. 30, 2017, which claims priority to U.S. Provisional Patent Application Ser. No. 62/381,858, filed Aug. 31, 2016, the disclosures of which are hereby incorporated by reference in their entirety.

FIELD OF THE INVENTION

The present invention relates to an isolated antibody or the antigen-binding portion thereof that specifically binds to human endogenous retrovirus-K (HERV-K) envelope polypeptide. The present invention further relates to the therapeutic uses of the isolated antibody or the antigen-binding portion thereof.

BACKGROUND OF THE INVENTION

Human Endogenous Retroviruses (HERV) are remnants of past retroviral infections during human evolution and constitute about 8% of the human genome. Most HERVs are dysfunctional and subsequently silent due to extensive mutations and deletions in their encoded genes.

HERV-K species, especially the HML-2 clade, is the most recent to enter the human genome, perhaps as recently as 150,000 years ago. There are estimated to be approximately 1000 HERV-K insertions and between 30 and 50 HERV-K proviruses in the human genome. Certain HERV-K loci are capable of expressing all of the viral proteins, and viral particle formation has been detected in teratocarcinoma cell lines. Transcription of HERV-K is strongly affected by apolipoprotein B mRNA-editing, enzyme-catalytic, polypeptide-like 3G/F (APOBEC3G/F). Under steady state HERV-K genes are not expressed, believed to be the function of suppression mediated in part by APOBEC3G/F. However, in various cancers, upon HIV infection, and other specialized cellular activation methods HERV-K genes are expressed. HERV-K Env expression is activated by malignant transformation, and its expression has been reported in germ cell tumors, melanoma, breast cancer, ovarian cancer, prostate cancer, leukemia and lymphoma.

HERV-K expression has been demonstrated to be induced upon HIV infection in vitro, and the expression of HERV-K Envelope (Env) on the surface of HIV-infected cells. This is the consequence of HIV Tat and Vif proteins. As HIV acquires host cell membrane proteins through the budding process it has suggested, although not yet demonstrated that HERVK Env may also be present on surface of HIV virions. Serum antibodies and T cell responses against HERV-K have been detected in HIV infected patients and SIV infected rhesus macaques. It has been demonstrated that HERV-K (HML-2) transmembrane (TM) domain is expressed on the surface of HIV-1-infected cells. The antibodies against human HERV-K (HML-2) transmembrane protein/domain bind specifically to HIV-1-infected cells and eliminated these infected cells in vitro through an antibody-dependent cell-mediated cytotoxicity (ADCC) mechanism.

SUMMARY OF THE INVENTION

In one aspect, the present invention provides an isolated antibody or an antigen-binding portion thereof that specifically binds to human HERV-K envelope polypeptide. In one embodiment, the antibody is monoclonal antibody. In one embodiment, the anti-human HERV-K envelope polypeptide antibody binds to the human HERV-K envelope polypeptide expressed on the surface of cells infected with HIV virus and the binding triggers immune response that inhibits the HIV infectivity or eliminates the HIV-infected cells. In some embodiments, the antibody or antigen-binding portion thereof is a monoclonal antibody. In some embodiments, the antibody is a recombinant antibody. In some embodiments, the antibody comprises KSN-01, KSN-02, or KSN-03. In some embodiments, the antigen-binding portion thereof comprises the variable heavy and/or light chains of KSN-01, KSN-02, or KSN-03. In some embodiments, the antibody or antigen-binding portion thereof comprises one of an IgG, e.g. IgG1, IgG2, IgG3, IgG4, IgA, IgD, IgE, or IgM isotype. In some embodiments, the antibody is an isotype-switched antibody. In exemplary embodiments, KSN-01, KSN-02, and KSN-03 comprise IgG isotype, e.g. IgG1.

In some embodiments, the antibody or the antigen-binding portion thereof specifically binds to the surface unit (SU) domain of the human HERV-K envelope polypeptide. In some embodiments+, the antibody or the antigen-binding portion thereof specifically binds to the transmembrane I domain of the human HERV-K envelope polypeptide.

In some embodiments, the antibody or antigen-binding portion thereof has a variable heavy chain region comprising SEQ ID NO: 23. In some embodiments, the variable heavy chain region has at least 75% homology with SEQ ID NO: 23. In some embodiments, the variable heavy chain region has at least 80% homology with SEQ ID NO: 23. In some embodiments, the variable heavy chain region has at least 85% homology with SEQ ID NO: 23. In some embodiments, the variable heavy chain region has at least 90% homology with SEQ ID NO: 23. In some embodiments, the variable heavy chain region has at least 95% homology with SEQ ID NO: 23. In some embodiments, the variable heavy chain region has more than 95% homology with SEQ ID NO: 23. In some embodiments, SEQ ID NO: 23 has at least one conservative substitution.

In some embodiments, the antibody or antigen-binding portion thereof has a variable heavy chain region comprising SEQ ID NO: 25. In some embodiments, the variable heavy chain region has at least 75% homology with SEQ ID NO: 25. In some embodiments, the variable heavy chain region has at least 80% homology with SEQ ID NO: 25. In some embodiments, the variable heavy chain region has at least 85% homology with SEQ ID NO: 25. In some embodiments, the variable heavy chain region has at least 90% homology with SEQ ID NO: 25. In some embodiments, the variable heavy chain region has at least 95% homology with SEQ ID NO: 25. In some embodiments, the variable heavy chain region has more than 95% homology with SEQ ID NO: 25. In some embodiments, SEQ ID NO: 25 has at least one conservative substitution.

In some embodiments, the antibody or antigen-binding portion thereof has a variable heavy chain region comprising SEQ ID NO: 27. In some embodiments, the variable heavy chain region has at least 75% homology with SEQ ID NO: 27. In some embodiments, the variable heavy chain region has at least 80% homology with SEQ ID NO: 27. In some embodiments, the variable heavy chain region has at least 85% homology with SEQ ID NO: 27. In some embodiments, the variable heavy chain region has at least 90% homology with SEQ ID NO: 27. In some embodiments, the variable heavy chain region has at least 95% homology with SEQ ID NO: 27. In some embodiments, the variable heavy chain region has more than 95% homology with SEQ ID NO: 27. In some embodiments, SEQ ID NO: 27 has at least one conservative substitution.

In some embodiments, the antibody or antigen-binding portion thereof has a variable light chain region comprising SEQ ID NO: 22. In some embodiments, the variable light chain region has at least 75% homology with SEQ ID NO: 22. In some embodiments, the variable light chain region has at least 80% homology with SEQ ID NO: 22. In some embodiments, the variable light chain region has at least 85% homology with SEQ ID NO: 22. In some embodiments, the variable light chain region has at least 90% homology with SEQ ID NO: 22. In some embodiments, the variable light chain region has at least 95% homology with SEQ ID NO: 22. In some embodiments, the variable light chain region has more than 95% homology with SEQ ID NO: 22. In some embodiments, SEQ ID NO: 22 has at least one conservative substitution.

In some embodiments, the antibody or antigen-binding portion thereof has a variable light chain region comprising SEQ ID NO: 24. In some embodiments, the variable light chain region has at least 75% homology with SEQ ID NO: 24. In some embodiments, the variable light chain region has at least 80% homology with SEQ ID NO: 24. In some embodiments, the variable light chain region has at least 85% homology with SEQ ID NO: 24. In some embodiments, the variable light chain region has at least 90% homology with SEQ ID NO: 24. In some embodiments, the variable light chain region has at least 95% homology with SEQ ID NO: 24. In some embodiments, the variable light chain region has more than 95% homology with SEQ ID NO: 24. In some embodiments, SEQ ID NO: 24 has at least one conservative substitution.

In some embodiments, the antibody or antigen-binding portion thereof has a variable light chain region comprising SEQ ID NO: 26. In some embodiments, the variable light chain region has at least 75% homology with SEQ ID NO: 26. In some embodiments, the variable light chain region has at least 80% homology with SEQ ID NO: 26. In some embodiments, the variable light chain region has at least 85% homology with SEQ ID NO: 26. In some embodiments, the variable light chain region has at least 90% homology with SEQ ID NO: 26. In some embodiments, the variable light chain region has at least 95% homology with SEQ ID NO: 26. In some embodiments, the variable light chain region has more than 95% homology with SEQ ID NO: 26. In some embodiments, SEQ ID NO: 26 has at least one conservative substitution.

In some embodiments, the antibody or antigen-binding portion thereof has one or more complementarity-determining regions of the variable heavy chain region (HCDRs) comprising one or more of SEQ ID NO: 4, SEQ ID NO: 5, and SEQ ID NO: 6. In some embodiments, one or more of the CDRs of the variable heavy chain region has at least 75% homology with one or more of SEQ ID NO: 4, SEQ ID NO: 5, and SEQ ID NO: 6. In some embodiments, one or more of the CDRs of the variable heavy chain region has at least 80% homology with one or more of SEQ ID NO: 4, SEQ ID NO: 5, and SEQ ID NO: 6. In some embodiments, one or more of the CDRs of the variable heavy chain region has at least 85% homology with one or more of SEQ ID NO: 4, SEQ ID NO: 5, and SEQ ID NO: 6. In some embodiments, one or more of the CDRs of the variable heavy chain region has at least 90% homology with one or more of SEQ ID NO: 4, SEQ ID NO: 5, and SEQ ID NO: 6. In some embodiments, one or more of the CDRs of the variable heavy chain region has at least 95% homology with one or more of SEQ ID NO: 4, SEQ ID NO: 5, and SEQ ID NO: 6. In some embodiments, one or more of the CDRs of the variable heavy chain region has more than 95% homology one or more of SEQ ID NO: 4, SEQ ID NO: 5, and SEQ ID NO: 6. In some embodiments, one or more of SEQ ID NO: 4, SEQ ID NO: 5, and SEQ ID NO: 6 has at least one conservative substitution.

In some embodiments, the antibody or antigen-binding portion thereof has one or more complementarity-determining regions of the variable heavy chain region (HCDRs) comprising one or more of SEQ ID NO: 10, SEQ ID NO: 11, and SEQ ID NO: 12. In some embodiments, one or more of the CDRs of the variable heavy chain region has at least 75% homology with one or more of SEQ ID NO: 10, SEQ ID NO: 11, and SEQ ID NO: 12. In some embodiments, one or more of the CDRs of the variable heavy chain region has at least 80% homology with one or more of SEQ ID NO: 10, SEQ ID NO: 11, and SEQ ID NO: 12. In some embodiments, one or more of the CDRs of the variable heavy chain region has at least 85% homology with one or more of SEQ ID NO: 10, SEQ ID NO: 11, and SEQ ID NO: 12. In some embodiments, one or more of the CDRs of the variable heavy chain region has at least 90% homology with one or more of SEQ ID NO: 10, SEQ ID NO: 11, and SEQ ID NO: 12. In some embodiments, one or more of the CDRs of the variable heavy chain region has at least 95% homology with one or more of SEQ ID NO: 10, SEQ ID NO: 11, and SEQ ID NO: 12. In some embodiments, one or more of the CDRs of the variable heavy chain region has more than 95% homology one or more of SEQ ID NO: 10, SEQ ID NO: 11, and SEQ ID NO: 12. In some embodiments, one or more of SEQ ID NO: 10, SEQ ID NO: 11, and SEQ ID NO: 12 has at least one conservative substitution.

In some embodiments, the antibody or antigen-binding portion thereof has one or more complementarity-determining regions of the variable heavy chain region (HCDRs) comprising one or more of SEQ ID NO: 16, SEQ ID NO: 17, and SEQ ID NO: 18. In some embodiments, one or more of the CDRs of the variable heavy chain region has at least 75% homology with one or more of SEQ ID NO: 16, SEQ ID NO: 17, and SEQ ID NO: 18. In some embodiments, one or more of the CDRs of the variable heavy chain region has at least 80% homology with one or more of SEQ ID NO: 16, SEQ ID NO: 17, and SEQ ID NO: 18. In some embodiments, one or more of the CDRs of the variable heavy chain region has at least 85% homology with one or more of SEQ ID NO: 16, SEQ ID NO: 17, and SEQ ID NO: 18. In some embodiments, one or more of the CDRs of the variable heavy chain region has at least 90% homology with one or more of SEQ ID NO: 16, SEQ ID NO: 17, and SEQ ID NO: 18. In some embodiments, one or more of the CDRs of the variable heavy chain region has at least 95% homology with one or more of SEQ ID NO: 16, SEQ ID NO: 17, and SEQ ID NO: 18. In some embodiments, one or more of the CDRs of the variable heavy chain region has more than 95% homology one or more of SEQ ID NO: 16, SEQ ID NO: 17, and SEQ ID NO: 18. In some embodiments, one or more of SEQ ID NO: 16, SEQ ID NO: 17, and SEQ ID NO: 18 has at least one conservative substitution.

In some embodiments, the antibody or antigen-binding portion thereof has one or more complementarity-determining regions of the variable light chain region (LDCRs) comprising one or more of SEQ ID NO: 7, SEQ ID NO: 8, and SEQ ID NO: 9. In some embodiments, one or more of the CDRs of the variable light chain region has at least 75% homology with one or more of SEQ ID NO: 7, SEQ ID NO: 8, and SEQ ID NO: 9. In some embodiments, one or more of the CDRs of the variable light chain region has at least 80% homology one or more of SEQ ID NO: 7, SEQ ID NO: 8, and SEQ ID NO: 9. In some embodiments, one or more of the CDRs of the variable light chain region has at least 85% homology with one or more of SEQ ID NO: 7, SEQ ID NO: 8, and SEQ ID NO: 9. In some embodiments, one or more of the CDRs of the variable light chain region has at least 90% homology with one or more of SEQ ID NO: 7, SEQ ID NO: 8, and SEQ ID NO: 9. In some embodiments, one or more of the CDRs of the variable light chain region has at least 95% homology with one or more of SEQ ID NO: 7, SEQ ID NO: 8, and SEQ ID NO: 9. In some embodiments, one or more of the CDRs of the variable light chain region has more than 95% homology with one or more of SEQ ID NO: 7, SEQ ID NO: 8, and SEQ ID NO: 9. In some embodiments, one or more of SEQ ID NO: 7, SEQ ID NO: 8, and SEQ ID NO: 9 has at least one conservative substitution.

In some embodiments, the antibody or antigen-binding portion thereof has one or more complementarity-determining regions of the variable light chain region (LDCRs) comprising one or more of SEQ ID NO: 13, SEQ ID NO: 14, and SEQ ID NO: 15. In some embodiments, one or more of the CDRs of the variable light chain region has at least 75% homology with one or more of SEQ ID NO: 13, SEQ ID NO: 14, and SEQ ID NO: 15. In some embodiments, one or more of the CDRs of the variable light chain region has at least 80% homology one or more of SEQ ID NO: 13, SEQ ID NO: 14, and SEQ ID NO: 15. In some embodiments, one or more of the CDRs of the variable light chain region has at least 85% homology with one or more of SEQ ID NO: 13, SEQ ID NO: 14, and SEQ ID NO: 15. In some embodiments, one or more of the CDRs of the variable light chain region has at least 90% homology with one or more of SEQ ID NO: 13, SEQ ID NO: 14, and SEQ ID NO: 15. In some embodiments, one or more of the CDRs of the variable light chain region has at least 95% homology with one or more of SEQ ID NO: 13, SEQ ID NO: 14, and SEQ ID NO: 15. In some embodiments, one or more of the CDRs of the variable light chain region has more than 95% homology with one or more of SEQ ID NO: 13, SEQ ID NO: 14, and SEQ ID NO: 15. In some embodiments, one or more of SEQ ID NO: 13, SEQ ID NO: 14, and SEQ ID NO: 15 has at least one conservative substitution.

In some embodiments, the antibody or antigen-binding portion thereof has one or more complementarity-determining regions of the variable light chain region (LDCRs) comprising one or more of SEQ ID NO: 19, SEQ ID NO: 20, and SEQ ID NO: 21. In some embodiments, one or more of the CDRs of the variable light chain region has at least 75% homology with one or more of SEQ ID NO: 19, SEQ ID NO: 20, and SEQ ID NO: 21. In some embodiments, one or more of the CDRs of the variable light chain region has at least 80% homology one or more of SEQ ID NO: 19, SEQ ID NO: 20, and SEQ ID NO: 21. In some embodiments, one or more of the CDRs of the variable light chain region has at least 85% homology with one or more of SEQ ID NO: 19, SEQ ID NO: 20, and SEQ ID NO: 21. In some embodiments, one or more of the CDRs of the variable light chain region has at least 90% homology with one or more of SEQ ID NO: 19, SEQ ID NO: 20, and SEQ ID NO: 21. In some embodiments, one or more of the CDRs of the variable light chain region has at least 95% homology with one or more of SEQ ID NO: 19, SEQ ID NO: 20, and SEQ ID NO: 21. In some embodiments, one or more of the CDRs of the variable light chain region has more than 95% homology with one or more of SEQ ID NO: 19, SEQ ID NO: 20, and SEQ ID NO: 21. In some embodiments, one or more of SEQ ID NO: 19, SEQ ID NO: 20, and SEQ ID NO: 21 has at least one conservative substitution.

In some embodiments, the antibody or antigen-binding portion thereof has at least one complementarity determining region (CDR) having a sequence selected from the group consisting of SEQ ID NOs: 4-21, or a sequence consisting essentially of one of SEQ ID NOs: 4-21 but having at least one conservative substitution. In some embodiments, the antibody or antigen-binding portion thereof has a heavy chain variable region that comprises HCDR1, HCDR2, and HCDR3, wherein the HCDR1, HCDR2, and HCDR3 comprise the respective sequences of an HCDR set selected from the group consisting of SEQ ID NOs: 4-6, 10-12, and 16-18 and sequences consisting essentially of SEQ ID NOs: 4-6, 10-12, and 16-18 but having at least one conservative substitution. In some embodiments, the antibody or antigen-binding portion thereof has a light chain variable region that comprises LCDR1, LCDR2, and LCDR3, wherein the LCDR1, LCDR2 and LCDR3 comprise the respective sequences of a LCDR set selected from the group consisting of SEQ ID NOs: 7-9, 13-15, and 19-21 and sequences consisting essentially of SEQ ID NOs: 7-9, 13-15, and 19-21 but having at least one conservative substitution. In some embodiments, the antibody or antigen-binding portion thereof has a heavy chain variable region that comprises HCDR1, HCDR2, and HCDR3, and a light chain variable region that comprises LCDR1, LCDR2, and LCDR3, wherein the HCDR1, HCDR2, HCDR3, LCDR1, LCDR2 and LCDR3 comprise the respective sequences of a CDR set selected from the group consisting of SEQ ID NOs: 4-9, 10-15, and 16-21, and sequences consisting essentially of SEQ ID NOs: 4-9, 10-15, and 16-21 but having at least one conservative substitution.

In some embodiments, the antibody or antigen-binding portion thereof comprises one or both of (i) a heavy chain comprising a sequence selected from the group consisting of SEQ ID NOs: 23, 25 and 27, or a sequence consisting essentially of SEQ ID NOs: of 23, 25, and 27 but having at least one conservative substitution, and (ii) a light chain comprising a sequence selected from the group consisting of SEQ ID NOs: 22, 24, and 26, or a sequence consisting essentially of SEQ ID NOs: of 22, 24, and 26 but having at least one conservative substitution. In some embodiments, the light chain and the heavy chain comprise the respective sequences of SEQ ID NOs: 22-23; SEQ ID NOs: 24-25; and SEQ ID NOs: 26-27, or sequences consisting essentially of SEQ ID NOs: 22-23; SEQ ID NOs: 24-25; and SEQ ID NOs: 26-27, but having at least one conservative substitution.

In some embodiments, the antibody or the antigen-binding portion thereof specifically binds to the surface unit domain of the human HERV-K envelope polypeptide and comprises a heavy chain variable region comprising a HCDR1 comprising an amino acid sequence of SEQ ID NO: 4, a HCDR2 comprising an amino acid sequence of SEQ ID NO: 5 and a HCDR3 comprising an amino acid sequence of SEQ ID NO: 6; and a light chain variable region comprising a LCDR1 comprising an amino acid sequence of SEQ ID NO: 7, a LCDR2 comprising an amino acid sequence of SEQ ID NO: 8 and a LCDR3 comprising an amino acid sequence of SEQ ID NO: 9.

In some embodiments, the antibody or the antigen-binding portion thereof specifically binds to the surface unit domain of the human HERV-K envelope polypeptide and comprises a heavy chain variable region comprising amino acid sequence of SEQ ID NO: 23 and light chain variable region comprises an amino acid sequence of SEQ ID NO: 22.

In some embodiments, the antibody or the antigen-binding portion thereof specifically binds to the surface unit (SU) domain of the human HERV-K envelope polypeptide and comprises a heavy chain variable region comprising a HCDR1 comprising an amino acid sequence of SEQ ID NO: 10, a HCDR2 comprising an amino acid sequence of SEQ ID NO: 11 and a HCDR3 comprising an amino acid sequence of SEQ ID NO: 12; and a light chain variable region comprising a LCDR1 comprising an amino acid sequence of SEQ ID NO: 13, a LCDR2 comprising an amino acid sequence of SEQ ID NO: 14 and a LCDR3 comprising an amino acid sequence of SEQ ID NO: 15.

In some embodiments, the antibody or the antigen-binding portion thereof specifically binds to the surface unit (SU) domain of the human HERV-K envelope polypeptide and comprises a heavy chain variable region comprising amino acid sequence of SEQ ID NO: 25 and light chain variable region comprises an amino acid sequence of SEQ ID NO: 24.

In some embodiments, the antibody or the antigen-binding portion thereof specifically binds to the transmembrane I domain of the human HERV-K envelope polypeptide and comprises a heavy chain variable region comprising a HCDR1 comprising an amino acid sequence of SEQ ID NO: 16, a HCDR2 comprising an amino acid sequence of SEQ ID NO: 17 and a HCDR3 comprising an amino acid sequence of SEQ ID NO: 18; and a light chain variable region comprising a LCDR1 comprising an amino acid sequence of SEQ ID NO: 19, a LCDR2 comprising an amino acid sequence of SEQ ID NO: 20 and a LCDR3 comprising an amino acid sequence of SEQ ID NO: 21.

In some embodiments, the antibody or the antigen-binding portion thereof specifically binds to the transmembrane I domain of the human HERV-K envelope polypeptide and comprises a heavy chain variable region comprising amino acid sequence of SEQ ID NO: 27 and light chain variable region comprises an amino acid sequence of SEQ ID NO: 26.

In some embodiments, the antibodies of the present invention described herein comprise one or more non-naturally occurring amino acids. In one embodiment, the non-naturally encoded amino acid comprises a carbonyl group, an acetyl group, an aminooxy group, a hydrazine group, a hydrazide group, a semicarbazide group, an azide group, or an alkyne group. See e.g., U.S. Pat. No. 7,632,924 for suitable non-naturally occurring amino acids. Inclusion of a non-naturally occurring amino acid can provide for linkage to a polymer, a second polypeptide, a scaffold, etc.

The present invention also provides antibodies that compete for binding to HERV-K envelope polypeptide (either SU or TM domain) with the particular antibodies described herein (e.g., antibodies KSN-01, KSN-02 and KSN-03). Such antibodies can be identified based on their ability to competitively inhibit binding to HERV-K envelope polypeptide of one or more monoclonal antibodies KSN-01, KSN-02 and KSN-03 in standard antibody binding assays.

In certain embodiments, the anti-HERV-K Env antibodies binds to the same epitope on the human HERV-K envelope polypeptide that is recognized by the particular antibodies described herein (e.g., antibodies KSN-01, KSN-02 and KSN-03).

Yet in certain embodiments, the anti-HERV-K Env antibodies as described herein are human or chimeric antibodies. In some embodiments, the anti-HERV-K Env antibodies or antigen-binding portions thereof as described herein are recombinantly produced. In some embodiments, the anti-HERV-K Env antibodies or antigen-binding portions thereof as described herein are recombinantly produced in a prokaryote. In some embodiments, the anti-HERV-K Env antibodies or antigen-binding portions thereof as described herein are recombinantly produced in a eukaryote. In some embodiments, the anti-HERV-K Env antibodies or antigen-binding portions thereof as described herein are recombinantly produced in a yeast cell. In some embodiments, the anti-HERV-K Env antibodies or antigen-binding portions thereof as described herein are recombinantly produced in a Chinese hamster ovary (CHO) cell. In some embodiments, the anti-HERV-K Env antibodies or antigen-binding portions thereof as described herein are recombinantly produced in a HEK293 cell.

One embodiment described herein pertains to an isolated monoclonal antibody or antigen-binding portion thereof comprising a heavy chain variable region comprising CDR1, CDR2 and CDR3 sequences comprising an amino acid sequence selected from the group consisting of SEQ ID NOs: 4, 5, 6, 10, 11, 12, 16, 17 and 18 respectively, and a light chain variable region comprising CDR1, CDR2 and CDR3 sequences comprising an amino acid sequence selected from the group consisting of SEQ ID NOs: 7, 8, 9, 13, 14, 15, 19, 20 and 21 respectively. Thus, such antibodies contain the heavy chain variable region and light chain variable region CDR sequences of monoclonal antibodies KSN-01, KSN-02 and KSN-03, yet contain different framework sequences from these antibodies.

In certain embodiments, the antibody variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g., one or more chemical moieties can be attached to the antibody) or be modified to alter its glycosylation, to alter one or more functional properties of the antibody. The numbering of residues in the Fc region is that of the EU index of Kabat.

In still another embodiment, the glycosylation of an antibody is modified.

Another modification of the antibodies described herein is pegylation. An antibody can be pegylated to, for example, increase the biological (e.g., serum) half-life of the antibody.

The present invention also encompasses a human monoclonal antibody described herein conjugated to a therapeutic agent, a polymer, a detectable label or enzyme. In one embodiment, the therapeutic agent is a cytotoxic agent. In one embodiment, the polymer is polyethylene glycol (PEG).

In another aspect, the present invention provides a pharmaceutical composition comprising the antibodies of the present invention described herein formulated together with a pharmaceutically acceptable carrier. The composition may optionally contain one or more additional pharmaceutically active ingredients, such as another antibody or a therapeutic agent. The pharmaceutical compositions of the invention also can be administered in a combination therapy with, for example, another immune-stimulatory agent, anti-cancer agent, an antiviral agent, or a vaccine, etc. In certain embodiments, a composition comprises an anti-HERV-K Env antibody at a concentration of at least 1 mg/Ml, 5 mg/mL, 10 mg/mL, 50 mg/mL, 100 mg/mL, 150 mg/mL, 200 mg/mL, 1-300 mg/mL, or 100-300 mg/mL.

In another aspect, the present disclosure is directed to nucleic acid sequences encoding the heavy and/or light chains of one or more anti-HERV-K antibodies of the present disclosure. In some embodiments, the nucleic acids have conservative substitutions. In some embodiments, the nucleic acids are codon optimized.

In some embodiments, the nucleic acid sequence comprises SEQ ID NO: 28. In some embodiments, the nucleic acid sequence has at least 75% homology with SEQ ID NO: 28. In some embodiments, the nucleic acid sequence has at least 80% homology with SEQ ID NO: 28. In some embodiments, the nucleic acid sequence has at least 85% homology with SEQ ID NO: 28. In some embodiments, the nucleic acid sequence has at least 90% homology with SEQ ID NO: 28. In some embodiments, the nucleic acid sequence has at least 95% homology with SEQ ID NO: 28. In some embodiments, the nucleic acid sequence has more than 95% homology with SEQ ID NO: 28. In some embodiments, SEQ ID NO: 28 is codon optimized.

In some embodiments, the nucleic acid sequence comprises SEQ ID NO: 29. In some embodiments, the nucleic acid sequence has at least 75% homology with SEQ ID NO: 29. In some embodiments, the nucleic acid sequence has at least 80% homology with SEQ ID NO: 29. In some embodiments, the nucleic acid sequence has at least 85% homology with SEQ ID NO: 29. In some embodiments, the nucleic acid sequence has at least 90% homology with SEQ ID NO: 29. In some embodiments, the nucleic acid sequence has at least 95% homology with SEQ ID NO: 29. In some embodiments, the nucleic acid sequence has more than 95% homology with SEQ ID NO: 29. In some embodiments, SEQ ID NO: 29 is codon optimized.

In some embodiments, the nucleic acid sequence comprises SEQ ID NO: 30. In some embodiments, the nucleic acid sequence has at least 75% homology with SEQ ID NO: 30. In some embodiments, the nucleic acid sequence has at least 80% homology with SEQ ID NO: 30. In some embodiments, the nucleic acid sequence has at least 85% homology with SEQ ID NO: 30. In some embodiments, the nucleic acid sequence has at least 90% homology with SEQ ID NO: 30. In some embodiments, the nucleic acid sequence has at least 95% homology with SEQ ID NO: 30. In some embodiments, the nucleic acid sequence has more than 95% homology with SEQ ID NO: 30. In some embodiments, SEQ ID NO: 30 is codon optimized.

In some embodiments, the nucleic acid sequence comprises SEQ ID NO: 31. In some embodiments, the nucleic acid sequence has at least 75% homology with SEQ ID NO: 31. In some embodiments, the nucleic acid sequence has at least 80% homology with SEQ ID NO: 31. In some embodiments, the nucleic acid sequence has at least 85% homology with SEQ ID NO: 31. In some embodiments, the nucleic acid sequence has at least 90% homology with SEQ ID NO: 31. In some embodiments, the nucleic acid sequence has at least 95% homology with SEQ ID NO: 31. In some embodiments, the nucleic acid sequence has more than 95% homology with SEQ ID NO: 31. In some embodiments, SEQ ID NO: 31 is codon optimized.

In some embodiments, the nucleic acid sequence comprises SEQ ID NO: 32. In some embodiments, the nucleic acid sequence has at least 75% homology with SEQ ID NO: 32. In some embodiments, the nucleic acid sequence has at least 80% homology with SEQ ID NO: 32. In some embodiments, the nucleic acid sequence has at least 85% homology with SEQ ID NO: 32. In some embodiments, the nucleic acid sequence has at least 90% homology with SEQ ID NO: 32. In some embodiments, the nucleic acid sequence has at least 95% homology with SEQ ID NO: 32. In some embodiments, the nucleic acid sequence has more than 95% homology with SEQ ID NO: 32. In some embodiments, SEQ ID NO: 32 is codon optimized.

In some embodiments, the nucleic acid sequence comprises SEQ ID NO: 33. In some embodiments, the nucleic acid sequence has at least 75% homology with SEQ ID NO: 33. In some embodiments, the nucleic acid sequence has at least 80% homology with SEQ ID NO: 33. In some embodiments, the nucleic acid sequence has at least 85% homology with SEQ ID NO: 33. In some embodiments, the nucleic acid sequence has at least 90% homology with SEQ ID NO: 33. In some embodiments, the nucleic acid sequence has at least 95% homology with SEQ ID NO: 33. In some embodiments, the nucleic acid sequence has more than 95% homology with SEQ ID NO: 33. In some embodiments, SEQ ID NO: 33 is codon optimized.

In another aspect, the present disclosure is directed to a vector or a system of vectors. In some embodiments, the vector or vector system comprises a nucleic acid sequence coding for a variable heavy chain region and a nucleic acid sequence coding for a variable light chain region. In some embodiments, the nucleic acid sequence is any nucleic acid sequence according to the present disclosure. In some embodiments, a nucleic acid sequence coding for a heavy chain is on the same vector as a nucleic acid sequence coding for a light chain. In some embodiments, a nucleic acid sequence coding for a variable heavy chain region is on a different vector than a nucleic acid sequence coding for a variable light chain region. In some embodiments, the vector or system of vectors is a plasmid or plasmids. In some embodiments, the vector or a system of vectors is a phage vector or vectors. In some embodiments, the phage vector is a γ phage. In some embodiments, the vector or vectors is a cosmid or cosmids. In some embodiments, the vector or system of vectors is a recombinant chromosome or recombinant chromosomes. In some embodiments, the vector system is a combination of different vectors. In some embodiments, expression of the different nucleic acid sequences may be concomitant. In other embodiments, expression of the different nucleic acid sequences may be separately inducible. In another embodiment, the present disclosure is directed to a vector or system of vectors containing one or more nucleic acid sequences encoding one or more complementarity determining regions (CDRs) of one or more heavy and/or light chains of one or more of the anti-HERV-K antibodies of the present disclosure. In some embodiments, the vector or system of vectors comprises an allele encoding an immunoglobulin constant region. In some embodiments the immunoglobulin constant region comprises an IgG (e.g. IgG1, IgG2, IgG3, IgG4) constant region. In exemplary embodiments, the immunoglobulin constant region comprises an IgG1 constant region.

In some embodiments, the present invention is directed to a cell transformed with a vector or vector system of the present disclosure. In some embodiments, the cell is a bacterial cell, a yeast cell, a plant cell, or a mammalian cell. In some embodiments, the mammalian cell is one of a Chinese hamster ovary (CHO) cell, including DUXB11, DG44 and CHOK1 lineages, a NS0 murine myeloma cell, a PER.C6 cell, and a human embryonic kidney (HEK) cell, including HEK293 lineages.

In another aspect, the anti-HERV-K Env antibodies described herein can be used to neutralize HIV virus. The neutralizing of the HIV virus can be done via (i) inhibiting HIV virus binding to a target cell; (ii) inhibiting HIV virus uptake by a target cell; (iii) inhibiting HIV virus replication; and (iv) inhibiting HIV virus particles release from infected cells.

Another aspect of the present invention provides a method of treating a HIV-based disease. Such method includes therapeutic (following HIV infection) and prophylactic (prior to HIV exposure, infection or pathology). In some embodiments, a method of treating a HIV-based disease comprises administering to an individual in need thereof an anti-HERV-K Env antibody or therapeutic composition disclosed herein in an amount sufficient to reduce one or more physiological conditions or symptom associated with a HIV infection or pathology, thereby treating the HIV-based disease. In some embodiments, the method of treating an HIV infection includes administering to an individual having, or suspected of having, an HIV infection at least one anti-HERV-K antibody or antigen-binding portion thereof. In some embodiments, the method further includes the step of identifying an individual as having an HIV infection prior to the administering step. In some embodiments, the method further includes administration of at least one additional anti-HERV-K antibody or antigen-binding portion thereof. In some embodiments, the method further includes administration of an antiviral. In some embodiments, the antiviral comprises one of a reverse transcriptase inhibitor, a protease inhibitor, an entry inhibitor, an integrase inhibitor, a maturation inhibitor, an assembly inhibitor, or a combination thereof. In some embodiments, the method further includes administration of a pharmaceutically acceptable excipient, carrier, or preservative. In some embodiments, the additional anti-HERV-K antibody or antigen-binding portion thereof may be co-administered with the anti-HERV-K antibody or antibodies or antigen-binding portion(s) thereof and/or antiviral or antivirals. In other embodiments, the anti-HERV-K antibody or antigen-binding portion thereof is administered prior to the additional anti-HERV-K antibody or antibodies or antigen-binding portion(s) thereof and/or antiviral or antivirals. In yet other embodiments, the anti-HERV-K antibody or antigen-binding portion thereof is administered after the additional anti-HERV-K antibody or antibodies or antigen-binding portion(s) thereof and/or antiviral or antivirals. And in yet even other embodiments, the anti-HERV-K antibody or antigen-binding portion thereof may be administered in between additional anti-HERV-K antibodies or antigen-binding portion(s) thereof and/or antiviral or antivirals.

In other embodiments, the anti-HERV-K antibody or antigen-binding portions are administered with one or more additional anti-HIV antibodies or antigen-binding portions thereof. In some embodiments, the additional anti-HIV antibody or antigen-binding portion thereof may be co-administered with the anti-HERV-K antibody or antibodies or antigen-binding portion(s) thereof and/or antiviral or antivirals. In other embodiments, the anti-HERV-K antibody or antigen-binding portion thereof is administered prior to the additional anti-HIV antibody or antibodies or antigen-binding portion(s) thereof and/or antiviral or antivirals. In yet other embodiments, the anti-HERV-K antibody or antigen-binding portion thereof is administered after the additional anti-HIV antibody or antibodies or antigen-binding portion(s) thereof and/or antiviral or antivirals. And in yet even other embodiments, the anti-HERV-K antibody or antigen-binding portion thereof may be administered in between additional anti-HIV antibodies or antigen-binding portion(s) thereof and/or antiviral or antivirals.

In another aspect, the present disclosure is directed to a passive vaccine. In some embodiments, the vaccine includes at least one anti-HERV-K antibody or antigen-binding portion thereof. In some embodiments, the at least one anti-HERV-K antibody or antigen-binding portion thereof is any anti-HERV-K antibody or antigen-binding portion thereof of the present disclosure. In some embodiments, the passive vaccine further includes a pharmaceutically acceptable excipient.

In another aspect, the present disclosure is directed to a method of preventing an HIV infection in an individual in need thereof. In some embodiments, the method includes administering to an individual a passive vaccine composition containing least one anti-HERV-K antibody or antigen-binding portion thereof. In some embodiments, the at least one anti-HERV-K antibody or antigen-binding portion thereof is any anti-HERV-K antibody or antigen-binding portion thereof of the present disclosure. In some embodiments, the passive vaccine further includes a pharmaceutically acceptable excipient.

In another aspect, the present disclosure is directed to a method of treating or preventing a cellular proliferative disorder in an individual in need thereof. In some embodiments, the cellular proliferative disorder comprises a cancer. In some embodiments, the cancer comprises at least one of pancreatic cancer, breast cancer, melanoma, hepatocellular carcinoma, ovarian cancer, leukemia, lymphoma, germ cell tumors, prostate cancer, and combinations thereof. In some embodiments, the method comprises administering to said subject at least one anti-HERV-K antibody or antigen-binding portion thereof according to any aspect of the present disclosure. In some embodiments, the method further includes the step of identifying an individual as having the cellular proliferative disorder prior to the administering step. In some embodiments, the method further comprises administering a chemotherapeutic agent to said subject. In some embodiments, the method comprises administering to said subject a composition comprising at least one anti-HERV-K antibody or antigen-binding portion thereof conjugated to the chemotherapeutic agent. In some embodiments, the chemotherapeutic agent comprises at least one of an alkylating agent, a taxane, epothilone, histone deacetylase inhibitor, topoisomerase I/II inhibitor, kinase inhibitor, nucleotide analog, platinum-based agents, vinca alkaloids and derivatives thereof, cytotoxic agents, peptide based compositions, radionuclides, and combinations thereof.

In another aspect, the present disclosure is directed to a method of treating an autoimmune, neurological, or metabolic related disorder in a subject in need thereof. In some embodiments, the disorder comprises at least one of rheumatoid arthritis (RA), systemic lupus erythematosus (SLE), psoriasis, morphea, multiple sclerosis (MS), myalgic encephalomyelitis, amyotrophic lateral sclerosis (ALS), and combinations thereof. In some embodiments, the method comprises administering to said subject at least one anti-HERV-K antibody or antigen-binding portion thereof according to any aspect of the present disclosure. In some embodiments, the method further includes the step of identifying an individual as having the autoimmune, neurological, or metabolic related disorder prior to the administering step. In some embodiments, the method further comprises administering an immunosuppressive agent to said subject.

In another aspect of the present invention, the anti-HERV-K Env antibody described herein can be used in various detection methods, for use in, e.g., monitoring the progression of an immunodeficiency virus infection; monitoring patient response to treatment for an immunodeficiency virus infection, etc. The present disclosure provides methods of detecting a HERV-K envelope polypeptide in a biological sample obtained from an individual. The methods generally involve: a) contacting the biological sample with a subject anti-HERV-K antibody; and b) detecting binding, if any, of the antibody to an epitope present in the sample.

In some embodiments, the present disclosure is directed to kits containing a first antibody or antigen-binding portion thereof that specifically binds to HERV-K or an antigenic fragment thereof, e.g. TM or SU domains of HERV-K. In some embodiments, the kits contain a second antibody. In some embodiments, the second antibody or antigen-binding portion thereof specifically binds to HERV-K or an antigenic fragment thereof. In other embodiments, the second antibody or antigen-binding portion thereof specifically binds to the first antibody or antigen-binding portion thereof. In some embodiments, the first antibody or antigen-binding portion thereof is a monoclonal antibody. In some embodiments, the second antibody or antigen-binding portion thereof is a monoclonal antibody. In some embodiments, at least one of the first antibody or antigen-binding portion thereof and the second antibody or antigen-binding portion thereof are monoclonal antibodies. In some embodiments, neither of the first antibody or antigen-binding portion thereof and the second antibody or antigen-binding portion thereof are monoclonal antibodies. In some embodiments, at least one of the first antibody or antigen-binding portion thereof and the second antibody or antigen-binding portion thereof are recombinant antibodies. In some embodiments, the anti-HERV-K antibody or antigen-binding portion thereof comprises one of KSN-01, KSN-02, or KSN-03.

In some embodiments, the first antibody or antigen-binding portion thereof is bound to a substrate. In some embodiments, the second antibody or antigen-binding portion thereof is bound to a substrate. In some embodiments, the first antibody or antigen-binding portion thereof is detectably labeled. In some embodiments, the second antibody or antigen-binding portion thereof is detectably labeled. In some embodiments, at least one of the first antibody or antigen-binding portion thereof and the second antibody or antigen-binding portion thereof is detectably labeled. In some embodiments, the detectable label is a reporter molecule. In some embodiments, the reporter molecule is a fluorescent molecule. In some embodiments, the reporter is a radiolabel. In other embodiments, the detectable label is an enzyme. In some embodiments, the kits include a substrate for the enzyme. In some embodiments, adding a substrate to the enzyme leads to the production of a detectable signal. In some embodiments, the detectable signal is a colored soluble product. In some embodiments, the radiolabel is 1-125. In some embodiments, the enzyme is horseradish peroxidase. In some embodiments, the substrate for the enzyme is TMB. In some embodiments, the kits are capable of quantifying the amount of HERV-K or antigenic fragments thereof present in a sample. In some embodiments, the kits are capable of quantifying the amount of HERV-K TM domain present in a sample. In other embodiments, the kits are capable of quantifying the amount of HERV-K SU domain present in a sample. In some embodiments, the kits have instructions for use.

In another aspect, the present disclosure is directed to a method of detecting HERV-K or an antigenic fragment thereof, e.g. TM or SU domains of HERV-K, present in a sample. In some embodiments, the method comprises obtaining a sample containing HERV-K or an antigenic fragment thereof. In some embodiments, the method comprises contacting the sample with an anti-HERV-K antibody or antigen-binding portion thereof. In some embodiments, the method comprises detecting the presence of specific binding of the anti-HERV-K antibody or antigen-binding portion thereof to HERV-K or the antigenic fragment thereof. In further embodiments, the method includes quantifying the amount of HERV-K or antigenic fragments thereof present in the sample. In some embodiments, the sample is a biological sample. In some embodiments, the anti-HERV-K antibody or antigen-binding portion thereof specifically binds to the TM domain of HERV-K. In some embodiments, the anti-HERV-K antibody or antigen-binding portion thereof specifically binds to the SU domain of HERV-K. In some embodiments, the anti-HERV-K antibody or antigen-binding portion thereof is a monoclonal antibody. In some embodiments, the anti-HERV-K antibody or antigen-binding portion thereof is a recombinant antibody. In some embodiments, the anti-HERV-K antibody or antigen-binding portion thereof comprises one of KSN-01, KSN-02, or KSN-03. In some embodiments, detecting the presence of specific binding is accomplished by an immunoassay. In some embodiments, detecting the presence of specific binding is accomplished by a competitive immunoassay.

In another aspect, the present disclosure is directed to a method of making a recombinant antibody or antigen-binding portion thereof. In some embodiments, the method comprises transforming a host cell with at least one vector containing at least nucleic acid sequence encoding at least one of a heavy chain and a light chain of one or more anti-HERV-K antibodies or at least one or more complementarity determining regions (CDRs) of one or more heavy and/or light chains of one or more of the anti-HERV-K antibodies. In some embodiments, the method comprises expressing the at least one nucleic acid sequence to create a recombinant antibody (or antigen-binding portion thereof). In some embodiments, the method comprises recovering the recombinant antibody or antigen-binding portion thereof.

In aspect embodiment, the present disclosure is directed to an anti-HERV-K antibody or antigen-binding portion thereof for use in medicine. In some embodiments, the anti-HERV-K antibody or antigen-binding portion thereof is any anti-HERV-K antibody or antigen-binding portion thereof of the present disclosure.

In another aspect, the present disclosure is directed to an anti-HERV-K antibody or antigen-binding portion thereof for use in treatment of an HIV infection. In some embodiments, the anti-HERV-K antibody or antigen-binding portion thereof is any anti-HERV-K antibody or antigen-binding portion thereof of the present disclosure.

In another aspect, the present disclosure is directed to an anti-HERV-K antibody or antigen-binding portion thereof for use as a medicament. In some embodiments, the anti-HERV-K antibody or antigen-binding portion thereof is any anti-HERV-K antibody or antigen-binding portion thereof of the present disclosure.

In another aspect, the present disclosure is directed to use of an anti-HERV-K antibody or antigen-binding portion thereof for the manufacture of a medicament for use in the treatment of an HIV infection. In some embodiments, the anti-HERV-K antibody or antigen-binding portion thereof is any anti-HERV-K antibody or antigen-binding portion thereof of the present disclosure.

BRIEF DESCRIPTION OF THE DRAWINGS

FIG. 1 shows binding activities of human monoclonal antibodies KSN-01, KSN-02 and KSN-03 to the TM and SU domains of HERV-K.

BRIEF DESCRIPTION OF THE SEQUENCES

SEQ ID NO: 1 depicts the amino acid sequence of HERV-K envelope polypeptide:

(SEQ ID NO: 1)
MASNPSEMQRKAPPRRRHRNRAPLTHKMNKMVT*SEE*QMKLPSTKKAEPP

TWAQLKKLTQLATKYLENTKVTQTPESMLLAALMIVSMVVSLPMPAGAAA

ANYTYWAYVPFPPLIRAVTWMDNPIEVYVNDSVWVPGPIDDRCPAKPEEE

GMMINISIGYRYPPICLGRAPGCLMPAVQNWLVEVPTVSPICRFTYHMVS

GMSLRPRVNYLQDFSYQRSLKFRPKGKPCPKEIPKESKNTEVLVWEECVA

NSAVILQNNEFGTIIDWAPRGQFYHNCSGQTQSCPSAQVSPAVDSDLTES

LDKHKHKKLQSFYPWEWGEKGISTPRPKIVSPVSGPEHPELWRLTVASHH

IRIWSGNQTLETRDRKPFYTIDLNSSLTVPLQSCVKPPYMLVVGNIVIKP

DSQTITCENCRLLTCIDSTFNWQHRILLVRAREGVWIPVSMDRPWEASPS

VHILTEVLKGVLNRSKRFIFTLIAVIMGLIAVTATAAVAGVALHSSVQSV

NFVNDWQKNSTRLWNSQSSIDQKLANQINDLRQTVIWMGDRLMSLEHRFQ

LQCDWNTSDFCITPQIYNESEHHWDMVRRHLQGREDNLTLDISKLKEQIF

EASKAHLNLVPGTEAIAGVADGLANLNPVTWVKTIGSTTIINLILILVCL

FCLLLVCRCTQQLRRDSDHRERAMMTMAVLSKRKGGNVGKSKRDQIVTVS

V.

SEQ ID NO: 2 depicts the amino acid sequence of HERV-K envelope polypeptide surface unit (SU) domain:

(SEQ ID NO: 2)
AVAGVALHSSVQSVNFVNDWQKNSTRLWNSQSSIDQKLANQINDLRQTVI

WMGDRLMSLEHRFQLQCDWNTSDFCITPQIYNESEHHWDMVRRHLQGRED

NLTLDISKLKEQIFEASKAHLNLVPGTEAIAGVADGLANLNPVTWVKTIG

STTIINLILILVCLFCL.

SEQ ID NO: 3 depicts the amino acid sequence of HERV-K envelope polypeptide transmembrane I domain:

(SEQ ID NO: 3)
VVSLPMPAGAAAANYTYWAYVPFPPLIRAVTWMDNPIEVYVNDSVWVPGP

IDDRCPAKPEEEGMMINISIGYRYPPICLGRAPGCLMPAVQNWLVEVPTV

SPICRFTYHMVSGMSLRPRVNYLQDFSYQRSLKFRPKGKPCPKEIPKESK

NTEVLVWEECVANSAVILQNNEFGTIIDWAPRGQFYHNCSGQTQSCPSAQ

VSPAVDSDLTESLDKHKHKKLQSFYPWEWGEKGISTPRPKIVSPVSGPEH

PELWRLTVASHHIRIWSGNQTLETRDRKPFYTIDLNSSLTVPLQSCVKPP

YMLVVGNIVIKPDSQTITCENCRLLTCIDSTFNWQHRILLVRAREGVWIP

VSMDRPWEASPSVHILT.

SEQ ID NO: 4 depicts the amino acid sequence of heavy chain variable region CDR1 (HCDR1) of KSN-01 antibody: GDSVSSNSA (SEQ ID NO: 4).

SEQ ID NO: 5 depicts the amino acid sequence of heavy chain variable region CDR2 (HCDR2) of KSN-01 antibody: TYYRSKWYN (SEQ ID NO: 5).

SEQ ID NO: 6 depicts the amino acid sequence of heavy chain variable region CDR3 (HCDR3) of KSN-01 antibody: CARDRPWRGYRGYYYYYGMDVW (SEQ ID NO: 6).

SEQ ID NO: 7 depicts the amino acid sequence of light chain variable region CDR1 (LCDR1) of KSN-01 antibody: QSISSW (SEQ ID NO: 7).

SEQ ID NO: 8 depicts the amino acid sequence of light chain variable region CDR2 (LCDR2) of KSN-01 antibody: KAS (SEQ ID NO: 8).

SEQ ID NO: 9 depicts the amino acid sequence of light chain variable region CDR3 (LCDR3) of KSN-01 antibody: CQQYNSYSWTF (SEQ ID NO: 9).

SEQ ID NO: 10 depicts the amino acid sequence of heavy chain variable region CDR1 (HCDR1) of KSN-02 antibody: GGSFSGYY (SEQ ID NO: 10).

SEQ ID NO: 11 depicts the amino acid sequence of heavy chain variable region CDR2 (HCDR2) of KSN-02 antibody: INHSGST (SEQ ID NO: 11).

SEQ ID NO: 12 depicts the amino acid sequence of heavy chain variable region CDR3 (HCDR3) of KSN-02 antibody: CARGRPLLRFLEWSRPYYYMDVW (SEQ ID NO: 12).

SEQ ID NO: 13 depicts the amino acid sequence of light chain variable region CDR1 (LCDR1) of KSN-02 antibody: SGSIASNY (SEQ ID NO: 13).

SEQ ID NO: 14 depicts the amino acid sequence of light chain variable region CDR2 (LCDR2) of KSN-02 antibody: EDN (SEQ ID NO: 14).

SEQ ID NO: 15 depicts the amino acid sequence of light chain variable region CDR3 (LCDR3) of KSN-02 antibody: CQSYDSSNHWVF (SEQ ID NO: 15).

SEQ ID NO: 16 depicts the amino acid sequence of heavy chain variable region CDR1 (HCDR1) of KSN-03 antibody: GFTFSSYG (SEQ ID NO: 16).

SEQ ID NO: 17 depicts the amino acid sequence of heavy chain variable region CDR2 (HCDR2) of KSN-03 antibody: IWYDGSNK (SEQ ID NO: 17).

SEQ ID NO: 18 depicts the amino acid sequence of heavy chain variable region CDR3 (HCDR3) of KSN-03 antibody: CAKRGGLEGFYYFDYW (SEQ ID NO: 18).

SEQ ID NO: 19 depicts the amino acid sequence of light chain variable region CDR1 (LCDR1) of KSN-03 antibody: QSISSW (SEQ ID NO: 19).

SEQ ID NO: 20 depicts the amino acid sequence of light chain variable region CDR2 (LCDR2) of KSN-03 antibody: KAS (SEQ ID NO: 20).

SEQ ID NO: 21 depicts the amino acid sequence of light chain variable region CDR3 (LCDR3) of KSN-03 antibody: CQQYNSYSSF (SEQ ID NO: 21).

SEQ ID NO: 22 depicts the amino acid sequence of light chain variable region ($L_V$) of KSN-01 antibody:

(SEQ ID NO: 22)
DIQMTQSPSTLSASVGDRVTITCRASQSISSWLAWYQQKPGKAPKLLIYKA

SSLESGVPSRFSGSGSGTEFTLTISSLQPDDFATYYCQQYNSYSWTF.

SEQ ID NO: 23 depicts the amino acid sequence of heavy chain variable region ($H_V$) of KSN-01 antibody:

(SEQ ID NO: 23)
QVQLQQSGPGLVKPSQTLSLTCAISGDSVSSNSAAWNWIRQSPSRGLEWLG

RTYYRSKWYNDYAVSVKSRITINPDTSKNQFSLQLNSVTPEDTAVYYCARD

RPWRGYRGYYYYYGMDVW.

SEQ ID NO: 24 depicts the amino acid sequence of light chain variable region (L$_V$) of KSN-02 antibody:

(SEQ ID NO: 24)
NFMLTQPHSVSESPGKTVTISCTRSSGSIASNYVQWYQQRPGSAPTTVIYE

DNQRPSGVPDRFSGSIDSSSNSASLTISGLKTEDEADYYCQSYDSSNHWVF

GGGTKLTVLGQPKAAPS.

SEQ ID NO: 25 depicts the amino acid sequence of heavy chain variable region (H$_V$) of KSN-02 antibody:

(SEQ ID NO: 25)
QVQLQQWGAGLLKPSETLSLTCAVYGGSFSGYYWSWIRQPPGKGLEWIGEI

NHSGSTNYNPSLKSRVTISVDTSKNQFSLKLSSVTAADTAVYYCARGRPLL

RFLEWSRPYYYMDVWGK.

SEQ ID NO: 26 depicts the amino acid sequence of light chain variable region (L$_V$) of KSN-03 antibody:

(SEQ ID NO: 26)
IRMTQSPSTLSASVGDRVTITCRASQSISSWLAWYQQKPGKAPKLLIYKAS

SLESGVPSRFSGSGSGTEFTLTISSLQPDDFATYYCQQYNSYSSF.

SEQ ID NO: 27 depicts the amino acid sequence of heavy chain variable region (H$_V$) of KSN-03 antibody:

(SEQ ID NO: 27)
VQLVESGGGVVQPGRSLRLSCAASGFTFSSYGMHWVRQAPGKGLEWVAVIW

YDGSNKYYADSVKGRFTISRDNSKNTLYLQMNSLRAEDTAVYYCAKRGGLE

GFYYFDYWGQGTLVTVS.

SEQ ID NO: 28 depicts a cDNA sequence encoding the heavy chain variable region (H$_V$) of KSN-01 antibody:

(SEQ ID NO: 28)
CAGGTACAGCTGCAGCAGTCAGGTCCAGGACTGGTGAAGCCCTCGCAGACC

CTCTCACTCACCTGTGCCATCTCCGGGGACAGTGTCTCTAGCAACAGTGCT

GCTTGGAACTGGATCAGGCAGTCCCCATCGAGAGGCCTTGAGTGGCTGGGA

AGGACATACTACAGGTCCAAGTGGTATAATGATTATGCAGTATCTGTGAAA

AGTCGAATAACCATCAACCCAGACACATCCAAGAACCAGTTCTCCCTGCAG

CTGAACTCTGTGACTCCCGAGGACACGGCTGTGTATTACTGTGCAAGAGAT

AGGCCCTGGCGTGGTTACCGAGGTTACTACTACTAGTACGGTATGGACGTC

TGGGGCCAAGGGACCACGGTCACCGTCTCCTCAG.

SEQ ID NO: 29 depicts a cDNA sequence encoding the light chain variable region (L$_V$) of KSN-01 antibody:

(SEQ ID NO: 29)
GACATCCAGATGACCCAGTCTCCTTCCACCCTGTCTGCATCTGTAGGAGAC

AGAGTCACCATCACTTGCCGGGCCAGTCAGAGTATTAGTAGCTGGTTGGCC

TGGTATCAGCAGAAACCAGGGAAAGCCCCTAAGCTCCTGATCTATAAGGCG

TCTAGTTTAGAAAGTGGGGTCCCATCAAGGTTCAGCGGCAGTGGATCTGGG

ACAGAATTCACTCTCACCATCAGCAGCCTGCAGCCTGATGATTTTGCAACT

TATTACTGCCAACAGTATAATAGTTATTCGTGGACGTTCGGCCAAGGGACC

AAGGTGGAAATCAAAC.

SEQ ID NO: 30 depicts a cDNA sequence encoding the heavy chain variable region (H$_V$) of KSN-02 antibody:

(SEQ ID NO: 30)
CAGGTGCAGCTACAGCAGTGGGGCGCAGGACTGTTGAAGCCTTCGGAGACC

CTGTCCCTCACCTGCGCTGTCTATGGTGGGTCCTTCAGTGGTTACTACTGG

AGCTGGATCCGCCAGCCCCCAGGGAAGGGGCTGGAGTGGATTGGGGAAATC

AATCATAGTGGAAGCACCAACTACAACCCGTCCCTCAAGAGTCGAGTCACC

ATATCAGTAGACACGTCCAAGAACCAGTTCTCCCTGAAGCTGAGCTCTGTG

ACCGCCGCGGACACGGCTGTGTATTACTGTGCGAGAGGCCGCCCGTTATTA

CGATTTTTGGAGTGGTCCAGGCCCTACTACTACATGGACGTCTGGGGCAAA

GGGACCACGGTCACCGTCTCCTCAG.

SEQ ID NO: 31 depicts a cDNA sequence encoding the light chain variable region (L$_V$) of KSN-02 antibody:

(SEQ ID NO: 31)
AATTTTATGCTGACTCAGCCGCACTCTGTGTCGGAGTCTCCGGGGAAGAC

GGTAACCATCTCCTGCACCCGCAGCAGTGGCAGCATTGCCAGCAACTATG

TGCAGTGGTACCAGCAGCGCCCGGGCAGTGCCCCCACCACTGTGATCTAT

GAGGATAACCAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCTTATGATAGCAGCAACCATTGG

GTGTTCGGCGGAGGGACCAAGCTGACCGTCCTAGGTCAGCCCAAGGCTGC

CCCCTCGGTC.

SEQ ID NO: 32 depicts a cDNA sequence encoding the heavy chain variable region (H$_V$) of KSN-03 antibody:

(SEQ ID NO: 32)
AGGTGCAGCTGGTGGAGTCTGGGGGAGGCGTGGTCCAGCCTGGGAGGTCC

CTGAGACTCTCCTGTGCAGCGTCTGGATTCACCTTCAGTAGCTATGGCAT

GCACTGGGTCCGCCAGGCTCCAGGCAAGGGGCTGGAGTGGGTGGCAGTTA

TATGGTATGATGGAAGTAATAAATACTATGCAGACTCCGTGAAGGGCCGA

TTCACCATCTCCAGAGACAATTCCAAGAACACGCTGTATCTGCAAATGAA

CAGCCTGAGAGCCGAGGACACGGCTGTGTATTACTGTGCGAAACGAGGGG

GGTTGGAGGGCTTCTACTACTTTGACTACTGGGGCCAGGGAACCCTGGTC

ACCGTCTCCT.

SEQ ID NO: 33 depicts a cDNA sequence encoding the light chain variable region (L$_V$) of KSN-03 antibody:

(SEQ ID NO: 33)
CATCCGGATGACCCAGTCTCCTTCCACCCTGTCCGCATCTGTAGGAGACA

GAGTCACCATCACTTGCCGGGCCAGTCAGAGTATTAGTAGCTGGTTGGCC

TGGTATCAGCAGAAACCAGGGAAAGCCCCTAAGCTCCTGATCTATAAGGC

```
GTCTAGTTTAGAAAGTGGGGTCCCATCAAGGTTCAGCGGCAGTGGATCTG

GGACAGAATTCACTCTCACCATCAGCAGCCTGCAGCCTGATGATTTTGCA

ACTTATTACTGCCAACAGTATAATAGTTATTCCTCTTTCGGCCCTGGGAC

CAAGCTGGAGATCAAAC.
```

SEQ ID NO: 34 depicts Forward 5' VH1 LEADER-A Primer:

```
                                        (SEQ ID NO: 34)
             ATGGACTGGACCTGGAGGAT
```

SEQ ID NO: 35 depicts Forward 5' VH1 LEADER-B Primer:

```
                                        (SEQ ID NO: 35)
             ATGGACTGGACCTGGAGCAT
```

SEQ ID NO: 36 depicts Forward 5' VH1 LEADER-C Primer:

```
                                        (SEQ ID NO: 36)
             ATGGACTGGACCTGGAGAAT
```

SEQ ID NO: 37 depicts Forward 5' VH1 LEADER-D Primer:

```
                                        (SEQ ID NO: 37)
             GGTTCCTCTTTGTGGTGGC
```

SEQ ID NO: 38 depicts Forward 5' VH1 LEADER-E Primer:

```
                                        (SEQ ID NO: 38)
             ATGGACTGGACCTGGAGGGT
```

SEQ ID NO: 39 depicts Forward 5' VH1 LEADER-F Primer:

```
                                        (SEQ ID NO: 39)
             ATGGACTGGATTTGGAGGAT
```

SEQ ID NO: 40 depicts Forward 5' VH1 LEADER-G Primer:

```
                                        (SEQ ID NO: 40)
             AGGTTCCTCTTTGTGGTGGCAG
```

SEQ ID NO: 41 depicts Forward 5' VH2Ext Primer:

```
                                        (SEQ ID NO: 41)
             CATACTTTGTTCCACGCTCC
```

SEQ ID NO: 42 depicts Forward 5' VH3 LEADER-A Primer:

```
                                        (SEQ ID NO: 42)
             TAAAAGGTGTCCAGTGT
```

SEQ ID NO: 43 depicts Forward 5' VH3 LEADER-B Primer:

```
                                        (SEQ ID NO: 43)
             TAAGAGGTGTCCAGTGT
```

SEQ ID NO: 44 depicts Forward 5' VH3 LEADER-C Primer:

```
                                        (SEQ ID NO: 44)
             TAGAAGGTGTCCAGTGT
```

SEQ ID NO: 45 depicts Forward 5' VH3 LEADER-D Primer:

```
                                        (SEQ ID NO: 45)
             GCTATTTTTAAAGGTGTCCAGTGT
```

SEQ ID NO: 46 depicts Forward 5' VH3 LEADER-E Primer:

```
                                        (SEQ ID NO: 46)
             TACAAGGTGTCCAGTGT
```

SEQ ID NO: 47 depicts Forward 5' VH3 LEADER-F Primer:

```
                                        (SEQ ID NO: 47)
             TTAAAGCTGTCCAGTGT
```

SEQ ID NO: 48 depicts Forward 5' VH4 LEADER-A Primer:

```
                                        (SEQ ID NO: 48)
             ATGAAACACCTGTGGTTCTTCC
```

SEQ ID NO: 49 depicts Forward 5' VH4 LEADER-B Primer:

```
                                        (SEQ ID NO: 49)
             ATGAAACACCTGTGGTTCTT
```

SEQ ID NO: 50 depicts Forward 5' VH4 LEADER-C Primer:

```
                                        (SEQ ID NO: 50)
             ATGAAGCACCTGTGGTTCTT
```

SEQ ID NO: 51 depicts Forward 5' VH4 LEADER-D Primer:

```
                                        (SEQ ID NO: 51)
             ATGAAACATCTGTGGTTCTT
```

SEQ ID NO: 52 depicts Forward 5' VH5 LEADER-A Primer:

```
                                        (SEQ ID NO: 52)
             TTCTCCAAGGAGTCTGT
```

SEQ ID NO: 53 depicts Forward 5' VH5 LEADER-B Primer:

(SEQ ID NO: 53)
CCTCCACAGTGAGAGTCTG

SEQ ID NO: 54 depicts Forward 5' VH6 LEADER-A Primer:

(SEQ ID NO: 54)
ATGTCTGTCTCCTTCCTCATC

SEQ ID NO: 55 depicts Forward 5' VH7 LEADER-A Primer:

(SEQ ID NO: 55)
GGCAGCAGCAACAGGTGCCCA

SEQ ID NO: 56 depicts External 3' IgMExt1 Primer:

(SEQ ID NO: 56)
GTGATGGAGTCGGGAAGGAA

SEQ ID NO: 57 depicts External 3' IgAExt Primer:

(SEQ ID NO: 57)
GTGTAGTGCTTCACGTGGCA

SEQ ID NO: 58 depicts External 3' IgGExt Primer:

(SEQ ID NO: 58)
GAGTCCTGAGGACTGTAGGA

SEQ ID NO: 59 depicts Internal 3' IgMInt1 Primer:

(SEQ ID NO: 59)
CGACGGGGAATTCTCACAGG

SEQ ID NO: 60 depicts Internal 3' IgAInt Primer:

(SEQ ID NO: 60)
CGACGGGGAATTCTCACAGG

SEQ ID NO: 61 depicts Internal 3' IgGInt Primer:

(SEQ ID NO: 61)
GCGCCTGAGTTCCACGACAC

SEQ ID NO: 62 depicts External 5' L VK1/2 Primer:

(SEQ ID NO: 62)
ATGAGGSTCCCYGCTCAGCTGCTGG

SEQ ID NO: 63 depicts External 5' L VK3 Primer:

(SEQ ID NO: 63)
CTCTTCCTCCTGCTACTCTGGCTCCC

SEQ ID NO: 64 depicts External 5' L VK4 Primer:

(SEQ ID NO: 64)
ATTTCTCTGTTGCTCTGGATCTCTG

SEQ ID NO: 65 depicts External 3' CK 543 Primer:

(SEQ ID NO: 65)
GTTTCTCGTAGTCTGCTTTGCTCA

SEQ ID NO: 66 depicts Internal 5' PAN VK Primer:

(SEQ ID NO: 66)
ATGACCCAGWCTCCABYCWCCCTG

SEQ ID NO: 67 depicts Internal 3' CK 494 Primer:

(SEQ ID NO: 67)
GTGCTGTCCTTGCTGTCCTGCT

SEQ ID NO: 68 depicts External 5' L VL1 Primer:

(SEQ ID NO: 68)
GGTCCTGGGCCCAGTCTGTGCTG

SEQ ID NO: 69 depicts External 5' L VL2 Primer:

(SEQ ID NO: 69)
GGTCCTGGGCCCAGTCTGCCCTG

SEQ ID NO: 70 depicts External 5' L VL3 Primer:

(SEQ ID NO: 70)
GCTCTGTGACCTCCTATGAGCTG

SEQ ID NO: 71 depicts External 5' L VL4/5 Primer:

(SEQ ID NO: 71)
GGTCTCTCTCSCAGCYTGTGCTG

SEQ ID NO: 72 depicts External 5' L VL6 Primer:

(SEQ ID NO: 72)
GTTCTTGGGCCAATTTTATGCTG

SEQ ID NO: 73 depicts External 5' L VL7 Primer:

(SEQ ID NO: 73)
GGTCCAATTCYCAGGCTGTGGTG

SEQ ID NO: 74 depicts External 5' L VL8 Primer:

(SEQ ID NO: 74)
GAGTGGATTCTCAGACTGTGGTG

SEQ ID NO: 75 depicts External 3' CL Primer:

(SEQ ID NO: 75)
CACCAGTGTGGCCTTGTTGCCTTG

SEQ ID NO: 76 depicts Internal 5' AGEI VL1 Primer:

(SEQ ID NO: 76)
CTGCTACCGGTTCCTGGGCCCAGTC

SEQ ID NO: 77 depicts Internal 5' AGEI VL2 Primer:

CTGCTACCGGTTCCTGGGCCCAGTC (SEQ ID NO: 77)

SEQ ID NO: 78 depicts Internal 5' AGEI VL3 Primer:

CTGCTACCGGTTCTGTGACCTCCTAT (SEQ ID NO: 78)

SEQ ID NO: 79 depicts Internal 5' AGEI VL4/5 Primer:

CTGCTACCGGTTCTCTCTCSCAGCYT (SEQ ID NO: 79)

SEQ ID NO: 80 depicts Internal 5' AGEI VL6 Primer:

CTGCTACCGGTTCTTGGGCCAATTTT (SEQ ID NO: 80)

SEQ ID NO: 81 depicts Internal 5' AGEI VL7/8 Primer:

CTGCTACCGGTTCCAATTCYCAGRCT (SEQ ID NO: 81)

SEQ ID NO: 82 depicts Internal 3' XHOI CL Primer:

CTCCTCACTCGAGGGYGGGAACAGA (SEQ ID NO: 82)

DETAILED DESCRIPTION OF THE INVENTION

For purposes of interpreting this specification, the following definitions will apply and whenever appropriate, terms used in the singular will also include the plural and vice versa.

The term "antibody" as referred to herein includes whole antibodies and any antigen binding fragment or single chains thereof. Whole antibodies are glycoproteins comprising at least two heavy (H) chains and two light (L) chains interconnected by disulfide bonds. Each heavy chain is comprised of a heavy chain variable region (abbreviated herein as $V_H$) and a heavy chain constant region. The heavy chain constant region is comprised of three domains, $C_H1$, $C_H2$ and $C_H3$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The heavy chain variable region CDRs and FRs are HFR1, HCDR1, HFR2, HCDR2, HFR3, HCDR3, HFR4. The light chain variable region CDRs and FRs are LFR1, LCDR1, LFR2, LCDR2, LFR3, LCDR3, LFR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (Ciq) of the classical complement system.

The term "antigen-binding fragment or portion" of an antibody (or simply "antibody fragment or portion"), as used herein, includes one or more fragments of an antibody that retain the ability to specifically bind to an antigen (e.g., a HERV-K Envelope polypeptide, including but not limited to the TM and/or SU domain). It has been shown that the antigen-binding function of an antibody can be performed by fragments of a full-length antibody. Examples of binding portions encompassed within the term "antigen-binding portion or portion" of an antibody include (i) a Fab fragment, a monovalent fragment consisting of the $V_L$, $V_H$, $C_L$ and $C_H$I domains; (ii) a F(ab')2 fragment, a bivalent fragment comprising two Fab fragments linked by a disulfide bridge at the hinge region; (iii) a Fab' fragment, which is essentially an Fab with part of the hinge region (see, FUNDAMENTAL IMMUNOLOGY (Paul ed., 3.sup.rd ed. 1993)); (iv) a Fd fragment consisting of the $V_H$ and $C_H$I domains; (v) a Fv fragment consisting of the $V_L$ and $V_H$ domains of a single arm of an antibody, (vi) a dAb fragment (Ward et al., (1989) Nature 341:544-546), which consists of a $V_H$ domain; (vii) an isolated complementarity determining region (CDR); and (viii) a nanobody, a heavy chain variable region containing a single variable domain and two constant domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. ScL USA 85:5879-5883). Such single chain antibodies are also intended to be encompassed within the term "antigen-binding portion or portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds to a HERV-K envelope protein is substantially free of antibodies that specifically bind antigens other than HERV-K envelope proteins). An isolated antibody can be substantially free of other cellular material and/or chemicals. The terms "monoclonal antibody" or "monoclonal antibody composition" as used herein refer to a preparation of antibody molecules of single molecular composition. In one example, a monoclonal antibody composition displays a single binding specificity and affinity for a particular epitope. In another example, a monoclonal antibody also includes a bispecific monoclonal antibody. As used herein, the term "bispecific antibody" refers to a protein, which has the ability to bind to two different epitopes on the same or different antigens. A bispecific antibody therefore typically has two different (types of) paratopes, i.e. antigen-binding sites. In particular, a bispecific antibody may comprise two or more paratopes, wherein some paratopes may be identical so that all paratopes of the antibody belong to only two different types of paratopes and, hence, the antibody has two specificities. For example, the bispecific, in particular trifunctional, antibody according to the present invention may comprise four paratopes, wherein each two paratopes are identical (i.e. have the same specificity) and, thus, the antibody is bispecific (two identical paratopes for each of the two specificities). As used herein, "one specificity" in particular refers to one or more paratopes exhibiting the same specificity (which typically means that such one or more paratopes are identical) and, thus, "two specificities" may be realized by two, three, four five, six or more paratopes as long as they refer to only two specificities. Preferably a single antibody comprises one single paratope for each of the two specificities, i.e. the antibody comprises in total two paratopes. Preferably the antibody comprises two (identical) paratopes for each of the two specificities, i.e. the antibody comprises in total four paratopes. Preferably the antibody comprises three (identical) paratopes for each of the two specificities, i.e. the antibody comprises in total six paratopes. More preferably, the antibody comprises one single paratope for each of the two specificities, i.e. the antibody comprises in total two paratopes. More preferably, the antibody comprises two (identical) paratopes for each of the two specificities, i.e. the antibody comprises in total four paratopes. Most preferably, the antibody comprises one single paratope for each of the two specificities, i.e. the antibody comprises in total two paratopes.

The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity, which have variable regions in which both the framework and CDR regions are derived from human immunoglobulin sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom (described further below), (b) antibodies isolated from a host cell transformed to express the human antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

The term "isotype" refers to the antibody class (e.g., IgG1 for the exemplary antibodies KSN-01, KSN-02, and KSN-03) that is encoded by the heavy chain constant region genes. The phrases "an antibody recognizing an antigen" and "an antibody specific for an antigen" are used interchangeably herein with the term "an antibody which binds specifically to an antigen."

The term "human antibody derivatives" refers to any modified form of the human antibody, e.g., a conjugate of the antibody and another agent or antibody. The term "humanized antibody" is intended to refer to antibodies in which CDR sequences derived from the germline of another mammalian species, such as a mouse, have been grafted onto human framework sequences. Additional framework region modifications can be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

As used herein, the term "affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (KD). Affinity can be measured by common methods known in the art, including those described herein.

As used herein, an antibody that "specifically binds to human HERV-K envelope polypeptide" is intended to refer to an antibody that binds to human HERV-K envelope polypeptide (and possibly a HERV-K envelope polypeptide from one or more non-human species) but does not substantially bind to non-HERV-K envelope polypeptide. Preferably, the antibody binds to a human HERV-K envelope polypeptide with "high affinity", namely with a $K_D$ of $1 \times 10^{-7}$ M or less, more preferably $5 \times 10^{-8}$ M or less, more preferably $3 \times 10^{-8}$ M or less, more preferably $1 \times 10^{-8}$ M or less, more preferably $5 \times 10^{-9}$ M or less or even more preferably $1 \times 10^{-9}$ M or less. The term "does not substantially bind" to a protein or cells, as used herein, means does not bind or does not bind with a high affinity to the protein or cells, i.e. binds to the protein or cells with a $K_D$ of $1 \times 10^{-6}$ M or more, more preferably $1 \times 10^{-5}$ M or more, more preferably $1 \times 10^{-4}$ M or more, more preferably $1 \times 10^{-3}$ M or more, even more preferably $1 \times 10^{-2}$ M or more.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$," as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system.

The term "epitope" as used herein refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. An epitope typically includes at least about 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immune-precipitation assays, wherein overlapping or contiguous peptides from (e.g., from MICA) are tested for reactivity with a given antibody (e.g., anti-Mi C A antibody). Methods of determining spatial conformation of epitopes include techniques in the art and those described herein, for example, x-ray crystallography and 2-dimensional nuclear magnetic resonance (see, e.g., Epitope Mapping Protocols in Methods in Molecular Biology, Vol. 66, G. E. Morris, Ed. (1996)).

The term "epitope mapping" refers to the process of identification of the molecular determinants for antibody-antigen recognition.

The term "binds to an epitope" or "recognizes an epitope" with reference to an antibody or antibody fragment refers to continuous or discontinuous segments of amino acids within an antigen. Those of skill in the art understand that the terms do not necessarily mean that the antibody or antibody fragment is in direct contact with every amino acid within an epitope sequence.

The term "binds to the same epitope" with reference to two or more antibodies means that the antibodies bind to the same, overlapping or encompassing continuous or discontinuous segments of amino acids. Those of skill in the art understand that the phrase "binds to the same epitope" does not necessarily mean that the antibodies bind to or contact exactly the same amino acids. The precise amino acids which the antibodies contact can differ. For example, a first antibody can bind to a segment of amino acids that is completely encompassed by the segment of amino acids bound by a second antibody. In another example, a first antibody binds one or more segments of amino acids that significantly overlap the one or more segments bound by the second antibody. For the purposes herein, such antibodies are considered to "bind to the same epitope."

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least about 10%, 20%, 30%, 40%, 50%, 60%, 70%, 80%, 90% or about 100%, or any intervening range therein. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance). Other competitive binding assays include: solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., Virology 176:546 (1990)); and direct labeled RIA. (Moldenhauer et al., *Scand. J. Immunol.* 32:77 (1990)), each reference hereby incorporated by reference in its entirety.

As used herein, the term "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a $CD4^+$ or $CD8^+$ T cell, or the inhibition of a $T_{reg}$ cell.

The term "detectable label" as used herein refers to a molecule capable of detection, including, but not limited to, radioactive isotopes, fluorescers, chemiluminescers, chromophores, enzymes, enzyme substrates, enzyme cofactors, enzyme inhibitors, chromophores, dyes, metal ions, metal sols, ligands (e.g., biotin, avidin, streptavidin or haptens), intercalating dyes and the like. The term "fluorescer" refers to a substance or a portion thereof which is capable of exhibiting fluorescence in the detectable range.

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "therapeutically effective amount" of a compound of the present invention refers to an amount of the compound of the present invention that will elicit the biological or medical response of a subject, or ameliorate symptoms, slow or delay disease progression, or prevent a disease, etc. In one embodiment, the term refers to the amount that inhibits or reduces microbial colonization or infection. In one embodiment, the term refers to the amount that inhibits or reduces bacterial infection, or prevent or destroying the formation of bacterial biofilms. When applied to an individual active ingredient, administered alone, the term refers to that ingredient alone. When applied to a combination, the term refers to combined amounts of the active ingredients that result in the therapeutic effect, whether administered in combination, serially or simultaneously.

As used herein, the term "pharmaceutically acceptable carrier or excipient" refers to a carrier medium or an excipient which does not interfere with the effectiveness of the biological activity of the active ingredient(s) of the composition and which is not excessively toxic to the host at the concentrations at which it is administered. In the context of the present invention, a pharmaceutically acceptable carrier or excipient is preferably suitable for topical formulation. The term includes, but is not limited to, a solvent, a stabilizer, a solubilizer, a tonicity enhancing agent, a structure-forming agent, a suspending agent, a dispersing agent, a chelating agent, an emulsifying agent, an anti-foaming agent, an ointment base, an emollient, a skin protecting agent, a gel-forming agent, a thickening agent, a pH adjusting agent, a preservative, a penetration enhancer, a complexing agent, a lubricant, a demulcent, a viscosity enhancer, a bioadhesive polymer, or a combination thereof. The use of such agents for the formulation of pharmaceutically active substances is well known in the art (see, for example, "Remington's Pharmaceutical Sciences", E. W. Martin, $18^{th}$ Ed., 1990, Mack Publishing Co.: Easton, Pa., which is incorporated herein by reference in its entirety).

As used herein, the term "treating" or "treatment" of any disease or disorder refers in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

The term "homology" as used herein may refer to the existence of shared structure between two compositions. The term "homology" in the context of proteins may refer to the amount (e.g. expressed in a percentage) of overlap between two or more amino acid and/or peptide sequences. In the context of nucleic acids, the term may refer to the amount (e.g. expressed in a percentage) of overlap between two or more nucleic acid sequences. As used herein, the percent (%) homology between two sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm. Such homology is well-represented in the art via local alignment tools and/or algorithms, and may include pairwise alignment, multiple sequence alignment methods, structural alignment methods, and/or phylogenetic analysis methods.

The terms "co-administration," "co-administered," and "in combination with" as used herein may refer to the administration of at least two agents or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary.

The terms "conservative sequence modifications" or "conservative substitutions" as used herein may refer to amino acid modifications to a target epitope of the invention that do not significantly affect or alter the binding characteristics of the anti-HERV-K antibodies to the epitope(s). Such conservative modifications include amino acid substitutions, additions and deletions. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a target epitope that the anti-HERV-K antibodies of the invention specifically bind to, e.g. epitopes on the viral envelope of HERV-K, can be replaced with other amino acid residues from the same side chain family and the antibodies of the present disclosure can be tested against the target epitope can be tested, for example using functional assays described herein or otherwise known in the art.

The terms "purified" or "isolated" antibody, peptide, polypeptide, or protein refers to a peptide, polypeptide, or protein, as used herein, may refer to a peptide, polypeptide, or protein that has been separated from other proteins, lipids, and nucleic acids with which it is naturally associated. The polypeptide/protein can constitute at least 10% (i.e., any percentage between 10% and 100%, e.g., 20%, 30%, 40%, 50%, 60%, 70%, 80%, 85%, 90%, 95%, and 99%) by dry weight of the purified preparation. Purity can be measured by any appropriate standard method, for example, by column chromatography, polyacrylamide gel electrophoresis, or HPLC analysis. An isolated polypeptide/protein (e.g., anti-HERV-K antibodies) described in the invention can be produced by recombinant DNA techniques.

The term "biological sample" as used herein may refer to a sample obtained from an organism (e.g., patient) or from components (e.g., cells) of an organism. The sample may be of any biological tissue, cell(s) or fluid. The sample may be a "clinical sample" which is a sample derived from a subject, such as a human patient. Such samples include, but are not limited to, saliva, sputum, blood, blood cells (e.g., white cells), bodily fluids, lavages, pancreatic juices, gastric juices, discharges, CSF, lymph amniotic fluid, plasma, semen, bone marrow, and tissue or fine needle biopsy samples, urine, stool, peritoneal fluid, and pleural fluid, or cells therefrom, and any combinations thereof. Biological samples may also include sections of tissues such as frozen sections taken for histological purposes. A biological sample may also be referred to as a "patient sample." A biological sample may also include a substantially purified or isolated protein, membrane preparation, or cell culture.

As used herein, the term "a," "an," "the" and similar terms used in the context of the present invention (especially in the context of the claims) are to be construed to cover both the singular and plural unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

As used herein, the term "about" refers to within 10%, preferably within 5%, and more preferably within 1% of a given value or range. Alternatively, the term "about" refers to within an acceptable standard error of the mean, when considered by one of ordinary skill in the art. Context will dictate what is appropriate in each individual circumstance as the term "about" appears in the present disclosure.

Various aspects of the invention are described in further detail in the following subsections.

Anti-HERV-K Antibodies

In one aspect, the present invention provides an isolated antibody or an antigen-binding portion thereof that specifically binds to human HERV-K, e.g. a HERV-K envelope (Env) polypeptide. In one embodiment, the antibody is monoclonal antibody. In one embodiment, the anti-human HERV-K envelope polypeptide antibody binds to the human HERV-K envelope polypeptide expressed on the surface of cells infected with HIV virus and the binding triggers immune response that inhibits the HIV infectivity or eliminates the HIV-infected cells.

In one embodiment, the antibody or the antigen-binding portion thereof specifically binds to the surface unit (SU) domain of the human HERV-K envelope polypeptide. In one embodiment, the antibody or the antigen-binding portion thereof specifically binds to the transmembrane I domain of the human HERV-K envelope polypeptide.

In one embodiment, the antibody or the antigen-binding portion thereof specifically binds to the human HERV-K envelope polypeptide or the antigen-binding portion thereof with high affinity. In another embodiment, the binding is with a $K_D$ of $10^{-7}$ M or less, $10^{-8}$ M or less, $10^{-9}$ M or less, $10^{-10}$ M or less, $10^{-11}$ M or less, $10^{-12}$ M or less, $10^{-12}$ M to $10^{-7}$ M, $10^{-11}$ M to $10^{-7}$ M, $10^{-10}$ M to $10^{-7}$ M, or $10^{-9}$ M to $10^{-7}$ M. Ways of determining the binding affinity of the antibody are well known in the art.

One of ordinary skill in the art will appreciate that the complementarity determining regions ("CDRs") of most antibodies, e.g., KSN-01, KSN-02, and KSN-03 largely determine the biological activity of the antibodies by forming the paratope on the antibody. Accordingly, some embodiments of the present disclosure are directed to antibodies expressing the CDRs listed in TABLE 5 infra.

In one embodiment, the antibody or the antigen-binding portion thereof specifically binds to the surface unit domain of the human HERV-K envelope polypeptide and comprises a heavy chain variable region comprising a HCDR1 comprising an amino acid sequence of SEQ ID NO: 4, a HCDR2 comprising an amino acid sequence of SEQ ID NO: 5 and a HCDR3 comprising an amino acid sequence of SEQ ID NO: 6; and a light chain variable region comprising a LCDR1 comprising an amino acid sequence of SEQ ID NO: 7, a LCDR2 comprising an amino acid sequence of SEQ ID NO: 8 and a LCDR3 comprising an amino acid sequence of SEQ ID NO: 9.

In one embodiment, the antibody or the antigen-binding portion thereof specifically binds to the surface unit domain of the human HERV-K envelope polypeptide and comprises a heavy chain variable region comprising amino acid sequence of SEQ ID NO: 23 and light chain variable region comprises an amino acid sequence of SEQ ID NO:22.

In one embodiment, the antibody or the antigen-binding portion thereof specifically binds to the surface unit (SU) domain of the human HERV-K envelope polypeptide and comprises a heavy chain variable region comprising a HCDR1 comprising an amino acid sequence of SEQ ID NO: 10, a HCDR2 comprising an amino acid sequence of SEQ ID NO: 11 and a HCDR3 comprising an amino acid sequence of SEQ ID NO: 12; and a light chain variable region comprising a LCDR1 comprising an amino acid sequence of SEQ ID NO: 13, a LCDR2 comprising an amino acid sequence of SEQ ID NO: 14 and a LCDR3 comprising an amino acid sequence of SEQ ID NO: 15.

In one embodiment, the antibody or the antigen-binding portion thereof specifically binds to the surface unit (SU) domain of the human HERV-K envelope polypeptide and comprises a heavy chain variable region comprising amino acid sequence of SEQ ID NO: 25 and light chain variable region comprises an amino acid sequence of SEQ ID NO:24.

In one embodiment, the antibody or the antigen-binding portion thereof specifically binds to the transmembrane I domain of the human HERV-K envelope polypeptide and comprises a heavy chain variable region comprising a HCDR1 comprising an amino acid sequence of SEQ ID NO: 16, a HCDR2 comprising an amino acid sequence of SEQ ID NO: 17 and a HCDR3 comprising an amino acid sequence of SEQ ID NO: 18; and a light chain variable region comprising a LCDR1 comprising an amino acid sequence of SEQ ID NO: 19, a LCDR2 comprising an amino acid sequence of SEQ ID NO: 20 and a LCDR3 comprising an amino acid sequence of SEQ ID NO: 21.

In one embodiment, the antibody or the antigen-binding portion thereof specifically binds to the transmembrane I domain of the human HERV-K envelope polypeptide and comprises a heavy chain variable region comprising amino acid sequence of SEQ ID NO: 27 and light chain variable region comprises an amino acid sequence of SEQ ID NO:26.

In some embodiments, the present invention also encompasses antibodies having heavy chain variable regions comprising amino acid sequences that are homologous to the amino acid sequences of the antibodies described herein. In one embodiment, the antibody comprises a heavy chain variable region comprising an amino acid sequence that is 75%, 80%, 85%, 90%, 95%, 96%, 97%, 98% or 99% identical to an amino acid sequence selected from the group consisting of SEQ ID NOs: 23, 25 and 27.

In one embodiment, the present invention also encompasses antibodies having light chain variable regions comprising amino acid sequences that are homologous to the amino acid sequences of the antibodies described herein. In one embodiment, the antibody comprises a light chain variable region comprising an amino acid sequence that is 75%, 80%, 85%, 90%, 95%, 96%, 97%, 98% or 99% identical to an amino acid sequence selected from the group consisting of SEQ ID NOs: 22, 24 and 26.

In some embodiments, the antibodies of the present invention described herein comprise one or more non-naturally occurring amino acids. In one embodiment, the non-naturally encoded amino acid comprises a carbonyl group, an acetyl group, an aminooxy group, a hydrazine group, a hydrazide group, a semicarbazide group, an azide group, or an alkyne group. See, e.g., U.S. Pat. No. 7,632,924 for suitable non-naturally occurring amino acids. Inclusion of a non-naturally occurring amino acid can provide for linkage to a polymer, a second polypeptide, a scaffold, etc. For example, a subject antibody linked to a water-soluble polymer can be made by reacting a water-soluble polymer (e.g., PEG) that comprises a carbonyl group to the subject antibody that comprises a non-naturally encoded amino acid that comprises an aminooxy, hydrazine, hydrazide or semicarbazide group. As another example, a subject antibody linked to a water-soluble polymer can be made by reacting a subject antibody that comprises an alkyne-containing amino acid with a water-soluble polymer (e.g., PEG) that comprises an azide moiety; in some embodiments, the azide or alkyne group is linked to the PEG molecule through an amide linkage. A "non-naturally encoded amino acid" refers to an amino acid that is not one of the 20 common amino acids or pyrolysine or selenocysteine. Other terms that may be used synonymously with the term "non-naturally encoded amino acid" are "non-natural amino acid," "unnatural amino acid," "non-naturally-occurring amino acid," and variously hyphenated and non-hyphenated versions thereof. The term "non-naturally encoded amino acid" also includes, but is not limited to, amino acids that occur by modification (e.g. post-translational modifications) of a naturally encoded amino acid (including but not limited to, the 20 common amino acids or pyrolysine and selenocysteine) but are not themselves naturally incorporated into a growing polypeptide chain by the translation complex. Examples of such non-naturally-occurring amino acids include, but are not limited to, N-acetylglucosaminyl-L-serine, N-acetylglucosaminyl-L-threonine, and O-phosphotyrosine.

The present invention also provides antibodies that compete for binding to HERV-K envelope polypeptide (either SU or TM domain) with the particular antibodies described herein (e.g., antibodies KSN-01, KSN-02 and KSN-03). Such antibodies can be identified based on their ability to competitively inhibit binding to HERV-K envelope polypeptide of one or more monoclonal antibodies KSN-01, KSN-02 and KSN-03 in standard antibody binding assays. Such standard antibody binding assays can be standard or competitive ELISA assays in which HERV-K envelope polypeptide is immobilized on the plate, various concentrations of unlabeled first antibody is added, the plate is washed, labeled second antibody is added, and the amount of label is measured. If the increasing concentration of the unlabeled (first) antibody (also referred to as the "blocking antibody") inhibits the binding of the labeled (second) antibody, the first antibody is said to inhibit the binding of the second antibody to the target on the plate, or is said to compete with the binding of the second antibody. Additionally or alternatively, BIAcore analysis can be used to assess the ability of the antibodies to compete. The ability of a test antibody to inhibit the binding of an anti-HERV-K Env antibody described herein to HERV-K Env demonstrates that the test antibody can compete with the antibody for binding to HERV-K Env.

Accordingly, provided herein are anti-HERV-K Env antibodies that inhibit the binding of an anti-HERV-K Env antibodies described herein to HERV-K Env on cells by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% and/or whose binding to HERV-K Env, is inhibited by at least 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100%.

In certain embodiments, the anti-HERV-K Env antibodies binds to the same epitope on the human HERV-K envelope polypeptide that is recognized by the particular antibodies described herein (e.g., antibodies KSN-01, KSN-02 and KSN-03). Antibodies that compete for binding with, or bind to the same epitope as, the anti-HERV-K Env antibodies described herein may be identified by using art-known methods. Techniques for determining antibodies that bind to the "same epitope on HERV-K Envelope polypeptide" with the antibodies described herein include, for example, epitope mapping methods, such as, x-ray analyses of crystals of antigen: antibody complexes which provides atomic resolution of the epitope. Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. Methods may also rely on the ability of an antibody of interest to affinity isolate specific short peptides (either in native three dimensional form or in denatured form) from combinatorial phage display peptide libraries. The peptides are then regarded as leads for the definition of the epitope corresponding to the antibody used to screen the peptide library. For epitope mapping, computational algorithms have also been developed which have been shown to map conformational discontinuous epitopes.

Yet in certain embodiments, the anti-HERV-K Env antibodies as described herein are human or chimeric antibodies.

The present invention also provides engineered and modified antibodies that can be prepared using an antibody having one or more of the heavy chain variable ($V_H$) and/or light chain variable ($V_L$) sequence disclosed herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) Nature 332:323-327; Jones, P. et al. (1986) Nature 321:522-525; Queen, C. et al. (1989) Proc. Natl. Acad. See.

U.S.A. 86: 10029-10033; U.S. Pat. No. 5,225,539 to Winter, and U.S. Pat. Nos. 5,530,101; 5,585,089; 5,693,762 and 6,180,370 to Queen et al.)

Accordingly, one embodiment described herein pertains to an isolated monoclonal antibody or antigen-binding portion thereof comprising a heavy chain variable region comprising CDR1, CDR2 and CDR3 sequences comprising an amino acid sequence selected from the group consisting of SEQ ID NOs: 4, 5, 6, 10, 11, 12, 16, 17 and 18 respectively, and a light chain variable region comprising CDR1, CDR2 and CDR3 sequences comprising an amino acid sequence selected from the group consisting of SEQ ID NOs: 7, 8, 9, 13, 14, 15, 19, 20 and 21 respectively. Thus, such antibodies contain the heavy chain variable region and light chain variable region CDR sequences of monoclonal antibodies KSN-01, KSN-02 and KSN-03, yet contain different framework sequences from these antibodies.

Such framework sequences can be obtained from public DNA databases or published references that include germline antibody gene sequences. For example, germline DNA sequences for human heavy and light chain variable region genes can be found in the "Vbase" human germline sequence database available online, as well as in Kabat, E. A., et al. (1991) Sequences of Proteins of Immunological Interest, Fifth Edition, U.S. Department of Health and Human Services, NIH Publication No. 91-3242.

TomLinson, I. M., et al. (1992) "The Repertoire of Human GermLine $V_H$ Sequences Reveals about Fifty Groups of $V_H$ Segments with Different Hypervariable Loops" /. Mol. Biol. 227:776-798; and Cox, J. P. L. et al. (1994) "A Directory of Human Germ-line $V_H$ Segments Reveals a Strong Bias in their Usage" Eur. J. Immunol. 24:827-836; the contents of each of which are expressly incorporated herein by reference.

Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al.).

Engineered antibodies described herein include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed. Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Furthermore, methionine residues in CDRs of antibodies can be oxidized, resulting in potential chemical degradation and consequent reduction in potency of the antibody. Accordingly, also provided are anti-GITR antibodies which have one or more methionine residues in the heavy and/or light chain CDRs replaced with amino acid residues which do not undergo oxidative degradation. In one embodiment, the methionine residues in the CDRs of antibodies 28F3, 18E10, 19D3, and 6G10 are replaced with amino acid residues which do not undergo oxidative degradation. Similarly, deamidation sites may be removed from anti-GITR antibodies, particularly in the CDRs.

The variable regions of the anti-HERV envelope polypeptide described herein can be linked (e.g., covalently linked or fused) to an Fc, e.g., an IgG1, IgG2, IgG3 or IgG4 Fc, which may be of any allotype or isoallotype, e.g., for IgG1: Glm, GlmL(a), Glm2(x), Glm3(f), GlmL7(z); for IgG2: G2m, G2m23(n); for IgG3: G3m, G3m21(g1), G3m28(g5), G3 mL 1(b0), G3m5(b1), G3mL3(b3), G3mL4 (b4), G3mL0(b5), G3mL5(s), G3mL6(t), G3m6(c3), G3m24(c5), G3m26(u), G3m27(v); and for K: Km, KmL, Km2, Km3 (see, e.g., Jefferies et al. (2009) mAbs 1:1). In certain embodiments, the antibodies variable regions described herein are linked to an Fc that binds to one or more activating Fc receptors (e.g. Fcγ1, Fcγ11a or Fcγ111a), and thereby stimulate ADCC and may cause T cell depletion. In certain embodiments, the antibody variable regions described herein are linked to an Fc that causes depletion.

In certain embodiments, the antibody variable regions described herein may be linked to an Fc comprising one or more modification, typically to alter one or more functional properties of the antibody, such as serum half-life, complement fixation, Fc receptor binding, and/or antigen-dependent cellular cytotoxicity. Furthermore, an antibody described herein may be chemically modified (e.g. one or more chemical moieties can be attached to the antibody) or be modified to alter its glycosylation, to alter one or more functional properties of the antibody. The numbering of residues in the Fc region is that of the EU index of Kabat.

The Fc region encompasses domains derived from the constant region of an immunoglobulin, preferably a human immunoglobulin, including a fragment, analog, variant, mutant or derivative of the constant region. Suitable immunoglobulins include IgG 1, IgG2, IgG3, IgG4, and other classes such as IgA, IgD, IgE and IgM, The constant region of an immunoglobulin is defined as a naturally-occurring or synthetically-produced polypeptide homologous to the immunoglobulin C-terminal region, and can include a CH I domain, a hinge, a CH2 domain, a CH3 domain, or a CH4 domain, separately or in combination.

The constant region of an immunoglobulin is responsible for many important antibody functions including Fc receptor (FcR) binding and complement fixation. There are five major classes of heavy chain constant region, classified as IgA, IgG, IgD, IgE, IgM, each with characteristic effector functions designated by isotype. For example, IgG is separated into four subclasses known as IgG1, IgG2, IgG3, and IgG4, Ig molecules interact with multiple classes of cellular receptors. For example IgG molecules interact with three classes of Fcy receptors (FcγR) specific for the IgG class of antibody, namely FcγRI, FcγRII, and FcγRIIL. The important sequences for the binding of IgG to the FcγR receptors have been reported to be located in the CH2 and CH3 domains. The serum half-life of an antibody is influenced by the ability of that antibody to bind to an Fc receptor (FcR).

In certain embodiments, the Fc region is a variant Fc region, e.g., an Fc sequence that has been modified (e.g., by amino acid substitution, deletion and/or insertion) relative to a parent Fc sequence (e.g., an unmodified Fc polypeptide that is subsequently modified to generate a variant), to provide desirable structural features and/or biological activity. For example, one may make modifications in the Fc region in order to generate an Fc variant that (a) has increased or decreased antibody-dependent cell-mediated cytotoxicity (ADCC), (b) increased or decreased complement mediated cytotoxicity (CDC), (c) has increased or decreased affinity for Clq and/or (d) has increased or decreased affinity for a Fc receptor relative to the parent Fc. Such Fc region variants will 47ermlin comprise at least one amino acid modification in the Fc region. Combining amino acid modifications is thought to be particularly desirable. For example, the variant Fc region may include two, three, four, five, etc. substitutions therein, e.g. of the specific Fc region positions identified herein.

A variant Fc region may also comprise a sequence alteration wherein amino acids involved in disulfide bond formation are removed or replaced with other amino acids. Such removal may avoid reaction with other cysteine-containing proteins present in the host cell used to produce the antibodies described herein. Even when cysteine residues are removed, single chain Fc domains can still form a dimeric Fc domain that is held together non-covalently. In other embodiments, the Fc region may be modified to make it more compatible with a selected host cell. For example, one may remove the PA sequence near the N-terminus of a typical native Fc region, which may be recognized by a digestive enzyme in E. coli such as proline iminopeptidase. In other embodiments, one or more glycosylation sites within the Fc domain may be removed. Residues that are typically glycosylated (e.g., asparagine) may confer cytolytic response. Such residues may be deleted or substituted with unglycosylated residues (e.g., alanine). In other embodiments, sites involved in interaction with complement, such as the Clq binding site, may be removed from the Fc region. For example, one may delete or substitute the EKK sequence of human IgG1. In certain embodiments, sites that affect binding to Fc receptors may be removed, preferably sites other than salvage receptor binding sites. In other embodiments, an Fc region may be modified to remove an ADCC site. ADCC sites are known in the art; see, for example, Molec. Immunol. 29 (5): 633-9 (1992) with regard to ADCC sites in IgG1. Specific examples of variant Fc domains are disclosed for example, in WO 97/34631 and WO 96/32478.

In one embodiment, the hinge region of Fc is modified such that the number of cysteine residues in the hinge region is altered, e.g., increased or decreased. This approach is described further in U.S. Pat. No. 5,677,425 by Bodmer et al. The number of cysteine residues in the hinge region of Fc is altered to, for example, facilitate assembly of the light and heavy chains or to increase or decrease the stability of the antibody. In one embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In yet other embodiments, the Fc region is altered by replacing at least one amino acid residue with a different amino acid residue to alter the effector function(s) of the antibody. For example, one or more amino acids selected from amino acid residues 234, 235, 236, 237, 297, 318, 320 and 322 can be replaced with a different amino acid residue such that the antibody has an altered affinity for an effector ligand but retains the antigen-binding ability of the parent antibody. The effector ligand to which affinity is altered can be, for example, an Fc receptor or the CI component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has altered Clq binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are altered to thereby alter the ability of the antibody to fix complement. This approach is described further in PCT Publication WO 94/29351 by Bodmer et al.

In yet another example, the Fc region may be modified to increase antibody dependent cellular cytotoxicity (ADCC) and/or to increase the affinity for an Fcy receptor by modifying one or more amino acids at the following positions: 234, 235, 236, 238, 239, 240, 241, 243, 244, 245, 247, 248, 249, 252, 254, 255, 256, 258, 262, 263, 264, 265, 267, 268, 269, 270, 272, 276, 278, 280, 283, 285, 286, 289, 290, 292, 293, 294, 295, 296, 298, 299, 301, 303, 305, 307, 309, 312, 313, 315, 320, 322, 324, 325, 326, 327, 329, 330, 331, 332, 333, 334, 335, 337, 338, 340, 360, 373, 376, 378, 382, 388, 389, 398, 414, 416, 419, 430, 433, 434, 435, 436, 437, 438 or 439. Exemplary substitutions include 236A, 239D, 239E, 268D, 267E, 268E, 268F, 324T, 332D, and 332E. Exemplary variants include 239D/332E, 236A/332E, 236A/239D/332E, 268F/324T, 267E/268F, 267E/324T, and 267E/268F7324T. Other modifications for enhancing FcγR and complement interactions include but are not limited to substitutions 298 A, 333A, 334A, 326A, 2471, 339D, 339Q, 280H, 290S, 298D, 298V, 243L, 292P, 300L, 396L, 3051, and 396L. These and other modifications are reviewed in Strohl, 2009, Current Opinion in Biotechnology 20:685-691.

Fc modifications that increase binding to an Fcy receptor include amino acid modifications at any one or more of amino acid positions 238, 239, 248, 249, 252, 254, 255, 256, 258, 265, 267, 268, 269, 270, 272, 279, 280, 283, 285, 298, 289, 290, 292, 293, 294, 295, 296, 298, 301, 303, 305, 307, 312, 315, 324, 327, 329, 330, 335, 337, 3338, 340, 360, 373, 376, 379, 382, 388, 389, 398, 414, 416, 419, 430, 434, 435, 437, 438 or 439 of the Fc region, wherein the numbering of the residues in the Fc region is that of the EU index as in abat (WO00/42072).

Other Fc modifications that can be made to Fcs are those for reducing or ablating binding to FcγR and/or complement proteins, thereby reducing or ablating Fc-mediated effector functions such as ADCC, ADCP, and CDC. Exemplary modifications include but are not limited substitutions, insertions, and deletions at positions 234, 235, 236, 237, 267, 269, 325, and 328, wherein numbering is according to the EU index. Exemplary substitutions include but are not limited to 234G, 235G, 236R, 237K, 267R, 269R, 325L, and 328R, wherein numbering is according to the EU index. An Fc variant may comprise 236R/328R. Other modifications for reducing FcγR and complement interactions include substitutions 297A, 234A, 235A, 237A, 318A, 228P, 236E, 268Q, 309L, 330S, 331 S, 220S, 226S, 229S, 238S, 233P, and 234V, as well as removal of the glycosylation at position 297 by mutational or enzymatic means or by production in organisms such as bacteria that do not glycosylate proteins. These and other modifications are reviewed in Strohl, 2009, Current Opinion in Biotechnology 20:685-691.

Optionally, the Fc region may comprise a non-naturally occurring amino acid residue at additional and/or alternative positions known to one skilled in the art (see, e.g., U.S. Pat. Nos. 5,624,821; 6,277,375; 6,737,056; 6,194,551; 7,317, 091; 8,101,720; PCX Patent Publications WO 00/42072; WO 01/58957; WO 02/06919; WO 04/016750; WO 04/029207; WO 04/035752; WO 04/074455; WO 04/099249; WO 04/063351; WO 05/070963; WO 05/040217, WO 05/092925 and WO 06/0201 14).

Fc variants that enhance affinity for an inhibitory receptor FcγRllb may also be used. Such variants may provide an Fc fusion protein with immune-modulatory activities related to FcγRllb cells, including for example B cells and monocytes. In one embodiment, the Fc variants provide selectively enhanced affinity to FcγRllb relative to one or more activating receptors. Modifications for altering binding to FcγRllb include one or more modifications at a position selected from the group consisting of 234, 235, 236, 237, 239, 266, 267, 268, 325, 326, 327, 328, and 332, according to the EU index. Exemplary substitutions for enhancing FcγRllb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRllb include 235Y/267E, 236D/267E, 239D/268D, 239D/267E, 267E/268D, 267E/268E, and 267E/328F.

The affinities and binding properties of an Fc region for its ligand may be determined by a variety of in vitro assay methods (biochemical or immunological based assays) known in the art including but not limited to, equilibrium methods (e.g., enzyme-linked immune-absorbent assay (ELISA), or radioimmunoassay (RIA)), or kinetics (e.g., BIACORE analysis), and other methods such as indirect binding assays, competitive inhibition assays, fluorescence resonance energy transfer (FRET), gel electrophoresis, and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental immunology, 4$^{th}$ Ed., Lippincott-Raven, Philadelphia (1999), which focuses on antibody-immunogen interactions.

In certain embodiments, the antibody is modified to increase its biological half-life. Various approaches are possible. For example, this may be done by increasing the binding affinity of the Fc region for FcRn. For example, one or more of following residues can be mutated: 252, 254, 256, 433, 435, 436, as described in U.S. Pat. No. 6,277,375. Specific exemplary substitutions include one or more of the following: T252L, T254S, and/or T256F. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary variants that increase binding to FcRn and/or improve pharmacokinetic properties include substitutions at positions 259, 308, 428, and 434, including for example 2591, 308F, 428L, 428M, 434S, 4341 1. 434F, 434Y, and 434X1. Other variants that increase Fc binding to FcRn include: 250E, 250Q, 428 L, 428F, 250Q/428L (Hinton et al, 2004, J. Biol. Chem. 279(8): 6213-6216, Hinton et al. 2006 Journal of Immunology 176:346-356), 256A, 272A, 286A, 305A, 307A, 307Q, 31 1A, 312A, 376A, 378Q, 380A, 382A, 434A (Shields et al, Journal of Biological Chemistry, 2001, 276 (9):6591-6604), 252F, 252T, 252Y, 252W, 254T, 256S, 256R, 256Q, 256E, 256D, 256T, 309P, 31 1 S, 433R, 433S, 4331, 433P, 433Q, 434H, 434F, 434Y, 252Y/254T/256E, 433K/434F/436H, 308T/309P/311S (Dall Acqua et al. Journal of Immunology, 2002, 169:5171-5180, Dall'Acqua et al., 2006, Journal of Biological Chemistry 281:23514-23524). Other modifications for modulating FcRn binding are described in Yeung et al., 2010, J Immunol, 182:7663-7671. In certain embodiments, hybrid IgG isotypes with particular biological characteristics may be used. For example, an IgG1/IgG3 hybrid variant may be constructed by substituting IgG 1 positions in the CH2 and/or CH3 region with the amino acids from IgG3 at positions where the two isotypes differ. Thus a hybrid variant IgG antibody may be constructed that comprises one or more substitutions, e.g., 274Q, 276K, 300F, 339T, 356E, 358M, 384S, 392N, 397M, 4221, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus a hybrid variant IgG antibody may be constructed chat comprises one or more substitutions, e.g., one or more of the following amino acid substitutions: 233E, 234L, 235L, −236G (referring to an insertion of a glycine at position 236), and 321 h.

Moreover, the binding sites on human IgG1 for FcγRI, FcγRII, FcγRIII and FcRn have been mapped and variants with improved binding have been described (see Shields, R. L. et al. (2001) J. Biol. Chem. 276:6591-6604). Specific mutations at positions 256, 290, 298, 333, 334 and 339 were shown to improve binding to FcγRIII. Additionally, the following combination mutants were shown to improve FcγRIII binding: T256A/S298A, S298A/E333A, S298A/K224A and S298A/E333A/K334A, which has been shown to exhibit enhanced FcγRIIIa binding and ADCC activity (Shields et al., 2001). Other IgG1 variants with strongly enhanced binding to FcγRIIIa have been identified, including variants with S239D/I332E and S239D/I332E/A330L mutations which showed the greatest increase in affinity for FcγRIIIa, a decrease in FcγRIIb binding, and strong cytotoxic activity in cynomolgus monkeys (Lazar et al., 2006). Introduction of the triple mutations into antibodies such as alemtuzumab (CD52-specific), trastuzumab (HER2/neu-specific), rituximab (CD20-specific), and cetuximab (EGFR-specific) translated into greatly enhanced ADCC activity in vitro, and the S239D/I332E variant showed an enhanced capacity to deplete B cells in monkeys (Lazar et al., 2006). In addition, IgG1 mutants containing L235V, F243L, R292P, Y300L and P396L mutations which exhibited enhanced binding to FcγRIIIa and concomitantly enhanced ADCC activity in transgenic mice expressing human FcγRIIIa in models of B cell malignancies and breast cancer have been identified (Stavenhagen et al., 2007; Nordstrom et al., 2011). Other Fc mutants that may be used include: S298A/E333A/L334A, S239D/I332E, S239D/I332E/A330L, L235V/F243L/R292P/Y300L/P396L, and M428L/N434S.

In certain embodiments, an Fc is chosen that has reduced binding to FcγRs. An exemplary Fc, e.g., IgG1 Fc, with reduced FcγR binding comprises the following three amino acid substitutions: L234A, L235E and G237A.

In certain embodiments, an Fc is chosen that has reduced complement fixation. An exemplary Fc, e.g., IgG1 Fc, with reduced complement fixation has the following two amino acid substitutions: A330S and P331S.

In certain embodiments, an Fc is chosen that has essentially no effector function, i.e., it has reduced binding to FcγRs and reduced complement fixation. An exemplary Fc, e.g., IgG1 Fc, that is effectorless comprises the following five mutations: L234A, L235E, G237A, A330S and P331S.

When using an IgG4 constant domain, it is usually preferable to include the substitution S228P, which mimics the hinge sequence in IgG1 and thereby stabilizes IgG4 molecules.

In still another embodiment, the glycosylation of an antibody is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Glycosylation of the constant region on N297 may be prevented by mutating the N297 residue to another residue, e.g., N297A, and/or by mutating an adjacent amino acid, e.g., 298 to thereby reduce glycosylation on N297.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies described herein to thereby produce an antibody with altered glycosylation. For example, EP 1,176,195 by Hanai et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Led 3 cells, with reduced ability to attach fucose to Asn(297)-linked carbohydrates, also resulting in hypofucosylation of antibodies expressed in that host cell (see also Shields, R. L. et al. (2002) J. Biol. Chem. 277:26733-26740). PCT Publication WO 99/54342 by Umana et al. describes cell lines engineered to express glycoprotein-modifying glycosyl transferases {e.g., beta(1, 4)-N-acetylglucosaminyltransferase III (GnTIII)) such that antibodies expressed in the engineered cell lines exhibit increased bisecting GlcNac structures which results in increased ADCC activity of the antibodies (see also Umana et al. (1999) Nat. Biotech. 17: 176-180).

Another modification of the antibodies described herein is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (CI-CIO) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. See for example, EP 0 154 316 by Nishimura et al. and EP0401384 by Ishikawa et al.

The present invention also encompasses a human monoclonal antibody described herein conjugated to a therapeutic agent, a polymer, a detectable label or enzyme. In one embodiment, the therapeutic agent is a cytotoxic agent. In one embodiment, the polymer is polyethylene glycol (PEG).

The anti-HERV-K antibodies may be conjugated to a cytotoxic agent, e.g. via a cleavable linker (e.g. Val-Cit linker, cleavable in vivo by Cathepsin B) or non-cleavable linker (e.g. SMCC linker). Anti-HERV-K antibodies conjugated to a cytotoxic agent comprise antibody-drug conjugates or "ADCs". ADC linkers are reviewed in Jain et al. *Pharm Res.* 2015; 32(11): 3526-2540, hereby incorporated by reference in its entirety. Cytotoxic agents include, but are not limited to, auristatins (e.g. MMAE, MMAF), matyansines, calicheamicins, centanamycin, dolastatins, duocarymycins, maytansine, pyrrolobenzodiazepine (PBD) and PBD dimers, alpha-amantin, cryptophycin, analogs of any of these, and combinations thereof. Cytotoxic agents generally comprise DNA modifying agents and microtubule disrupting agents. An overview of ADC technology can be found in Beck et al. *Nature Reviews Drug Discovery* 16, 315-337 (2017), hereby incorporated by reference in its entirety.

The anti-HERV-K Env monoclonal antibodies described herein can be produced using a variety of known techniques known in the art. One such technique is the standard somatic cell hybridization technique described by Kohler and Milstein, Nature 256: 495 (1975). Although somatic cell hybridization procedures are preferred, in principle, other techniques for producing monoclonal antibodies also can be employed, e.g., viral or oncogenic transformation of B lymphocytes, phage display technique using libraries of human antibody genes.

In one embodiment, the antibodies described herein are human monoclonal antibodies. Such human monoclonal antibodies directed against HERV-K Env can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGK monoclonal (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). The preparation and use of HuMab mice, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 821-830; Tuaillon et al. (1994) /. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.

In certain embodiments, antibodies described herein are raised using a mouse that carries human immunoglobulin sequences on transgenes and transchomosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-HERV-K Env antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-HERV-K Env antibodies described herein. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-GITR antibodies described herein.

Additional mouse systems described in the art for raising human antibodies, e.g., human anti-GITR antibodies, include (i) the VelocImmune® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains unrearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies described herein can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

To generate fully human antibodies to GITR, transgenic or transchromosomal mice containing human immunoglobulin genes (e.g., Hco12, Hco7 or KM mice) can be immunized with a purified or enriched preparation of the HERV-K Env antigen and/or cells expressing HERV-K Env or fragment thereof, as described for other antigens, for example, by Lonberg et al. (1994) Nature 368(6474): 856-859; Fishwild et al. (1996) Nature Biotechnology 14: 845-851 and WO 98/24884. Alternatively, mice can be immunized with DNA encoding HERV-K Env or fragment thereof. Preferably, the mice will be 6-16 weeks of age upon the first infusion. For example, a purified or enriched preparation (5-50 µg) of the recombinant HERV-K Env antigen can be used to immunize the HuMAb mice intraperitoneally. In the event that immunizations using a purified or enriched preparation of the HERV-K Env antigen do not result in antibodies, mice can also be immunized with cells expressing HERV-K Env, e.g., a cell line, to promote immune responses.

Nucleic Acids, Vectors, Vector Systems, and Cells

Some embodiments of the invention are directed to vectors and vector systems containing nucleotide sequences that code for the variable regions of anti-HER-K antibodies, e.g. KSN-01, KSN-02, and KSN-03, as well as cells transformed with such vectors and/or vector systems. The vector may be, for example but not necessarily, a plasmid; other explicitly non-limiting recombinant vectors are known in the art and may include, e.g. phage vectors such as a λ phage vector, other viral vectors such as non-replicating adenoviral vector, lentiviral vector, pSV, pCMV series of plasmid vectors, vaccinia and retroviral vectors, baculoviral vectors, cosmids, artificial chromosomes. The vector may be a mammalian expression vectors; for example, vectors may be transfected into mammalian cells and the DNA may be integrated into the genome by homologous recombination in the case of stable transfection, or alternatively the cells may be transiently transfected. Common to most engineered vectors are origin of replications, multicloning sites, and selectable markers, so as long as a vector (including systems of vectors, e.g. multiple plasmids) contain such a system they are considered to be covered by the scope of this invention. Common promoters for mammalian expression vectors include CMV and SV40 promoters; nonviral promoters such as EF-1 promoters are also known. In some embodiments, the present disclosure is directed to a vector or system of vectors containing one or more nucleic acid sequences encoding one or more CDRs of one or more heavy and/or light chains of one or more of the anti-HERV-K antibodies of the present disclosure, e.g. nucleotide sequence or sequences coding for one or more of SEQ ID NOs 4-21. These nucleotides coding for CDRs may share a certain degree of homology (i.e. at least 75%, at least 80%, at least 85%, at least 90%, at least 95%, or more than 95%) with the nucleotide sequences coding for the CDRs within any one of SEQ ID NOs: 28-33.

The nucleic acid sequences may have conservative substitutions, and may be codon optimized. As used herein, codon optimization refers to an in vitro mutagenesis of a nucleic acid to increase or maximize expression of a gene (e.g. a transgene relative to the unmodified nucleic acid, without changing (or with minimal change) to the amino acid sequence of the synthesized protein, i.e. synonymous mutations. Codon optimization can affect protein expression rates up to 1,000× fold, particularly by favoring efficient soluble protein expression. The codons changed are typically ones not generally used by the host cell translation system. Codon bias/codon usage frequency depends on the host organism, and is described, for example, in U.S. Pat. No. 8,326,547, hereby incorporated by reference in its entirety.

A vector or vector system that codes for one or both variable region(s) of KSN-01 may contain one of or both of SEQ ID NO: 28 and SEQ ID NO: 29 or a nucleotide sequence or sequences that shares or share a degree of homology with SEQ ID NO: 28 and/or SEQ ID NO: 29, e.g. at least 75% homology, at least 80% homology, at least 85% homology, at least 90% homology, at least 95%, or more than 95% homology with either or both of SEQ ID NO: 28 and SEQ ID NO: 29. A vector or vector system that codes for one or both variable region(s) of KSN-02 may contain one of or both of SEQ ID NO: 30 and SEQ ID NO: 31 or a nucleotide sequence or sequences that shares or share a degree of homology with SEQ ID NO: 30 and/or SEQ ID NO: 31, e.g. at least 75% homology up to, at least 80% homology, at least 85% homology at least 90% homology, at least 95%, or more than 95% homology either or both of SEQ ID NO: 30 and SEQ ID NO: 31. A vector or vector system that codes for one or both variable region(s) of KSN-03 may contain one of or both of SEQ ID NO: 32 and SEQ ID NO: 33 or a nucleotide sequence or sequences that shares or share a degree of homology with SEQ ID NO: 32 and/or SEQ ID NO: 33, e.g. at least 75% homology up to, at least 80% homology, at least 85% homology at least 90% homology, at least 95%, or more than 95% homology either or both of SEQ ID NO: 32 and SEQ ID NO: 33. The nucleotide sequences coding for the variable regions, e.g. of KSN-01, KSN-02 and/or KSN-03 may or may not be on the same vector. Such a system may allow for greater control of expression, for example, by allowing for the expression of the variable light and/or heavy chain to be separately inducible.

Some embodiments of the present disclosure are directed to methods of making a recombinant anti-HERV-K antibody in a host cell. The transformed host cell will then be induced to produce the recombinant antibodies, which may assemble the antibodies from heavy/light chains in the host cell and then transport the antibodies out of the cell, or the antibodies may self-assemble outside the host cell and be exported as heavy/light chains. Common host cells may include yeast cells, e.g. *S. cerevisiae, S. pombe* and *P. pastoris*, bacteria, e.g. *E. coli*, and mammalian cells, e.g. Chinese hamster ovary (CHO) cells, including DUXB11, DG44 and CHOK1 lineages, NS0 murine myeloma cells, PER.C6 human cells, and human embryonic kidney (HEK) cells, e.g. HEK293, which is used in Example 1 infra. An overview of cell culture processes for recombinant monoclonal antibody production may be found in Li et al. Cell culture processes for monoclonal antibody production, Mabs. 2010 September-October; 2(5): 466-477.

One of ordinary skill in the art will appreciate that different cell types may lead to different antibody products and may possibly impact the therapeutic efficacy of the antibody products, e.g. through having distinct variations in glycosylation patterns, especially N-linked glycosylation patterns. Such discussions may be found in Liu L, Antibody glycosylation and its impact on the pharmacokinetics and pharmacodynamics of monoclonal antibodies and Fc-fusion proteins, *J Pharm Sci.* 2015 June; 104(6):1866-84 as well as Sha et al., N-Glycosylation Design and Control of Therapeutic Monoclonal Antibodies, published online Mar. 22, 2016, Rosenlöcher et al. Recombinant glycoproteins: The impact of cell lines and culture conditions on the generation of protein species *J Proteomics.* 2016 Feb. 16; 134:85-92, Mimura et al., Enhanced sialylation of a human chimeric IgG1 variant produced in human and rodent cell lines, *J Immunol Methods.* 2016 January; 428:30-6, and Croset et al., Differences in the glycosylation of recombinant proteins expressed in HEK and CHO cells, *Journal of Biotechnology*, 161(3), Oct. 31, 2012, all references hereby incorporated by reference in their entireties. Recombinant antibody production may include heavy and/or light chains on the same or different vectors, and may or may not concomitantly expressed.

Other less common host cells, but still included within the scope of the invention, include plant cells, for example, those based on the Ti plasmid of *Agrobacterium tumefaciens*. Cell-free expression systems also exist, for example, based on *E. coli* cell lysate, containing cellular components necessary for transcription/translation. Eukaryotic and mammalian cell-free systems are also known in the art, for example wheat germ cell-free expression system, and those described in Brodel et al. (2015), *Methods Mol Bio.* 1261: 129-40, hereby incorporated by reference in its entirety. Some recombinant antibody production systems express the recombinant antibodies on the surface of the host cell before harvesting, others simply release the antibodies into a medium for collection. Such variations are intended to be within the scope of the present disclosure.

Pharmaceutical Compositions, Formulations, and Devices

In another aspect, the present invention provides a pharmaceutical composition comprising the antibodies of the present invention described herein formulated together with a pharmaceutically acceptable carrier. The composition may optionally contain one or more additional pharmaceutically active ingredients, such as another antibody or a therapeutic agent. The pharmaceutical compositions of the invention also can be administered in a combination therapy with, for example, another immune-stimulatory agent, anti-cancer agent, an antiviral agent, or a vaccine, etc. In certain embodiments, a composition comprises an anti-HERV-K Env antibody at a concentration of at least 1 mg/mL, 5 mg/mL, 10 mg/mL, 50 mg/mL, 100 mg/mL, 150 mg/mL, 200 mg/mL, 1-300 mg/mL, or 100-300 mg/mL.

The pharmaceutical composition can comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: The Science and Practice of Pharmacy, 20$^{th}$ Ed. (Lippincott Williams & Wilkins 2003), the disclosure of which is incorporated herein by reference.

Preferably, a pharmaceutical composition is suitable for intravenous, intramuscular, subcutaneous, parenteral, spinal or epidermal administration (e.g., by injection or infusion). Depending on the route of administration, the active compound can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the present invention described herein can be administered via a non-parenteral route, such as a topical, epidermal or mucosal route of administration, e.g., intranasally, orally, vaginally, rectally, sublingually or topically.

The pharmaceutical composition of the invention can be in the form of pharmaceutically acceptable salts. A "pharmaceutically acceptable salt" refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The pharmaceutically acceptable composition may be in liquid form or solid form. A solid formulation is generally, but not necessarily, lyophilized and brought into solution prior to administration for either single or multiple dosing. The formulations should not be exposed to extreme temperature or pH so as to avoid thermal denaturation. Thus, it is essential to formulate an antibody composition of the present disclosure within a biologically relevant pH range. A solution buffered to maintain a proper pH range during storage is often necessary, especially for liquid formulations stored for longer periods of time between formulation and administration. Typically, both liquid and solid formulations require storage at lower temperatures (usually 2-8° C.) in order to retain stability for longer periods. Formulated antibody compositions, especially liquid formulations, may contain a bacteriostat to prevent or minimize proteolysis during storage, including but not limited to effective concentrations (usually <1% w/v) of benzyl alcohol, phenol, m-cresol, chlorobutanol, methylparaben, and/or propylparaben. A bacteriostat may be contraindicated for some patients. Therefore, a lyophilized formulation may be reconstituted in a solution either containing or not containing such a component. Additional components may be added to either a buffered liquid or solid antibody formulation, including but not limited to sugars as a cryoprotectant (including but not necessarily limited to polyhydroxy hydrocarbons such as sorbitol, mannitol, glycerol and dulcitol and/or disaccharides such as sucrose, lactose, maltose or trehalose) and, in some instances, a relevant salt (including but not limited to NaCl, KCl or LiCl). Such antibody formulations, especially liquid formulations slated for long term storage, will rely on a useful range of total osmolarity to both promote long term stability at temperature of 2-8° C., or higher, while also making the formulation useful for parenteral injection. For example, but not necessarily, an effective range of total osmolarity (the total number of molecules in solution) may be from about 200 mOs/L to about 800 mOs/L. It will be apparent that the amount of a cyroprotectant, such as sucrose or sorbitol, will depend upon the amount of salt in the formulation in order for the total osmolarity of the solution to remain within an appropriate range. Therefore a salt free formulation may, but not necessarily, contain from about 5% to about 25% sucrose.

Alternatively, a salt free sorbitol-based formulation may, but not necessarily, contain sorbitol within a range from about 3% to about 12%. Salt-free formulations will of course warrant increased ranges of the respective cryoprotectant in order to maintain effective osmolarity levels. These formulation may also contain a divalent cation (including but not necessarily limited to $MgCl_2$, $CaCl_2$) and $MnCl_2$); and a non-32 ionic surfactant (including but not necessarily limited to Polysorbate-80 (Tween 80®), Polysorbate-60 (Tween 60®), Polysorbate-40 (Tween 40®) and Polysorbate-20 (Tween 20®), polyoxyethylene alkyl ethers, including but not limited to Brij 58®, Brij 35®, as well as others such as Triton X-100®, Triton X 114®, NP40®, Span 85 and the Pluronic series of non-ionic surfactants (e.g., Pluronic 121)). Any combination of such components, including probable inclusion of a bacteriostat, may be useful to fill the antibody-containing formulations of the present disclosure. The anti-HERV-K antibodies or antigen-binding portions thereof of the present disclosure may also be a "chemical derivative", which describes antibodies that contain additional chemical moieties which are not normally a part of the immunoglobulin molecule (e.g., pegylation). Such moieties may improve the solubility, half-life, absorption, etc. of the base molecule. Alternatively the moieties may attenuate undesirable side effects of the base molecule or decrease the toxicity of the base molecule.

The pharmaceutical composition of the present invention can be in the form of sterile aqueous solutions or dispersions. It can also be formulated in a microemulsion, liposome, or other ordered structure suitable to high drug concentration.

An antibody of the present invention described herein can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The amount of active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient, preferably from about 0.1% to about 70%, most preferably from about 1% to about 30% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. Alternatively, antibody can be administered as a sustained release formulation, in which case less frequent administration is required. For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-HERV-K Env antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks. In some methods, dosage is adjusted to achieve a plasma antibody concentration of about 1-1000 μg/mL and in some methods about 25-300 μg/mL. A "therapeutically effective dosage" of an anti-HERV-K Env antibody of the invention preferably results in a decrease in severity of disease symptoms, an increase in frequency and duration of disease symptom-free periods, or a prevention of impairment or disability due to the disease affliction. For example, for the treatment of HIV infection in a subject, a "therapeutically effective dosage" preferably inhibits HIV virus replication or uptake by host cells by at least about 20%, more preferably by at least about 40%, even more preferably by at least about 60%, and still more preferably by at least about 80% relative to untreated subjects. A therapeutically effective amount of a therapeutic compound can neutralize HIV virus, or otherwise ameliorate symptoms in a subject, which is typically a human or can be another mammal. The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparati (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the human monoclonal antibodies of the invention described herein can be formulated to ensure proper distribution in vivo. For example, to ensure that the therapeutic compounds of the invention cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) /. Clin. Pharmacol. 29:685; Umezawa et al, (1988) Biochem. Biophys. Res. Commun. 153:1038; Bloeman et al. (1995) FEBS Lett. 357:140; M. Owais et al. (1995) Antimicrob. Agents Chemother. 39:180; Briscoe et al. (1995) Am. /. Physiol. 1233:134; Schreier et al. (1994) /. Biol. Chem. 269:9090; Keinanen and Laukkanen (1994) FEBS Lett. 346:123; and Killion and Fidler (1994) Immunomethods 4:273.

Specific embodiments for delivery vehicles for anti-HERV-K antibodies of the present disclosure include PLGA microspheres, as discussed herein and as further known in the art, as well as polymer-based non-degradable vehicles comprising poly (ethylene-co-vinyl acetate; PEVAc). Additionally, controlled-release and localized delivery of antibody-based therapeutic products is reviewed in Grainger, et al., 2004, Expert Opin. Biol. Ther. 4(7): 1029-1044), hereby incorporated by reference in its entirety. Suitable microcapsules capable of encapsulating the antibody may also include hydroxymethylcellulose or gelatin-microcapsules and polymethyl methacrylate microcapsules prepared by coacervation techniques or by interfacial polymerization. See PCT publication WO 99/24061 entitled "Method for Producing IGF-1 Sustained-Release Formulations," wherein a protein is encapsulated in PLGA microspheres, this reference which is hereby incorporated herein by reference in its entirety. In addition, microemulsions or colloidal drug delivery systems such as liposomes and albumin microspheres, may also be used. Other preferred sustained-release compositions employ a bioadhesive to retain the antibody at the site of administration. As noted above, the sustained-release formulation may comprise a biodegradable polymer into which the antibody is disposed, which may provide for non-immediate release. Non-injectable devices may be described herein as an "implant", "pharmaceutical depot implant", "depot implant", "non-injectable depot" or some such similar term. Common depot implants may include, but are not limited to, solid biodegradable and non-biodegradable polymer devices (such as an extended polymer or coaxial rod shaped device), as well as numerous pump systems also known in the art. Injectable devices are split into bolus injections (release and dissipation of the drug subsequent to injection), and repository or depot injections, which provide a storage reservoir at the site of injection, allowing for sustained-release of the biological agent over time. A depot implant may be surgically tethered to the point of delivery so as to provide an adequate reservoir for the prolonged release of the antibody over time. Such a device will be capable of carrying the drug formulation in such quantities as therapeutically or prophylactically required for treatment over the pre-selected period. The depot implant may also provide protection to the formulation from degradation by body processes (such as proteases) for the duration of treatment. As known in the art, the term "sustained-release" refers to the gradual (continuous or discontinuous) release of such an agent from the block polymer matrix over an extended period of time. Regardless of the specific device, the sustained-release of the composition will result in a local biologically effective concentrations of the antibody. A sustained release of the biological agent(s) will be for a period of a single day, several days, a week or more; but most likely for a month or more, or up to about six months, depending on the formulation. Natural or synthetic polymers known in the art will be useful as a depot implant due to characteristics such as versatile degradation kinetics, safety, and biocompatibility. These copolymers can be manipulated to modify the pharmacokinetics of the active ingredient, shield the agent from enzymatic attack, as well as degrading over time at the site of attachment or injection. The artisan will understand that there are ample teachings in the art to manipulate the properties of these copolymers, including the respective production process, catalysts used, and final molecular weight of the sustained-release depot implant or depot injection. Natural polymers include but are not limited to proteins (e.g., collagen, albumin or gelatin); polysaccharides (cellulose, starch, alginates, chitin, chitosan, cyclodextrin, dextran, hyaluronic acid) and lipids. Biodegradable synthetic polymers may include but are not limited to various polyesters, copolymers of L-glutamic acid and gamma ethyl-L-glutamate (Sidman et al., 1983, Biopolymers 22:547-556), polylactides ([PLA]; U.S. Pat. No. 3,773, 919 and EP 058,481), polylactate polyglycolate (PLGA) such as polylactide-co-glycolide (see, for example, U.S. Pat. Nos. 4,767,628 and 5,654,008), polyglycolide (PG), polyethylene glycol (PEG) conjugates of poly($\alpha$-hydroxy acids), polyorthoesters, polyaspirins, polyphosphagenes, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, polyorthoesters (POE), or any combinations thereof, as described above (see, for example, U.S. Pat. No. 6,991,654 and U.S. Pat. Appl. No. 20050187631, each of which is incorporated herein by reference, hydrogels (see, for example, Langer et al., 1981, J. Biomed. Mater. Res. 15:167-277; Langer, 1982, Chem. Tech. 12:98-105, non-degradable ethylene-vinyl acetate (e.g. ethylene vinyl acetate disks and poly(ethylene-co-vinyl acetate)), degradable lactic acid-glycolic acid r such as the Lupron Depot™, poly-D-(−)-3-hydroxybutyric acid (EP 133,988), hyaluronic acid gels (see, for example, U.S. Pat. No. 4,636,524), alginic acid suspensions, polyorthoesters (POE), and the like. Polylactide (PLA) and its copolymers with glycolide (PLGA) have been well known in the art since the commercialization of the Lupron Depot™, approved in 1989 as the first parenteral sustained-release formulation utilizing PLA polymers. Additional examples of products which utilize PLA and PLGA as excipients to achieve sustained-release of the active ingredient include Amidox (PLA; periodontal disease), Nutropin Depot (PLGA; with hGH), and the Trelstar Depot (PLGA; prostate cancer). Other synthetic polymers included but are not limited to poly(c-caprolactone), poly3-hydroxybutyrate, poly($\beta$-malic acid) and poly(dioxanone)]; polyanhydrides, polyurethane (see WO 2005/013936), polyamides, cyclodestrans, polyorthoesters, n-vinyl alcohol, polyethylene oxide/polyethylene terephthalate, polyphosphate, polyphosphonate, polyorthoester, polycyanoacrylate, polyethylenegylcol, polydihydropyran, and polyacytal. Non-biodegradable devices include but are not limited to various cellulose derivatives (carboxymethyl cellulose, cellulose acetate, cellulose acetate propionate, ethyl cellulose, hydroxypropyl methyl cellulose) silicon-based implants (polydimethylsiloxane), acrylic polymers, (polymethacrylate, polymethylmethacrylate, polyhydroxy(ethylmethylacrylate), as well as polyethylene-co-(vinyl acetate), poloxamer, polyvinylpyrrolidone, poloxamine, polypropylene, polyamide, polyacetal, polyester, poly ethylene-chlorotrifluoroethylene, polytetrafluoroethylene (PTFE or "Teflon™"), styrene butadiene rubber, polyethylene, polypropylene, polyphenylene oxide-polystyrene, poly-a-chloro-p-xylene, polymethylpentene, polysulfone and other related biostable polymers. Carriers suitable for sustained-release depot formulations include, but are not limited to, films, capsules, particles, gels, coatings, matrices, wafers, pills or other pharmaceutical delivery compositions. Examples of such sustained-release formulations are described above. See also U.S. Pat. Nos. 6,953,593; 6,946,146; 6,656,508; 6,541,033; and 6,451,346, the contents of each which are incorporated herein by reference. The dosage form must be capable of carrying the drug formulation in such quantities and concentration as therapeutically required for treatment over the pre-selected period, and must provide sufficient protection to the formulation from degradation by body processes for the duration of treatment. For example, the dosage form can be surrounded by an exterior made of a material that has properties to protect against degradation from metabolic processes and the risk of, e.g., leakage, cracking, breakage, or distortion. This can prevent expelling of the dosage form contents in an uncontrolled manner under stresses it would be subjected to during use, e.g., due to physical forces exerted upon the drug release device as a result of normal joint articulation and other movements by the subject or for example, in convective drug delivery devices, physical forces associated with pressure generated within the reservoir. The drug reservoir or other means for holding or containing the drug must also be of such material as to avoid unintended reactions with the active agent formulation, and is preferably biocompatible (e.g., where the dosage form is implanted, it is substantially non-reactive with respect to a subject's body or body fluids).

The present compositions may be used in an immunogenic composition to immunize an animal. Such immunogenic composition according to the invention may be used for the preparation of a vaccine. Preferably a prophylactic and/or therapeutic vaccine is produced. Thus, within the scope of this invention is an immunogenic or vaccine composition that contains a pharmaceutically acceptable carrier and an effective amount of an antigen as described supra. The carriers used in the composition can be selected on the basis of the mode and route of administration, and standard pharmaceutical practice. The composition can also contain an adjuvant. Examples of an adjuvant include a cholera toxin, *Escherichia coli* heat-labile enterotoxin, liposome, unmethylated DNA (CpG) or any other innate immune-stimulating complex. Various adjuvants that can be used to further increase the immunological response depend on the host species and include Freund's adjuvant (complete and incomplete), mineral gels such as aluminum hydroxide, surface-active substances such as lysolecithin, pluronic polyols, polyanions, peptides, oil emulsions, keyhole limpet hemocyanin, and dinitrophenol.

A vaccine formulation may be administered to a subject per se or in the form of a pharmaceutical or therapeutic composition. Compositions of the invention and an adjuvant may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the antigens of the invention into preparations which can be used pharmaceutically. Proper formulation is dependent upon the route of administration chosen.

For injection, vaccine preparations may be formulated in aqueous solutions, preferably in physiologically compatible buffers such as Hanks' solution, Ringer's solution, phosphate buffered saline, or any other physiological saline buffer. The solution may contain formulatory agents such as suspending, stabilizing and/or dispersing agents. Alternatively, the composition may be in powder form for constitution with a suitable vehicle, e.g., sterile pyrogen-free water, before use.

The amount of a composition administered depends, for example, on the particular antigen in the composition, whether an adjuvant is co-administered with the antigen, the type of adjuvant co-administered, the mode and frequency of administration, and the desired effect (e.g., protection or treatment), as can be determined by one skilled in the art. Determination of an effective amount of the vaccine formulation for administration is well within the capabilities of those skilled in the art, especially in light of the detailed disclosure provided herein. An effective dose can be estimated initially from in vitro assays. For example, a dose can be formulated in animal models to achieve an induction of an immune response using techniques that are well known in the art. One having ordinary skill in the art could readily optimize administration to all animal species based on results described herein. Dosage amount and interval may be adjusted individually. For example, when used as a vaccine, the vaccine formulations of the invention may be administered in about 1 to 3 doses for a 1-36 week period. Preferably, 1 or 2 doses are administered, at intervals of about 3 weeks to about 4 months, and booster vaccinations may be given periodically thereafter. Alternative protocols may be appropriate for individual animals. A suitable dose is an amount of the vaccine formulation that, when administered as described above, is capable of raising an immune response in an immunized animal sufficient to protect the animal from an infection for at least 4 to 12 months. In general, the amount of the antigen present in a dose ranges from about 1 pg to about 100 mg per kg of host, typically from about 10 pg to about 1 mg, and preferably from about 100 pg to about 1 pg. Suitable dose range will vary with the route of injection and the size of the subject, but will typically range from about 0.1 mL to about 5 mL. Additional boosters can be given as needed.

Therapeutic and Diagnostic Methods

In another aspect, the anti-HERV-K Env antibodies described herein can be used to neutralize HIV virus. The neutralizing of the HIV virus can be done via (i) inhibiting HIV virus binding to a target cell; (ii) inhibiting HIV virus uptake by a target cell; (iii) inhibiting HIV virus replication; and (iv) inhibiting HIV virus particles release from infected cells. One skilled in the art possesses the ability to perform any assay to assess neutralization of HIV virus. Notably, the neutralizing properties of antibodies may be assessed by a variety of tests, which all may assess the consequences of (i) inhibition of HIV virus binding to a target cell; (ii) inhibition of HIV virus uptake by a target cell; (iii) inhibition of HIV virus replication; and (iv) inhibition of HIV virus particles release from infected cells. In other words, implementing different tests may lead to the observation of the same consequence, i.e. the loss of infectivity of the HIV virus. Thus, in one embodiment, the present invention provides a method of neutralizing HIV virus in a subject comprising administering to the subject a therapeutically effect amount of the antibody of the present invention described herein.

Another aspect of the present invention provides a method of treating a HIV-based disease. Such method includes therapeutic (following HIV infection) and prophylactic (prior to HIV exposure, infection or pathology). For example, therapeutic and prophylactic methods of treating an individual for a HIV infection include treatment of an individual having or at risk of having a HIV infection or pathology, treating an individual with a HIV infection, and methods of protecting an individual from a HIV infection, to decrease or reduce the probability of a HIV infection in an individual, to decrease or reduce susceptibility of an individual to a HIV infection, or to inhibit or prevent a HIV infection in an individual, and to decrease, reduce, inhibit or suppress transmission of a HIV from an infected individual to an uninfected individual. Such methods include administering an antibody of the present invention or a composition comprising the antibody disclosed herein to therapeutically or prophylactically treat (vaccinate or immunize) an individual having or at risk of having a HIV infection or pathology. Accordingly, methods can treat the HIV infection or pathology, or provide the individual with protection from infection (e.g., prophylactic protection).

In one embodiment, a method of treating a HIV-based disease comprises administering to an individual in need thereof an anti-HERV-K Env antibody or therapeutic composition disclosed herein in an amount sufficient to reduce one or more physiological conditions or symptom associated with a HIV infection or pathology, thereby treating the HIV-based disease.

The anti-HERV-K antibodies or antigen-binding portions thereof of the present disclosure may be co-administered with one or more additional treatments for HIV, e.g. co-administered with one or more antivirals and/or additional anti-HIV antibodies or antigen-binding portions thereof, including but not limited to additional anti-HERV-K antibodies or antigen-binding portions thereof of the present disclosure. Anti-HIV antibodies may include, but are not limited to, broadly neutralizing anti-HIV antibodies, for example, those disclosed in, e.g. Shcherbakov et al. *Acta Naturae* 2015 October-December; 7(4): 11-21, hereby incorporated by reference in its entirety, for example, VRC01 and VRC01-like antibodies (targeting CD4 binding site), PG9 and PG16 recognition site, those targeting the V3 loop region, MPER region, gp120/gp41 interface region, and combinations thereof. Suitable antivirals include traditional antiretrovirals such as reverse transcriptase inhibitors, for example but not limited to nucleoside RT inhibitors and nucleotide RT inhibitors such as lamivudine, abacavir, zidovudine, stavudine, zalcitabine, didaonsine, emtricitabine, tenofovir and combinations thereof, protease inhibitors, including but not limited to amprenavir, atazanavir, darunavir, fosamprenavir, indinavir, lopinavir/ritonavir, nelfinavir, ritonavir, saquinavir, tipranavir and combinations thereof, entry inhibitors, fusion inhibitors such as T-20 (enfuvirtide), CCR5 antagonists such as maraviroc, CXCR4 antagonists, integrase inhibitors, maturation inhibitors, assembly inhibitors such as bevirimat, and combinations of such antiviral compounds.

In one embodiment, an anti-HERV-K Env antibody or therapeutic composition disclosed herein is used to treat a HIV-based disease. Use of an anti-HERV Env antibody or therapeutic composition disclosed herein treats a HIV-based disease by reducing one or more physiological conditions or symptom associated with a HIV infection or pathology. In aspects of this embodiment, administration of an anti-HERV-K antibody/antigen-binding portion or therapeutic composition disclosed herein is in an amount sufficient to reduce one or more physiological conditions or symptom associated with a HIV infection or pathology, thereby treating the HIV-based disease. In other aspects of this embodiment, administration of an anti-HERV-K or therapeutic composition disclosed herein is in an amount sufficient to increase, induce, enhance, augment, promote or stimulate HIV clearance or removal; or decrease, reduce, inhibit, suppress, prevent, control, or limit transmission of HIV to another individual.

One or more physiological conditions or symptom associated with a HIV infection or pathology will respond to a method of treatment disclosed herein. The symptoms of HIV infection or pathology vary, depending on the phase of infection: primary or acute HIV infection, clinical latent infection, early symptomatic HIV infection, and AIDS. The majority of people infected by HIV develop a flu-like illness within a month or two after the virus enters the body. This illness, known as primary or acute HIV infection, may last for a few weeks. Although the symptoms of primary HIV infection may be mild enough to go unnoticed, the amount of virus in the blood stream (viral load) is particularly high at this time. As a result, HIV infection spreads more efficiently during primary infection than during the next stage of infection. Possible symptoms include fever, muscle soreness, rash, headache, sore throat, mouth or genital ulcers, swollen lymph glands, mainly on the neck, joint pain, night sweats, and diarrhea. In some individuals, persistent swelling of lymph nodes occurs during clinical latent HIV. Otherwise, there are no specific signs and symptoms. HIV remains in the body, however, as free virus and in infected white blood cells. Clinical latent infection typically lasts eight to 10 years. A few individuals stay in this stage even longer, but others progress to more-severe disease much sooner. As the virus continues to multiply and destroy immune cells, an individual may develop mild infections or chronic symptoms such as fever, fatigue, swollen lymph nodes, often one of the first signs of HIV infection, diarrhea, weight loss, cough, and shortness of breath. The disease typically progresses to AIDS in about 10 years. By the time AIDS develops, the immune system has been severely damaged, making the individual susceptible to opportunistic infections, diseases that wouldn't trouble an individual with a healthy immune system. The signs and symptoms of some of these infections may include soaking night sweats, shaking chills, fever higher, cough, shortness of breath, chronic diarrhea, persistent white spots or lesions on tongue or in mouth, headaches, persistent, unexplained fatigue, blurred and distorted vision, weight loss, skin rashes, or skin bumps.

In another aspect of the present invention, the anti-HERV-K Env antibody or therapeutic composition disclosed herein is used to treat a cellular proliferative disorder, e.g. cancer. For example, in one embodiment, the anti-HERV-K antibody is used to treat cancer, e.g. pancreatic cancer, breast cancer, melanoma, hepatocellular carcinoma, ovarian cancer, leukemia, lymphoma, germ cell tumors, prostate cancer, and combinations thereof, based on the known expression/suggested role of HERV-K Env in the tumorigenesis of these cancer types. The anti-HERV-K antibody may be administered with a chemotherapeutic agent, for example, in the form of an antibody-drug conjugate (ADC) as disclosed herein, or co-administered with one or more chemotherapeutic agents.

More specifically, regarding pancreatic cancers, see, e.g. Li et al. *Clin Cancer Res.* 2017 and Schmitz-Winnenthal et al. *Cancer Lett.* 2007 Jul. 18; 252(2):290-8, both references hereby incorporated by reference in their entireties. Regarding breast cancers, see, e.g. Johanning et al. *Sci Rep.* 2017; 7: 41960, Lamaitre et al. *PLoS Pathog.* 2017 June; 13(6), Zhou et al., *Oncotarget.* 2016 Dec. 20; 7(51): 84093-84117, Rhyu et al. *Int J Mol Sci.* 2014 June; 15(6): 9173-9183, Wang-Johanning et al. *J Natl Cancer Inst.* 2012 Feb. 8; 104(3): 189-210, and Zheo et al. *Genes Cancer.* 2011 September; 2(9): 914-922, each reference hereby incorporated by reference in its entirety. Regarding melanoma, see, e.g., Argaw-Denboba et al., *J Exp Clin Cancer Res.* 2017; 36: 20, Schmitt et al., *Genome Biol Evol.* 2013; 5(2): 307-328, Schanab et al. *Pigment Cell Melanoma Res.* 2011 August; 24(4):656-65, Hahn S et al. *AIDS Res Hum Retroviruses.* 2008 May; 24(5):717-23, and Büscher K et al., *Melanoma Res.* 2006 June; 16(3):223-34, each reference hereby incorporated by reference in its entirety. Regarding hepatocellular carcinoma, see, e.g., Ma et al., *Biomed Res Int.* 2016; 2016: 8201642, hereby incorporated by reference in its entirety. Regarding ovarian cancer, see, e.g., Rycaj K et al., *Clin Cancer Res.* 2015 Jan. 15; 21(2):471-83 and Wang-Johanning et al., *Int J Cancer.* 2007 Jan. 1; 120(1): 81-90, both references hereby incorporated by reference in their entireties. Regarding leukemia and lymphoma, see, e.g., Chen T et al., *Leukemia.* 2013 July; 27(7):1469-78, Januszkiewicz-Lewandowska D et al., *Acta Haematol.* 2013; 129(4):232-7, and Contreras-Galindo et al., *J Virol.* 2008 October; 82(19): 9329-9336, each reference hereby incorporated by reference in its entirety. Regarding germ cell tumors, see, e.g., Kleiman et al., *Int J Cancer.* 2004 Jun. 20; 110(3):459-61, Herbst et al., *APMIS.* 1998 January; 106(1): 216-20, and Herbst et al. *Am J Pathol.* 1996 November; 149(5): 1727-1735, each reference hereby incorporated by reference in its entirety. Regarding prostate cancer, see, e.g., Wallace et al., *Carcinogenesis.* 2014 September; 35(9): 2074-2083 and Goering et al., *Prostate.* 2015 December; 75(16):1958-71, both references hereby incorporated by reference in their entireties.

In another aspect of the present invention, the anti-HERV-K Env antibody or therapeutic composition disclosed herein is used to treat an autoimmune, neurological, and/or metabolic-related disorder, based on known descriptions of HERV-K Env expression and/or immune-responses against HERV-K Env being altered in such disorders. The anti- HERV-K antibodies may be administered with, e.g., an immunosuppressant. The autoimmune, neurological, and/or metabolic-related disorder may be, e.g., rheumatoid arthritis (RA), systemic lupus erythematosus (SLE), psoriasis, morphea, multiple sclerosis (MS), myalgic encephalomyelitis, amyotrophic lateral sclerosis (ALS), and combinations thereof. More specifically, regarding rheumatoid arthritis (RA), see, e.g., Reynier et al., *Scand J Immunol.* 2009 September; 70(3):295-9, hereby incorporated by reference in its entirety. Regarding systemic lupus erythematosus (SLE), see, e.g., Herve et al., *Clin Exp Immunol.* 2002 April; 128(1): 75-82, hereby incorporated by reference in its entirety. Regarding psoriasis, see, e.g., Gupta et al., *J Transl Med.* 2014; 12: 256 and Lai et al., *J Invest Dermatol.* 2012 July; 132(7): 1833-1840, both references hereby incorporated by reference in their entireties. Regarding morphea, see, e.g., Kowalczyk et al., *Arch Med Sci.* 2012 Nov. 9; 8(5): 819-825, hereby incorporated by reference in its entirety. Regarding multiple sclerosis (MS), see, e.g., Morandi et al., *PLoS One.* 2017; 12(2): e0172415, hereby incorporated by reference in its entirety. Regarding myalgic encephalomyelitis, see, e.g., De Meirleir et al., *In Vivo.* 2013 March-April; 27(2): 177-187, hereby incorporated by reference in its entirety. Regarding amyotrophic lateral sclerosis (ALS), see, e.g., Li et al., *Sci Transl Med.* 2015 Sep. 30; 7(307) and Bowen et al., *Neurology.* 2016 Oct. 25; 87(17):1756-1762, both references hereby incorporated by reference in their entireties.

In another aspect of the present invention, the anti-HERV-K Env antibody described herein can be used in various detection methods, for use in, e.g., monitoring the progression of an immunodeficiency virus infection; monitoring patient response to treatment for an immunodeficiency virus infection, monitoring the progression of cancer, autoimmune, neurological, and/or metabolic related diseases, etc. The present disclosure provides methods of detecting a HERV-K envelope polypeptide in a biological sample obtained from an individual. The methods generally involve: a) contacting the biological sample with a subject anti-HERV-K antibody; and b) detecting binding, if any, of the antibody to an epitope present in the sample. In some instances, the antibody comprises a detectable label. The level of HERV-K envelope polypeptide detected in the biological sample can provide an indication of the stage, degree, or severity of an immunodeficiency virus infection. The level of HERV-K polypeptide detected in the biological sample can provide an indication of the individual's response to treatment for an immunodeficiency virus infection.

Detection may occur by any known means in the art, for example, by immunoassay. By way of example, enzyme linked immunosorbent (ELISA) assays were used in Example 3 infra. Other immunoassays may include enzyme immune assays (EIA), ELISPOT (enzyme-linked immunospot), radioimmunoassays (RIAs), immunofluorescence, and other assays known in the art, including but not limited to Western Blot analysis and/or immunoprecipitation methods.

For example in a direct ELISA, a buffered solution of an antigen, e.g. a biological sample containing HERV-K, is added to a well of a microtiter plate, e.g. a 96-well plate, A solution of non-reacting protein, e.g. bovine serum albumin or casein is then added to the well. Anti-HERV-K antibody or antigen-binding portions thereof, typically conjugated to a reporter molecule enzyme, is added, e.g. conjugated to horse-radish peroxidase, although that is not necessarily the enzyme, as other common enzymes include alkaline phosphatase, or β-D-galactosidase, although other enzymes are conceivable and considered embodied by this disclosure. A substrate for the enzyme is then added, which leads to a detectable signal. For example, adding TMB to horseradish peroxidase leads to a colored product, in which case the ELISA is a colorimetric assay. ELISAs may be run in a qualitative or quantitative format. Qualitative results provide a simple positive or negative result (yes or no) for a sample. The cutoff between positive and negative is determined by an analyst and may be statistical. Sandwich ELISAs generally follow the following protocol. Capture anti-HERV-K antibodies are immobilized on a substrate, e.g. a microtiter plate. Antigen-containing sample is then added to the substrate at which point it is captured by the antibodies. The substrate is then washed to remove unbound antigen. Detecting anti-HERV-K antibodies are then added, which bind to different epitope(s) on HERV-K than the bound anti-HERV-K antibodies. The detecting antibodies may be bound to a reporter molecule, e.g. an enzyme, although the reporter molecule may be any molecule which leads to a detectable signal. Alternatively, a secondary antibody that is specific to the detecting antibody, for example (but not necessarily), anti-IgG antibodies, are added. The secondary antibody is often bound to a label, such as reporter molecule or an enzyme (or any other molecule that may lead to a detectable signal). The plate may be washed an additional time prior to adding in secondary antibody, and in those instances where the reporter molecule is an enzyme, a substrate may be added, e.g. TMB, that results in a detectable signal (also a colorimetric assay). A third type of common ELISA is competitive ELISA. In these embodiments, unlabeled anti-HERV-K antibodies incubated in the presence of an antigen-containing sample (e.g. a biological sample) which are then added to an antigen-coated well. The plate is washed so as to remove unbound antibodies. A secondary antibody that is specific to the primary antibody, for example (but not necessarily), anti-IgG antibodies, are added. The secondary antibody is bound to a label, such as reporter molecule or an enzyme (or any other molecule that may lead to a detectable signal). Some competitive ELISA utilize labeled antigens rather than labeled antibodies; the less antigen in the sample, the more labeled antigen is retained and the stronger a detectable signal results.

Other forms of common in vitro assays include radioimmunoassays (RIAs). Typically a known quantity of an antigen is linked to a radioactive tracer, e.g. 1-125 although others are suitable for use, which is then mixed with a known amount of antibody specific for the antigen, e.g. anti-HERV-K antibodies. Then, a sample containing unknown quantity of an antigen is added. This is a direct competitive measurement for specific binding; as the concentration of unlabeled antigen is increased, the binding between the antibodies and the labeled standard is decreased, which is directly measurable by measuring radioactivity. Other assays are known and a person of ordinary skill in the art would readily recognize their applicability.

The assays containing anti-HERV-K antibodies or antigen-binding portions thereof of the present disclosure may or may not be utilized for diagnostic purposes. Accordingly, in some embodiments, the invention is directed to methods of diagnostic use of the anti-HERV-K antibodies or antigen-binding portions thereof of the present disclosure.

Publications disclosed herein are provided solely for their disclosure prior to the filing date of the present disclosure. Nothing herein is to be construed as an admission that the present disclosure is not entitled to antedate such publication by virtue of prior invention. Further, the dates of publication provided may be different from the actual publication dates which may need to be independently confirmed.

Each of the applications and patents cited in this text, as well as each document or reference, patent or non-patent literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

Reference is now made to the following examples, which together with the above descriptions illustrate some embodiments of the invention in a non-limiting manner.

EXAMPLES

Example 1

Identification, Purification, and Recombinant Production of Fully Human Anti-HERV-K Env Monoclonal Antibodies Materials & Methods:

Peripheral blood samples were obtained from HIV-1 infected patients. PBMC were isolated within 2 h of sampling using CPT tubes (Becton Dickinson, Franklin Lakes, N.J.). Tubes were immediately inverted 8 to 10 times and processed according to the manufacturer's instructions.

To obtain HERV-K Env-specific B cells, PBMC were stained with fluorescently conjugated HERV-K Envelope protein and Tetanus Toxoid in addition to anti-CD19, anti-CD20, anti-IgD-PE, anti-CD3, anti-CD14, and 7AAD for dead cell exclusion at 4° C. for 60 min similar to as described in Kobie et al. *Monoclon Antib Immunodiagn Immunother.* 2015 Apr. 1; 34(2): 65-72, hereby incorporated by reference in its entirety. Single 7AAD− CD3− CD14− CD19+ Tetanus Toxoid− HERV-K Env+ cells were directly sorted using a FACSAria (BD Biosciences) directly into 96-well PCR plates (Bio-Rad, Hercules, Calif.) containing 4 µL/well 0.5×PBS with 10 mM DTT (Invitrogen), and 8 U RiboLock (ThermoFisher) RNAse inhibitor. Plates were sealed with MICROSEAL F FILM (Bio-Rad) and immediately frozen at −80° C. until used for RT-PCR.

Alternatively, single cells were sorted into 384-well tissue culture plates and cultured for 7-10 days. Following culture, qualitative 384-well ELISA was performed to identify wells containing cells secreting HERV-K Env-specific antibody. Alternatively, HERV-K Env specific B cells were enriched from PBMC by magnetic bead separation, and immortalized by transformation with Epstein Barr Virus (EBV), and screened for production of HERV-K Env-specific antibody by ELISA. Cells from positive wells were collected and re-suspended in PCR buffer.

cDNA was synthesized and semi-nested RT-PCR for IgH, Igλ, and Igκ V gene transcripts was performed as described in Kobie et al. Primers are indicated in TABLES 1, 2, and 3 below. Purified PCR2 products were sequenced at Genewiz Sequences and analyzed by IgBlast and IMGT/V-QUEST to identify germline V(D)J gene segments with highest identity and determine sequence properties. IgG expression vector cloning and transfection of human HEK293T cells (ATCC, Manassas, Va.) were performed as previously described in Kobie et al. and Tiller et al., *J Immunol Methods.* 2008 Jan. 1; 329(1-2): 112-124, hereby incorporated by reference in its entirety. IgG was purified from culture supernatant using MAGNA PROTEIN G beads (Promega, Madison, Wis.).

Sequence analysis was performed using an in-house custom analysis pipeline described in Tipon et al. *Nat Immunol* 2016; 16: 755-765, hereby incorporated by reference in its entirety. Sequences were then analyzed for V region mutations and clonality. All clonal assignments were based on matching V and J regions, matching HCDR3 length, and 85% HCDR3 homology.

Results:

Peripheral blood B cells were isolated from humans infected with HIV, HERV-K Env binding B cells isolated by flow cytometry. Heavy chain and light chain genes were sequenced and cloned by molecular biology techniques, and monoclonal antibodies were produced by transient transfection of HEK293T cells. Three, fully human, recombinant anti-HERV-K monoclonal antibodies were generated and expressed by this process, and were referred to as KSN-01, KSN-02, and KSN-03. None of KSN-01, KSN-02, and KSN-03 were detected in a patient sample prior to cloning.

Briefly, nucleotide sequences for the variable heavy/light chains of KSN-01, KSN-02, and KSN-03 were isolated from the peripheral blood B cells and cDNA encoding the variable heavy/light chains were cloned into vectors containing gene sequences encoding IgG1 constant regions. The peripheral blood B cells encoding the variable heavy/light chains of KSN-01 and KSN-02 were identified as containing IgM constant regions, and the peripheral blood B cell encoding the variable heavy/light chains of KSN-03 was identified as containing an IgA constant region. Thus, as produced by this Example, the recombinant antibodies KSN-01, KSN-02, and KSN-03 each contain a variant IgG Fc domain relative to the circulating memory B cell the variable heavy/light chain DNA sequences were isolated from. Restrictions sites were also added onto the sequences encoding KSN-01, KSN-02, and KSN-03 at the site where the cDNA encoding the variable regions were joined to the IgG1 constant regions.

TABLE 1

Primers for immunoglobulin genes (heavy chain)

| Heavy Chain | Name | Primer Sequence | SEQ ID NO: |
|---|---|---|---|
| Forward 5' | VH1 LEADER-A | ATGGACTGGACCTGGAGGAT | 34 |
| Forward 5' | VH1 LEADER-B | ATGGACTGGACCTGGAGCAT | 35 |
| Forward 5' | VH1 LEADER-C | ATGGACTGGACCTGGAGAAT | 36 |
| Forward 5' | VH1 LEADER-D | GGTTCCTCTTTGTGGTGGC | 37 |
| Forward 5' | VH1 LEADER-E | ATGGACTGGACCTGGAGGGT | 38 |
| Forward 5' | VH1 LEADER-F | ATGGACTGGATTTGGAGGAT | 39 |
| Forward 5' | VH1 LEADER-G | AGGTTCCTCTTTGTGGTGGCAG | 40 |
| Forward 5' | VH2Ext | CATACTTTGTTCCACGCTCC | 41 |
| Forward 5' | VH3 LEADER-A | TAAAAGGTGTCCAGTGT | 42 |
| Forward 5' | VH3 LEADER-B | TAAGAGGTGTCCAGTGT | 43 |
| Forward 5' | VH3 LEADER-C | TAGAAGGTGTCCAGTGT | 44 |

TABLE 1-continued

Primers for immunoglobulin genes (heavy chain)

| Heavy Chain | Name | Primer Sequence | SEQ ID NO: |
|---|---|---|---|
| Forward 5' | VH3 LEADER-D | GCTATTTTTAAAGGTGTCCAGTGT | 45 |
| Forward 5' | VH3 LEADER-E | TACAAGGTGTCCAGTGT | 46 |
| Forward 5' | VH3 LEADER-F | TTAAAGCTGTCCAGTGT | 47 |
| Forward 5' | VH4 LEADER-A | ATGAAACACCTGTGGTTCTTCC | 48 |
| Forward 5' | VH4 LEADER-B | ATGAAACACCTGTGGTTCTT | 49 |
| Forward 5' | VH4 LEADER-C | ATGAAGCACCTGTGGTTCTT | 50 |
| Forward 5' | VH4 LEADER-D | ATGAAACATCTGTGGTTCTT | 51 |
| Forward 5' | VH5 LEADER-A | TTCTCCAAGGAGTCTGT | 52 |
| Forward 5' | VH5 LEADER-B | CCTCCACAGTGAGAGTCTG | 53 |
| Forward 5' | VH6 LEADER-A | ATGTCTGTCTCCTTCCTCATC | 54 |
| Forward 5' | VH7 LEADER-A | GGCAGCAGCAACAGGTGCCCA | 55 |
| External 3' | IgMExt1 | GTGATGGAGTCGGGAAGGAA | 56 |
| External 3' | IgAExt | GTGTAGTGCTTCACGTGGCA | 57 |
| External 3' | IgGExt | GAGTCCTGAGGACTGTAGGA | 58 |
| Internal 3' | IgMInt1 | CGACGGGGAATTCTCACAGG | 59 |
| Internal 3' | IgAInt | GGCATGTCACGGACTTGCCG | 60 |
| Internal 3' | IgGInt | GCGCCTGAGTTCCACGACAC | 61 |

TABLE 2

Primers for immunoglobulin genes (kappa chain)

| Kappa Chain | Name | Primer Sequence | SEQ ID NO: |
|---|---|---|---|
| External 5' | 5' L VK1/2 | ATGAGGSTCCCYGCTCAGCTGCTGG | 62 |
| External 5' | 5' L VK3 | CTCTTCCTCCTGCTACTCTGGCTCCC | 63 |
| External 5' | 5' L VK4 | ATTTCTCTGTTGCTCTGGATCTCTG | 64 |
| External 3' | 3' CK 543 | GTTTCTCGTAGTCTGCTTTGCTCA | 65 |
| Internal 5' | 5' PAN VK | ATGACCCAGWCTCCABYCWCCCTG | 66 |
| Internal 3' | 3' CK 494 | GTGCTGTCCTTGCTGTCCTGCT | 67 |

TABLE 3

Primers for immunoglobulin genes (lambda chain)

| Lambda Chain | Name | Primer Sequence | SEQ ID NO: |
|---|---|---|---|
| External 5' | 5' L VL1 | GGTCCTGGGCCCAGTCTGTGCTG | 68 |
| External 5' | 5' L VL2 | GGTCCTGGGCCCAGTCTGCCCTG | 69 |
| External 5' | 5' L VL3 | GCTCTGTGACCTCCTATGAGCTG | 70 |
| External 5' | 5' L VL4/5 | GGTCTCTCTCSCAGCYTGTGCTG | 71 |
| External 5' | 5'L VL6 | GTTCTTGGGCCAATTTTATGCTG | 72 |
| External 5' | 5'L VL7 | GGTCCAATTCYCAGGCTGTGGTG | 73 |
| External 5' | 5' L VL8 | GAGTGGATTCTCAGACTGTGGTG | 74 |
| External 3' | 3' CL | CACCAGTGTGGCCTTGTTGCCTTG | 75 |
| Internal 5' | 5' AGEI VL1 | CTGCTACCGGTTCCTGGGCCCAGTC | 76 |
| Internal 5' | 5' AGEI VL2 | CTGCTACCGGTTCCTGGGCCCAGTC | 77 |
| Internal 5' | 5' AGEI VL3 | CTGCTACCGGTTCTGTGACCTCCTAT | 78 |
| Internal 5' | 5' AGEI VL4/5 | CTGCTACCGGTTCTCTCTCSCAGCYT | 79 |
| Internal 5' | 5' AGEI VL6 | CTGCTACCGGTTCTTGGGCCAATTTT | 80 |
| Internal 5' | 5' AGEI VL7/8 | CTGCTACCGGTTCCAATTCYCAGRCT | 81 |
| Internal 3' | 3' XHOI CL | CTCCTCACTCGAGGGYGGGAACAGA | 82 |

Example 2

Mapping of $V_L$ and $V_H$ Variable Region Sequences and CDR Sequences of KSN-01, KSN-02, and KSN-03.

Materials and Methods:

$V_L$ and $V_H$ variable region nucleotide sequences were obtained by Sanger sequencing and analyzed for homology to germline $V_L$ and $V_H$ sequences provided by IMGT using IgBlast.

Results:

Gene segments of highest homology are indicated in TABLE 4 below. KSN-01 utilizes the IGHV6-1, IGHD3-3, IGHJ6 heavy chain gene segments and the kappa IGKV1-5, IGKJ1 light chain gene segments. KSN-02 utilizes the IGHV4-34, IGHD3-3, IGHJ6 heavy chain gene segments and the lambda IGLV6-57, IGLJ4 light chain gene segments. KSN-03 utilizes the IGHV3-33, IGHD3-3, and IGHJ4 heavy chain gene segments and the kappa IGKV1-5, IGKJ2 light chain gene segments. The amino acid sequences of heavy and light chain CDRs of KSN-01, KSN-02, and KSN-03 are indicated in TABLE 5 below.

TABLE 4

Immunoglobulin gene usage

| mAb | Heavy chain | Light chain |
|---|---|---|
| KSN-01 | IGHV6-1 IGHD3-3 IGHJ6 | IGKV1-5 IGKJ1 |
| KSN-02 | IGHV4-34 IGHD3-3 IGHJ6 | IGLV6-57 IGLJ3 |
| KSN-03 | IGHV3-33 IGHD3-3 IGHJ4 | IGKV1-5 IGKJ2 |

TABLE 5

CDR amino acid sequences

| mAb | HCDR1 | HCDR2 | HCDR3 | LCDR1 | LCDR2 | LCDR3 |
|---|---|---|---|---|---|---|
| KSN-01 | GDSVSSNSAA (SEQ ID NO: 4) | TYYRSKWYN (SEQ ID NO: 5) | CARDRPWRGY RGYYYYYGMD VW (SEQ ID NO: 6) | QSISSW (SEQ ID NO: 7) | KAS (SEQ ID NO: 8) | CQQYNSY SWTF (SEQ ID NO: 9) |
| KSN-02 | GGSFSGYY (SEQ ID NO: 10) | INHSGST (SEQ ID NO: 11) | CARGRPLLRF LEWSRPYYYM DVW (SEQ ID NO: 12) | SGSIASN Y (SEQ ID NO: 13) | EDN (SEQ ID NO: 14) | CQSYDSS NHWVF (SEQ ID NO: 15) |
| KSN-03 | GFTFSSYG (SEQ ID NO: 16) | IWYDGSNK (SEQ ID NO: 17) | CAKRGGLEGF YYFDYW (SEQ ID NO: 18) | QSISSW (SEQ ID NO: 19) | KAS (SEQ ID NO: 20) | CQQYNSY SSF (SEQ ID NO: 21) |

KSN-01 heavy chain variable region (cDNA)
(SEQ ID NO: 28)
CAGGTACAGCTGCAGCAGTCAGGTCCAGGACTGGTGAAGCCCTCGCAGAC

CCTCTCACTCACCTGTGCCATCTCCGGGGACAGTGTCTCTAGCAACAGTG

CTGCTTGGAACTGGATCAGGCAGTCCCCATCGAGAGGCCTTGAGTGGCTG

GGAAGGACATACTACAGGTCCAAGTGGTATAATGATTATGCAGTATCTGT

GAAAAGTCGAATAACCATCAACCCAGACACATCCAAGAACCAGTTCTCCC

TGCAGCTGAACTCTGTGACTCCCGAGGACACGGCTGTGTATTACTGTGCA

AGAGATAGGCCCTGGCGTGGTTACCGAGGTTACTACTACTAGTACGGTAT

GGACGTCTGGGGCCAAGGGACCACGGTCACCGTCTCCTCAG

KSN-01 light chain variable region (cDNA)
(SEQ ID NO: 29)
GACATCCAGATGACCCAGTCTCCTTCCACCCTGTCTGCATCTGTAGGAGA

CAGAGTCACCATCACTTGCCGGGCCAGTCAGAGTATTAGTAGCTGGTTGG

CCTGGTATCAGCAGAAACCAGGGAAAGCCCCTAAGCTCCTGATCTATAAG

GCGTCTAGTTTAGAAAGTGGGGTCCCATCAAGGTTCAGCGGCAGTGGATC

TGGGACAGAATTCACTCTCACCATCAGCAGCCTGCAGCCTGATGATTTTG

CAACTTATTACTGCCAACAGTATAATAGTTATTCGTGGACGTTCGGCCAA

GGGACCAAGGTGGAAATCAAAC

KSN-02 heavy chain variable region (cDNA)
(SEQ ID NO: 30)
CAGGTGCAGCTACAGCAGTGGGGCGCAGGACTGTTGAAGCCTTCGGAGAC

CCTGTCCCTCACCTGCGCTGTCTATGGTGGGTCCTTCAGTGGTTACTACT

GGAGCTGGATCCGCCAGCCCCCAGGGAAGGGGCTGGAGTGGATTGGGAA

ATCAATCATAGTGGAAGCACCAACTACAACCCGTCCCTCAAGAGTCGAGT

CACCATATCAGTAGACACGTCCAAGAACCAGTTCTCCCTGAAGCTGAGCT

CTGTGACCGCCGCGGACACGGCTGTGTATTACTGTGCGAGAGGCCGCCCG

TTATTACGATTTTTGGAGTGGTCCAGGCCCTACTACTACATGGACGTCTG

GGGCAAAGGGACCACGGTCACCGTCTCCTCAG

KSN-02 light chain variable region (cDNA)
(SEQ ID NO: 31)
AATTTTATGCTGACTCAGCCGCACTCTGTGTCGGAGTCTCCGGGGAAGAC

GGTAACCATCTCCTGCACCCGCAGCAGTGGCAGCATTGCCAGCAACTATG

TGCAGTGGTACCAGCAGCGCCCGGGCAGTGCCCCCACCACTGTGATCTAT

GAGGATAACCAAAGACCCTCTGGGGTCCCTGATCGGTTCTCTGGCTCCAT

CGACAGCTCCTCCAACTCTGCCTCCCTCACCATCTCTGGACTGAAGACTG

AGGACGAGGCTGACTACTACTGTCAGTCTTATGATAGCAGCAACCATTGG

GTGTTCGGCGGAGGGACCAAGCTGACCGTCCTAGGTCAGCCCAAGGCTGC

CCCCTCGGTC

KSN-03 heavy chain variable region (cDNA)
(SEQ ID NO: 32)
AGGTGCAGCTGGTGGAGTCTGGGGGAGGCGTGGTCCAGCCTGGGAGGTCC

CTGAGACTCTCCTGTGCAGCGTCTGGATTCACCTTCAGTAGCTATGGCAT

GCACTGGGTCCGCCAGGCTCCAGGCAAGGGGCTGGAGTGGGTGGCAGTTA

TATGGTATGATGGAAGTAATAAATACTATGCAGACTCCGTGAAGGGCCGA

TTCACCATCTCCAGAGACAATTCCAAGAACACGCTGTATCTGCAAATGAA

CAGCCTGAGAGCCGAGGACACGGCTGTGTATTACTGTGCGAAACGAGGGG

GGTTGGAGGGCTTCTACTACTTTGACTACTGGGGCCAGGGAACCCTGGTC

ACCGTCTCCT

KSN-03 light chain variable region (cDNA)
(SEQ ID NO: 33)
CATCCGGATGACCCAGTCTCCTTCCACCCTGTCCGCATCTGTAGGAGACA

GAGTCACCATCACTTGCCGGGCCAGTCAGAGTATTAGTAGCTGGTTGGCC

TGGTATCAGCAGAAACCAGGGAAAGCCCCTAAGCTCCTGATCTATAAGGC

GTCTAGTTTAGAAAGTGGGGTCCCATCAAGGTTCAGCGGCAGTGGATCTG

GGACAGAATTCACTCTCACCATCAGCAGCCTGCAGCCTGATGATTTTGCA

ACTTATTACTGCCAACAGTATAATAGTTATTCCTCTTTCGGCCCTGGGAC

CAAGCTGGAGATCAAAC

Example 3

Binding of KSN-01, KSN-02, and KSN-03 to HERV-K Env Proteins (TM and SU Domains)

Materials and Methods:

ELISA plates were coated with recombinant HERV-K Env proteins, monoclonal antibodies were diluted in PBS+ 3% BSA, and binding detected with horseradish peroxidase-conjugated anti-human IgG. Polyclonal human IgG was used as a negative control. Samples were tested in triplicate.

Results:

Specificity of the antibodies was determined by ELISA using HERV-K SU and TM proteins. FIG. 1 indicates KSN-01 and KSN-02 antibodies have high binding activity for HERV-K SU protein and KSN-03 has high binding activity for HERV-K TM protein. Control human IgG (hIgG) displayed minimal binding activity for either protein.

It will be understood by those of skill in the art that numerous and various modifications can be made without departing from the scope and spirit of the present disclosure. Therefore, it should be understood that various embodiments of the invention described herein are illustrative only and not intended to limit the scope of the invention. All references cited herein are hereby incorporated by reference in their entirety.

The invention claimed is:

1. An isolated monoclonal antibody or antigen-binding fragment thereof that specifically binds to human HERV-K envelope polypeptide comprising:
   a heavy chain variable region comprising a HCDR1 comprising an amino acid sequence of SEQ ID NO: 4, a HCDR2 comprising an amino acid sequence of SEQ ID NO: 5 and a HCDR3 comprising an amino acid sequence of SEQ ID NO: 6; and a light chain variable region comprising a LCDR1 comprising an amino acid sequence of SEQ ID NO: 7, a LCDR2 comprising an amino acid sequence of SEQ ID NO: 8 and a LCDR3 comprising an amino acid sequence of SEQ ID NO: 9.

2. The isolated antibody or the antigen-binding fragment thereof of claim 1, wherein the heavy chain variable region comprises an amino acid sequence of SEQ ID NO: 23 and light chain variable region comprises an amino acid sequence of SEQ ID NO: 22.

3. The isolated antibody or the antigen-binding fragment thereof of claim 1, further comprising a variant Fc constant region.

4. The isolated antibody or the antigen-binding fragment thereof of claim 1, wherein the antibody is a human antibody or a chimeric antibody.

5. The isolated antibody or the antigen-binding fragment thereof of claim 1, wherein the antibody is conjugated to a therapeutic agent, a polymer, a detectable label or enzyme.

6. The isolated antibody or the antigen-binding fragment thereof of claim 5, wherein the polymer is polyethylene glycol (PEG).

7. The isolated antibody or the antigen-binding fragment thereof of claim 5, wherein the therapeutic agent is cytotoxic agent.

8. A pharmaceutical composition comprising the isolated antibody or claim 1 and a pharmaceutically acceptable carrier.

9. A kit for detecting the presence of HERV-K, or an antigenic fragment of HERV-K thereof, in a sample comprising (i) the isolated antibody or the antigen-binding fragment thereof of claim 1, and (ii) a buffer.

10. A nucleic acid sequence encoding a variable heavy chain region or a variable light chain region of the isolated antibody or the antigen-binding fragment thereof, of claim 1.

* * * * *